US007425622B2

(12) United States Patent
Rosen

(10) Patent No.: US 7,425,622 B2
(45) Date of Patent: Sep. 16, 2008

(54) ANTIBODIES AGAINST C3A RECEPTOR

(75) Inventor: Craig A. Rosen, Laytonsville, MD (US)

(73) Assignee: Human Genome Sciences, Inc., Rockville, MD (US)

(*) Notice: Subject to any disclaimer, the term of this patent is extended or adjusted under 35 U.S.C. 154(b) by 302 days.

(21) Appl. No.: 11/046,857

(22) Filed: Feb. 1, 2005

(65) Prior Publication Data

US 2005/0147605 A1 Jul. 7, 2005

Related U.S. Application Data

(63) Continuation-in-part of application No. PCT/US03/23826, filed on Jul. 31, 2003.

(60) Provisional application No. 60/400,057, filed on Aug. 2, 2002.

(51) Int. Cl.
*C07K 16/00* (2006.01)
*C12P 21/08* (2006.01)
*G01N 33/53* (2006.01)
*G01N 33/566* (2006.01)

(52) U.S. Cl. .............................. 530/388.2; 530/388.15; 530/388.22; 530/387.3; 530/391.3; 424/130.1; 435/7.2; 435/7.1; 435/69.1; 435/70.21; 436/501

(58) Field of Classification Search ........................ None
See application file for complete search history.

(56) References Cited

U.S. PATENT DOCUMENTS 6,342,220 B1   1/2002   Adams et al.

FOREIGN PATENT DOCUMENTS

WO    WO-02/002641    8/2002

OTHER PUBLICATIONS

Therien et al. Agonist activity of the small molecule C3aR ligand SB290157. J Immunol., 174, 7479-7480, 2005.*
Fruehauf et al., Innovative strategies for PBPC mobilization. Cytotherapy, 7, 438-446, 2005.*
Reca et al., Functional receptor for C3a anaphylatoxin is exxpressed by normal hematopoietic stem/ progenitor cells, and C3a enhances their homing-relateed responses to SDF-1. Blood, 101, 3784-3793, 2003.*
Griffiths, et al., "Human anti-self antibodies with high specificity from phage-display libraries," *Embo J.*, 12:725-734 (1993).
Marks, et al., "By-passing Immunization: Human antibodies from V-gene libraries displayed on phage," *J. Mol. Biol.*, 222:581-597 (1991).
Marriette, et al., "Nucleotide sequence analysis of the variable domains of four human monoclonal IgM with an antibody activity to myelin-associated glycoprotein," *Eur. J. Immunol.*, 23:846-851 (1993).
Mortari, et al., "The human cord blood antibody repertoirs. Frequent usage of the Vh7 gene family," *Eur. J. Immunology*, 22:241-245 (1992).
Raaphorst, et al., "Restricted utilization of germ-line Vh3 genes and the diverse third complementarity-determining regions (CDR3) in human fetal B lymphocyte immunoglobin heavy chain rearrangements," *Eur. J. Immunology*, 22:247-251 (1992).
Tomlison, et al., "The repertolre of human germline Vh sequences reveals about fifty groups of Vh segments with different hypervariable loops," *J. Mol. Biol.*, 227:776-798 (1992).
Wu, et al., "Myosin-reactive autoantibodies in rheumatic carditis and normal fetus," *Clin. Immunol. Immunopathol.*, 87:184-192 (1998).

* cited by examiner

*Primary Examiner*—Lorraine Spector
*Assistant Examiner*—Elly-Gerald Stoica

(57) ABSTRACT

The present invention relates to antibodies and related molecules that specifically bind to C3a Receptor. Such antibodies have uses, for example, in the prevention and treatment of asthma, allergy, and other related inflammatory and immune disorders. The invention also relates to nucleic acid molecules encoding anti-C3a Receptor antibodies, vectors and host cells containing these nucleic acids, and methods for producing the same. The present invention relates to methods and compositions for preventing, detecting, diagnosing, treating or ameliorating a disease or disorder, especially inflammatory and other related disorders, comprising administering to an animal, preferably a human, an effective amount of one or more antibodies or fragments or variants thereof, or related molecules, that specifically bind to C3a Receptor.

18 Claims, No Drawings

SEQUENCE LISTING

<160> NUMBER OF SEQ ID NOS: 50

<210> SEQ ID NO 1
<211> LENGTH: 2040
<212> TYPE: DNA
<213> ORGANISM: Homo sapiens
<220> FEATURE:

-continued

```
<221> NAME/KEY: CDS
<222> LOCATION: (153)..(1601)
<223> OTHER INFORMATION:

<400> SEQUENCE: 1
cacgaggaga acagaagaag agaaagctca gcaaattttc ttgccatact tcatgacttc        60
actgtggcta agtgtgggga ccagacagga ctcgtggaga catccaggtg ctgaagcctt       120
cagctactgt ctcagttttt tgaagtttag ca atg gcg tct ttc tct gct gag        173
                                   Met Ala Ser Phe Ser Ala Glu
                                     1               5 acc aat tca act gac cta ctc tca cag cca tgg aat gag ccc cca gta        221
Thr Asn Ser Thr Asp Leu Leu Ser Gln Pro Trp Asn Glu Pro Pro Val
         10                  15                  20 att ctc tcc atg gtc att ctc agc ctt act ttt tta ctg gga ttg cca        269
Ile Leu Ser Met Val Ile Leu Ser Leu Thr Phe Leu Leu Gly Leu Pro
 25                  30                  35 ggc aat ggg ctg gtg ctg tgg gtg gct ggc ctg aag atg cag cgg aca        317
Gly Asn Gly Leu Val Leu Trp Val Ala Gly Leu Lys Met Gln Arg Thr
 40                  45                  50                  55 gtg aac aca att tgg ttc ctc cac ctc acc ttg gcg gac ctc ctc tgc        365
Val Asn Thr Ile Trp Phe Leu His Leu Thr Leu Ala Asp Leu Leu Cys
                 60                  65                  70 tgc ctc tcc ttg ccc ttc tcg ctg gct cac ttg gct ctc cag gga cag        413
Cys Leu Ser Leu Pro Phe Ser Leu Ala His Leu Ala Leu Gln Gly Gln
             75                  80                  85 tgg ccc tac ggc agg ttc cta tgc aag ctc atc ccc tcc atc att gtc        461
Trp Pro Tyr Gly Arg Phe Leu Cys Lys Leu Ile Pro Ser Ile Ile Val
         90                  95                 100 ctc aac atg ttt gcc agt gtc ttc ctg ctt act gcc att agc ctg gat        509
Leu Asn Met Phe Ala Ser Val Phe Leu Leu Thr Ala Ile Ser Leu Asp
    105                 110                 115 cgc tgt ctt gtg gta ttc aag cca atc tgg tgt cag aat cat cgc aat        557
Arg Cys Leu Val Val Phe Lys Pro Ile Trp Cys Gln Asn His Arg Asn
120                 125                 130                 135 gta ggg atg gcc tgc tct atc tgt gga tgt atc tgg gtg gtg gct tgt        605
Val Gly Met Ala Cys Ser Ile Cys Gly Cys Ile Trp Val Val Ala Cys
                140                 145                 150 gtg atg tgc att cct gtg ttc gtg tac cgg gaa atc ttc act aca gac        653
Val Met Cys Ile Pro Val Phe Val Tyr Arg Glu Ile Phe Thr Thr Asp
            155                 160                 165 aac cat aat aga tgt ggc tac aaa ttt ggt ctc tcc agc tca tta gat        701
Asn His Asn Arg Cys Gly Tyr Lys Phe Gly Leu Ser Ser Ser Leu Asp
        170                 175                 180 tat cca gac ttt tat gga gat cca cta gaa aac agg tct ctt gaa aac        749
Tyr Pro Asp Phe Tyr Gly Asp Pro Leu Glu Asn Arg Ser Leu Glu Asn
    185                 190                 195 att gtt cag ccg cct gga gaa atg aat gat agg tta gat cct tcc tct        797
Ile Val Gln Pro Pro Gly Glu Met Asn Asp Arg Leu Asp Pro Ser Ser
200                 205                 210                 215 ttc caa aca aat gat cat cct tgg aca gtc ccc act gtc ttc caa cct        845
Phe Gln Thr Asn Asp His Pro Trp Thr Val Pro Thr Val Phe Gln Pro
                220                 225                 230 caa aca ttt caa aga cct tct gca gat tca ctc cct agg ggt tct gct        893
Gln Thr Phe Gln Arg Pro Ser Ala Asp Ser Leu Pro Arg Gly Ser Ala
            235                 240                 245 agg tta aca agt caa aat ctg tat tct aat gta ttt aaa cct gct gat        941
Arg Leu Thr Ser Gln Asn Leu Tyr Ser Asn Val Phe Lys Pro Ala Asp
        250                 255                 260 gtg gtc tca cct aaa atc ccc agt ggg ttt cct att gaa gat cac gaa        989
```

-continued

```
Val Val Ser Pro Lys Ile Pro Ser Gly Phe Pro Ile Glu Asp His Glu
    265                 270                 275 acc agc cca ctg gat aac tct gat gct ttt ctc tct act cat tta aag      1037
Thr Ser Pro Leu Asp Asn Ser Asp Ala Phe Leu Ser Thr His Leu Lys
280                 285                 290                 295 ctg ttc cct agc gct tct agc aat tcc ttc tac gag tct gag cta cca      1085
Leu Phe Pro Ser Ala Ser Ser Asn Ser Phe Tyr Glu Ser Glu Leu Pro
                300                 305                 310 caa ggt ttc cag gat tat tac aat tta ggc caa ttc aca gat gac gat      1133
Gln Gly Phe Gln Asp Tyr Tyr Asn Leu Gly Gln Phe Thr Asp Asp Asp
            315                 320                 325 caa gtg cca aca ccc ctc gtg gca ata acg atc act agg cta gtg gtg      1181
Gln Val Pro Thr Pro Leu Val Ala Ile Thr Ile Thr Arg Leu Val Val
        330                 335                 340 ggt ttc ctg ctg ccc tct gtt atc atg ata gcc tgt tac agc ttc att      1229
Gly Phe Leu Leu Pro Ser Val Ile Met Ile Ala Cys Tyr Ser Phe Ile
    345                 350                 355 gtc ttc cga atg caa agg ggc cgc ttc gcc aag tct cag agc aaa acc      1277
Val Phe Arg Met Gln Arg Gly Arg Phe Ala Lys Ser Gln Ser Lys Thr
360                 365                 370                 375 ttt cga gtg gcc gtg gtg gtg gct gtc ttt ctt gtc tgc tgg act      1325
Phe Arg Val Ala Val Val Val Ala Val Phe Leu Val Cys Trp Thr
                380                 385                 390 cca tac cac att ttt gga gtc ctg tca ttg ctt act gac cca gaa act      1373
Pro Tyr His Ile Phe Gly Val Leu Ser Leu Leu Thr Asp Pro Glu Thr
            395                 400                 405 ccc ttg ggg aaa act ctg atg tcc tgg gat cat gta tgc att gct cta      1421
Pro Leu Gly Lys Thr Leu Met Ser Trp Asp His Val Cys Ile Ala Leu
        410                 415                 420 gca tct gcc aat agt tgc ttt aat ccc ttc ctt tat gcc ctc ttg ggg      1469
Ala Ser Ala Asn Ser Cys Phe Asn Pro Phe Leu Tyr Ala Leu Leu Gly
    425                 430                 435 aaa gat ttt agg aag aaa gca agg cag tcc att cag gga att ctg gag      1517
Lys Asp Phe Arg Lys Lys Ala Arg Gln Ser Ile Gln Gly Ile Leu Glu
440                 445                 450                 455 gca gcc ttc agt gag gag ctc aca cgt tcc acc cac tgt ccc tca aac      1565
Ala Ala Phe Ser Glu Glu Leu Thr Arg Ser Thr His Cys Pro Ser Asn
                460                 465                 470 aat gtc att tca gaa aga aat agt aca act gtg tga aaatgtggag           1611
Asn Val Ile Ser Glu Arg Asn Ser Thr Thr Val
            475                 480 cagccaacaa gcaggggctc ttaggcaatc acatagtgaa agtttataag aggatgaagt    1671
gatatggtga gcagcggact tcaaaaactg tcaaagaatc aatccagcgg ttctcaaacg    1731
gtacacagac tattgacatc agcatcacct agaaacttgt tagaaatgca aattctcaag    1791
ccgcatccca gacttgctga atcggaatct ctggggttg ggacccagca agggcactta     1851
acaaaccccc gtttctgatt aatgctaaat gtaagaatca ttgtaaacat tagttctatt    1911
tctatcccaa actaagctat gtgaaataag agaagctact ttgtttttaa atgatgttga    1971
atatttgtcg atatttccat cattaaattt ttccttagca ttgtctaagt caaaaaaaaa    2031
aaaaaaaaa                                                            2040

<210> SEQ ID NO 2
<211> LENGTH: 482
<212> TYPE: PRT
<213> ORGANISM: Homo sapiens

<400> SEQUENCE: 2
```

-continued

```
Met Ala Ser Phe Ser Ala Glu Thr Asn Ser Thr Asp Leu Leu Ser Gln
1               5                   10                  15

Pro Trp Asn Glu Pro Val Ile Leu Ser Met Val Ile Leu Ser Leu
            20              25              30

Thr Phe Leu Leu Gly Leu Pro Gly Asn Gly Leu Val Leu Trp Val Ala
                35              40              45

Gly Leu Lys Met Gln Arg Thr Val Asn Thr Ile Trp Phe Leu His Leu
50              55                  60

Thr Leu Ala Asp Leu Leu Cys Cys Leu Ser Leu Pro Phe Ser Leu Ala
65                  70              75              80

His Leu Ala Leu Gln Gly Gln Trp Pro Tyr Gly Arg Phe Leu Cys Lys
                85              90              95

Leu Ile Pro Ser Ile Ile Val Leu Asn Met Phe Ala Ser Val Phe Leu
            100             105             110

Leu Thr Ala Ile Ser Leu Asp Arg Cys Leu Val Val Phe Lys Pro Ile
        115             120             125

Trp Cys Gln Asn His Arg Asn Val Gly Met Ala Cys Ser Ile Cys Gly
        130             135             140

Cys Ile Trp Val Val Ala Cys Val Met Cys Ile Pro Val Phe Val Tyr
145             150             155             160

Arg Glu Ile Phe Thr Thr Asp Asn His Asn Arg Cys Gly Tyr Lys Phe
                165             170             175

Gly Leu Ser Ser Ser Leu Asp Tyr Pro Asp Phe Tyr Gly Asp Pro Leu
            180             185             190

Glu Asn Arg Ser Leu Glu Asn Ile Val Gln Pro Pro Gly Glu Met Asn
        195             200             205

Asp Arg Leu Asp Pro Ser Ser Phe Gln Thr Asn Asp His Pro Trp Thr
    210             215             220

Val Pro Thr Val Phe Gln Pro Gln Thr Phe Gln Arg Pro Ser Ala Asp
225             230             235             240

Ser Leu Pro Arg Gly Ser Ala Arg Leu Thr Ser Gln Asn Leu Tyr Ser
            245             250             255

Asn Val Phe Lys Pro Ala Asp Val Val Ser Pro Lys Ile Pro Ser Gly
            260             265             270

Phe Pro Ile Glu Asp His Glu Thr Ser Pro Leu Asp Asn Ser Asp Ala
        275             280             285

Phe Leu Ser Thr His Leu Lys Leu Phe Pro Ser Ala Ser Ser Asn Ser
    290             295             300

Phe Tyr Glu Ser Glu Leu Pro Gln Gly Phe Gln Asp Tyr Tyr Asn Leu
305             310             315             320

Gly Gln Phe Thr Asp Asp Gln Val Pro Thr Pro Leu Val Ala Ile
            325             330             335

Thr Ile Thr Arg Leu Val Val Gly Phe Leu Leu Pro Ser Val Ile Met
        340             345             350

Ile Ala Cys Tyr Ser Phe Ile Val Phe Arg Met Gln Arg Gly Arg Phe
        355             360             365

Ala Lys Ser Gln Ser Lys Thr Phe Arg Val Ala Val Val Val Val Ala
    370             375             380

Val Phe Leu Val Cys Trp Thr Pro Tyr His Ile Phe Gly Val Leu Ser
385             390             395             400

Leu Leu Thr Asp Pro Glu Thr Pro Leu Gly Lys Thr Leu Met Ser Trp
            405             410             415

Asp His Val Cys Ile Ala Leu Ala Ser Ala Asn Ser Cys Phe Asn Pro
```

```
                420                 425                 430
Phe Leu Tyr Ala Leu Leu Gly Lys Asp Phe Arg Lys Lys Ala Arg Gln
        435                 440                 445

Ser Ile Gln Gly Ile Leu Glu Ala Ala Phe Ser Glu Glu Leu Thr Arg
        450                 455                 460

Ser Thr His Cys Pro Ser Asn Asn Val Ile Ser Glu Arg Asn Ser Thr
465                 470                 475                 480

Thr Val

<210> SEQ ID NO 3
<211> LENGTH: 1434
<212> TYPE: DNA
<213> ORGANISM: Mus musculus
<220> FEATURE:
<221> NAME/KEY: CDS
<222> LOCATION: (1)..(1434)
<223> OTHER INFORMATION:

<400> SEQUENCE: 3 atg gag tct ttc gat gct gac acc aat tca act gac cta cac tca cgg      48
Met Glu Ser Phe Asp Ala Asp Thr Asn Ser Thr Asp Leu His Ser Arg
1               5                   10                  15 cct ctg ttt caa ccc caa gac att gcc tcc atg gtc att ctt ggt ctc      96
Pro Leu Phe Gln Pro Gln Asp Ile Ala Ser Met Val Ile Leu Gly Leu
            20                  25                  30 act tgt cta ttg gga ctg cta ggc aat ggg ctg gtg ctg tgg gta gct     144
Thr Cys Leu Leu Gly Leu Leu Gly Asn Gly Leu Val Leu Trp Val Ala
        35                  40                  45 ggc gta aag atg aag acg acc gtg aac aca gtc tgg ttc ctc cat ctc     192
Gly Val Lys Met Lys Thr Thr Val Asn Thr Val Trp Phe Leu His Leu
    50                  55                  60 acc ctg gcc gat ttc ctc tgc tgc ctc tcc ttg ccc ttc tcc ttg gct     240
Thr Leu Ala Asp Phe Leu Cys Cys Leu Ser Leu Pro Phe Ser Leu Ala
65                  70                  75                  80 cac ctg att ctc caa gga cac tgg ccc tat ggc ttg ttc ctg tgc aaa     288
His Leu Ile Leu Gln Gly His Trp Pro Tyr Gly Leu Phe Leu Cys Lys
                85                  90                  95 ctt atc cca tcc atc att att ctc aac atg ttt gcc agt gtc ttc ctg     336
Leu Ile Pro Ser Ile Ile Ile Leu Asn Met Phe Ala Ser Val Phe Leu
            100                 105                 110 ctt act gcc att agc ctg gac cga tgt ctg ata gta cat aag cca atc     384
Leu Thr Ala Ile Ser Leu Asp Arg Cys Leu Ile Val His Lys Pro Ile
        115                 120                 125 tgg tgc cag aat cat cga aac gtg aga acc gcc ttc gcc atc tgt gga     432
Trp Cys Gln Asn His Arg Asn Val Arg Thr Ala Phe Ala Ile Cys Gly
    130                 135                 140 tgt gtc tgg gtg gta gcc ttt gtg atg tgt gtg ccc gta ttt gta tac     480
Cys Val Trp Val Val Ala Phe Val Met Cys Val Pro Val Phe Val Tyr
145                 150                 155                 160 cgt gat ctg ttc att atg gac aat cgc agt ata tgt aga tat aat ttt     528
Arg Asp Leu Phe Ile Met Asp Asn Arg Ser Ile Cys Arg Tyr Asn Phe
                165                 170                 175 gat tcc tcc agg tca tat gat tat tgg gac tac gtg tac aaa cta agt     576
Asp Ser Ser Arg Ser Tyr Asp Tyr Trp Asp Tyr Val Tyr Lys Leu Ser
            180                 185                 190 cta cca gaa agc aat tct act gat aac tcc act gct cag cta act gga     624
Leu Pro Glu Ser Asn Ser Thr Asp Asn Ser Thr Ala Gln Leu Thr Gly
        195                 200                 205 cat atg aat gac agg tca gct cct tcc tct gta cag gca agg gat tac     672
His Met Asn Asp Arg Ser Ala Pro Ser Ser Val Gln Ala Arg Asp Tyr
```

```
                210                 215                 220
ttt tgg aca gtt acc act gcc ctc cag tca cag cca ttc cta aca tct    720
Phe Trp Thr Val Thr Thr Ala Leu Gln Ser Gln Pro Phe Leu Thr Ser
225                 230                 235                 240 cct gaa gac tca ttc tct cta gat tca gca aac caa caa ccc cat tat    768
Pro Glu Asp Ser Phe Ser Leu Asp Ser Ala Asn Gln Gln Pro His Tyr
                245                 250                 255 ggt gga aag cct cct aat gtc ctc aca gcc gcc gta ccc agc ggg ttt    816
Gly Gly Lys Pro Pro Asn Val Leu Thr Ala Ala Val Pro Ser Gly Phe
            260                 265                 270 cct gtt gaa gat cgt aaa tcc aat aca ctg aac gct gac gct ttt ctc    864
Pro Val Glu Asp Arg Lys Ser Asn Thr Leu Asn Ala Asp Ala Phe Leu
        275                 280                 285 tct gct cac aca gaa ctt ttc cct act gct tct agt ggt cat tta tac    912
Ser Ala His Thr Glu Leu Phe Pro Thr Ala Ser Ser Gly His Leu Tyr
    290                 295                 300 ccc tat gat ttc cag ggg gat tat gtt gac caa ttc acg tat gac aat    960
Pro Tyr Asp Phe Gln Gly Asp Tyr Val Asp Gln Phe Thr Tyr Asp Asn
305                 310                 315                 320 cat gtg ccg aca ccg ctg atg gca ata acc atc aca agg ctg gtg gtg    1008
His Val Pro Thr Pro Leu Met Ala Ile Thr Ile Thr Arg Leu Val Val
                325                 330                 335 ggc ttc ctg gtg ccg ttt ttc atc atg gta att tgt tac agc ctc atc    1056
Gly Phe Leu Val Pro Phe Phe Ile Met Val Ile Cys Tyr Ser Leu Ile
            340                 345                 350 gtc ttc aga atg cga aaa acc aac ttc acc aag tct cgg aac aaa acc    1104
Val Phe Arg Met Arg Lys Thr Asn Phe Thr Lys Ser Arg Asn Lys Thr
        355                 360                 365 ttt cgg gtg gct gtg gct gtg gtc act gtc ttt ttt atc tgc tgg act    1152
Phe Arg Val Ala Val Ala Val Val Thr Val Phe Phe Ile Cys Trp Thr
370                 375                 380 cca tac cat ctt gtc gga gtc ctg cta ttg att act gat cca gaa agt    1200
Pro Tyr His Leu Val Gly Val Leu Leu Leu Ile Thr Asp Pro Glu Ser
385                 390                 395                 400 tcc ttg ggg gaa gct gtg atg tcc tgg gac cac atg tcc att gct tta    1248
Ser Leu Gly Glu Ala Val Met Ser Trp Asp His Met Ser Ile Ala Leu
                405                 410                 415 gca tct gcc aat agt tgc ttc aac cct ttc ctg tat gcc ctc ttg ggg    1296
Ala Ser Ala Asn Ser Cys Phe Asn Pro Phe Leu Tyr Ala Leu Leu Gly
            420                 425                 430 aaa gac ttt agg aag aaa gca aga cag tct ata aag ggc att ctg gaa    1344
Lys Asp Phe Arg Lys Lys Ala Arg Gln Ser Ile Lys Gly Ile Leu Glu
        435                 440                 445 gca gcc ttc agc gaa gag ctc acg cac tct acc aac tgt acc caa gac    1392
Ala Ala Phe Ser Glu Glu Leu Thr His Ser Thr Asn Cys Thr Gln Asp
    450                 455                 460 aaa gcc tct tca aaa aga aac aat atg agt aca gat gtg tga             1434
Lys Ala Ser Ser Lys Arg Asn Asn Met Ser Thr Asp Val
465                 470                 475

<210> SEQ ID NO 4
<211> LENGTH: 477
<212> TYPE: PRT
<213> ORGANISM: Mus musculus

<400> SEQUENCE: 4

Met Glu Ser Phe Asp Ala Asp Thr Asn Ser Thr Asp Leu His Ser Arg
1               5                   10                  15

Pro Leu Phe Gln Pro Gln Asp Ile Ala Ser Met Val Ile Leu Gly Leu
            20                  25                  30
```

```
Thr Cys Leu Leu Gly Leu Leu Gly Asn Gly Leu Val Leu Trp Val Ala
        35                  40                  45
Gly Val Lys Met Lys Thr Thr Val Asn Thr Val Trp Phe Leu His Leu
 50                  55                  60
Thr Leu Ala Asp Phe Leu Cys Cys Leu Ser Leu Pro Phe Ser Leu Ala
 65                  70                  75                  80
His Leu Ile Leu Gln Gly His Trp Pro Tyr Gly Leu Phe Leu Cys Lys
                 85                  90                  95
Leu Ile Pro Ser Ile Ile Ile Leu Asn Met Phe Ala Ser Val Phe Leu
                100                 105                 110
Leu Thr Ala Ile Ser Leu Asp Arg Cys Leu Ile Val His Lys Pro Ile
            115                 120                 125
Trp Cys Gln Asn His Arg Asn Val Arg Thr Ala Phe Ala Ile Cys Gly
        130                 135                 140
Cys Val Trp Val Val Ala Phe Val Met Cys Val Pro Val Phe Val Tyr
145                 150                 155                 160
Arg Asp Leu Phe Ile Met Asp Asn Arg Ser Ile Cys Arg Tyr Asn Phe
                165                 170                 175
Asp Ser Ser Arg Ser Tyr Asp Tyr Trp Asp Tyr Val Tyr Lys Leu Ser
                180                 185                 190
Leu Pro Glu Ser Asn Ser Thr Asp Asn Ser Thr Ala Gln Leu Thr Gly
            195                 200                 205
His Met Asn Asp Arg Ser Ala Pro Ser Ser Val Gln Ala Arg Asp Tyr
        210                 215                 220
Phe Trp Thr Val Thr Thr Ala Leu Gln Ser Gln Pro Phe Leu Thr Ser
225                 230                 235                 240
Pro Glu Asp Ser Phe Ser Leu Asp Ser Ala Asn Gln Gln Pro His Tyr
                245                 250                 255
Gly Gly Lys Pro Pro Asn Val Leu Thr Ala Ala Val Pro Ser Gly Phe
                260                 265                 270
Pro Val Glu Asp Arg Lys Ser Asn Thr Leu Asn Ala Asp Ala Phe Leu
            275                 280                 285
Ser Ala His Thr Glu Leu Phe Pro Thr Ala Ser Ser Gly His Leu Tyr
        290                 295                 300
Pro Tyr Asp Phe Gln Gly Asp Tyr Val Asp Gln Phe Thr Tyr Asp Asn
305                 310                 315                 320
His Val Pro Thr Pro Leu Met Ala Ile Thr Ile Thr Arg Leu Val Val
                325                 330                 335
Gly Phe Leu Val Pro Phe Phe Ile Met Val Ile Cys Tyr Ser Leu Ile
                340                 345                 350
Val Phe Arg Met Arg Lys Thr Asn Phe Thr Lys Ser Arg Asn Lys Thr
            355                 360                 365
Phe Arg Val Ala Val Ala Val Thr Val Phe Phe Ile Cys Trp Thr
        370                 375                 380
Pro Tyr His Leu Val Gly Val Leu Leu Leu Ile Thr Asp Pro Glu Ser
385                 390                 395                 400
Ser Leu Gly Glu Ala Val Met Ser Trp Asp His Met Ser Ile Ala Leu
                405                 410                 415
Ala Ser Ala Asn Ser Cys Phe Asn Pro Phe Leu Tyr Ala Leu Leu Gly
            420                 425                 430
Lys Asp Phe Arg Lys Lys Ala Arg Gln Ser Ile Lys Gly Ile Leu Glu
        435                 440                 445
```

Ala Ala Phe Ser Glu Glu Leu Thr His Ser Thr Asn Cys Thr Gln Asp
    450                 455                 460

Lys Ala Ser Ser Lys Arg Asn Asn Met Ser Thr Asp Val
465                 470                 475

<210> SEQ ID NO 5
<211> LENGTH: 23
<212> TYPE: DNA
<213> ORGANISM: Artificial sequence
<220> FEATURE:
<223> OTHER INFORMATION: VH Primer Hu VH1-5'

<400> SEQUENCE: 5
caggtgcagc tggtgcagtc tgg                                              23

<210> SEQ ID NO 6
<211> LENGTH: 23
<212> TYPE: DNA
<213> ORGANISM: Artificial sequence
<220> FEATURE:
<223> OTHER INFORMATION: VH Primer Hu VH2-5'

<400> SEQUENCE: 6
caggtcaact taagggagtc tgg                                              23

<210> SEQ ID NO 7
<211> LENGTH: 23
<212> TYPE: DNA
<213> ORGANISM: Artificial sequence
<220> FEATURE:
<223> OTHER INFORMATION: VH Primer Hu VH3-5'

<400> SEQUENCE: 7
gaggtgcagc tggtggagtc tgg                                              23

<210> SEQ ID NO 8
<211> LENGTH: 23
<212> TYPE: DNA
<213> ORGANISM: Artificial sequence
<220> FEATURE:
<223> OTHER INFORMATION: VH Primer Hu VH4-5'

<400> SEQUENCE: 8
caggtgcagc tgcaggagtc ggg                                              23

<210> SEQ ID NO 9
<211> LENGTH: 23
<212> TYPE: DNA
<213> ORGANISM: Artificial sequence
<220> FEATURE:
<223> OTHER INFORMATION: VH Primer Hu VH5-5'

<400> SEQUENCE: 9
gaggtgcagc tgttgcagtc tgc                                              23

<210> SEQ ID NO 10
<211> LENGTH: 23
<212> TYPE: DNA
<213> ORGANISM: Artificial sequence
<220> FEATURE:
<223> OTHER INFORMATION: VH Primer Hu VH6-5'

<400> SEQUENCE: 10
caggtacagc tgcagcagtc agg                                              23

```
<210> SEQ ID NO 11
<211> LENGTH: 24
<212> TYPE: DNA
<213> ORGANISM: Artificial sequence
<220> FEATURE:
<223> OTHER INFORMATION: VH Primer Hu JH1,2-5'

<400> SEQUENCE: 11
tgaggagacg gtgaccaggg tgcc                                          24

<210> SEQ ID NO 12
<211> LENGTH: 24
<212> TYPE: DNA
<213> ORGANISM: Artificial sequence
<220> FEATURE:
<223> OTHER INFORMATION: VH Primer Hu JH3-5'

<400> SEQUENCE: 12
tgaagagacg gtgaccattg tccc                                          24

<210> SEQ ID NO 13
<211> LENGTH: 24
<212> TYPE: DNA
<213> ORGANISM: Artificial sequence
<220> FEATURE:
<223> OTHER INFORMATION: VH Primer Hu JH4,5-5'

<400> SEQUENCE: 13
tgaggagacg gtgaccaggg ttcc                                          24

<210> SEQ ID NO 14
<211> LENGTH: 24
<212> TYPE: DNA
<213> ORGANISM: Artificial sequence
<220> FEATURE:
<223> OTHER INFORMATION: VH Primer Hu JH6-5'

<400> SEQUENCE: 14
tgaggagacg gtgaccgtgg tccc                                          24

<210> SEQ ID NO 15
<211> LENGTH: 23
<212> TYPE: DNA
<213> ORGANISM: Artificial sequence
<220> FEATURE:
<223> OTHER INFORMATION: VL Primer Hu Vkappa1-5'

<400> SEQUENCE: 15
gacatccaga tgacccagtc tcc                                           23

<210> SEQ ID NO 16
<211> LENGTH: 23
<212> TYPE: DNA
<213> ORGANISM: Artificial sequence
<220> FEATURE:
<223> OTHER INFORMATION: VL Primer Hu Vkappa2a-5'

<400> SEQUENCE: 16
gatgttgtga tgactcagtc tcc                                           23

<210> SEQ ID NO 17
<211> LENGTH: 23
<212> TYPE: DNA
<213> ORGANISM: Artificial sequence
<220> FEATURE:
<223> OTHER INFORMATION: VL Primer Hu Vkappa2b-5'
```

```
<400> SEQUENCE: 17
gatattgtga tgactcagtc tcc                                              23

<210> SEQ ID NO 18
<211> LENGTH: 23
<212> TYPE: DNA
<213> ORGANISM: Artificial sequence
<220> FEATURE:
<223> OTHER INFORMATION: VL Primer Hu Vkappa3-5'

<400> SEQUENCE: 18
gaaattgtgt tgacgcagtc tcc                                              23

<210> SEQ ID NO 19
<211> LENGTH: 23
<212> TYPE: DNA
<213> ORGANISM: Artificial sequence
<220> FEATURE:
<223> OTHER INFORMATION: VL Primer Hu Vkappa4-5'

<400> SEQUENCE: 19
gacatcgtga tgacccagtc tcc                                              23

<210> SEQ ID NO 20
<211> LENGTH: 23
<212> TYPE: DNA
<213> ORGANISM: Artificial sequence
<220> FEATURE:
<223> OTHER INFORMATION: VL Primer Hu Vkappa5-5'

<400> SEQUENCE: 20
gaaacgacac tcacgcagtc tcc                                              23

<210> SEQ ID NO 21
<211> LENGTH: 23
<212> TYPE: DNA
<213> ORGANISM: Artificial sequence
<220> FEATURE:
<223> OTHER INFORMATION: VL Primer Hu Vkappa6-5'

<400> SEQUENCE: 21
gaaattgtgc tgactcagtc tcc                                              23

<210> SEQ ID NO 22
<211> LENGTH: 23
<212> TYPE: DNA
<213> ORGANISM: Artificial sequence
<220> FEATURE:
<223> OTHER INFORMATION: VL Primer Hu Vlambda1-5'

<400> SEQUENCE: 22
cagtctgtgt tgacgcagcc gcc                                              23

<210> SEQ ID NO 23
<211> LENGTH: 23
<212> TYPE: DNA
<213> ORGANISM: Artificial sequence
<220> FEATURE:
<223> OTHER INFORMATION: VL Primer Hu Vlambda2-5'

<400> SEQUENCE: 23
cagtctgccc tgactcagcc tgc                                              23

<210> SEQ ID NO 24
<211> LENGTH: 23
```

```
<212> TYPE: DNA
<213> ORGANISM: Artificial sequence
<220> FEATURE:
<223> OTHER INFORMATION: VL Primer Hu Vlambda3-5'

<400> SEQUENCE: 24
tcctatgtgc tgactcagcc acc                                              23

<210> SEQ ID NO 25
<211> LENGTH: 23
<212> TYPE: DNA
<213> ORGANISM: Artificial sequence
<220> FEATURE:
<223> OTHER INFORMATION: VL Primer Hu Vlambda3b-5'

<400> SEQUENCE: 25
tcttctgagc tgactcagga ccc                                              23

<210> SEQ ID NO 26
<211> LENGTH: 23
<212> TYPE: DNA
<213> ORGANISM: Artificial sequence
<220> FEATURE:
<223> OTHER INFORMATION: VL Primer Hu Vlambda4-5'

<400> SEQUENCE: 26
cacgttatac tgactcaacc gcc                                              23

<210> SEQ ID NO 27
<211> LENGTH: 23
<212> TYPE: DNA
<213> ORGANISM: Artificial sequence
<220> FEATURE:
<223> OTHER INFORMATION: VL Primer Hu Vlambda5-5'

<400> SEQUENCE: 27
caggctgtgc tcactcagcc gtc                                              23

<210> SEQ ID NO 28
<211> LENGTH: 23
<212> TYPE: DNA
<213> ORGANISM: Artificial sequence
<220> FEATURE:
<223> OTHER INFORMATION: VL Primer Hu Vlambda6-5'

<400> SEQUENCE: 28
aattttatgc tgactcagcc cca                                              23

<210> SEQ ID NO 29
<211> LENGTH: 24
<212> TYPE: DNA
<213> ORGANISM: Artificial sequence
<220> FEATURE:
<223> OTHER INFORMATION: VL Primer Hu Jkappa1-3'

<400> SEQUENCE: 29
acgtttgatt tccaccttgg tccc                                             24

<210> SEQ ID NO 30
<211> LENGTH: 24
<212> TYPE: DNA
<213> ORGANISM: Artificial sequence
<220> FEATURE:
<223> OTHER INFORMATION: VL Primer Hu Jkappa2-3'

<400> SEQUENCE: 30
```

-continued acgtttgatc tccagcttgg tccc                24

<210> SEQ ID NO 31
<211> LENGTH: 24
<212> TYPE: DNA
<213> ORGANISM: Artificial sequence
<220> FEATURE:
<223> OTHER INFORMATION: VL Primer Hu Jkappa3-3'

<400> SEQUENCE: 31
acgtttgata tccactttgg tccc                24

<210> SEQ ID NO 32
<211> LENGTH: 24
<212> TYPE: DNA
<213> ORGANISM: Artificial sequence
<220> FEATURE:
<223> OTHER INFORMATION: VL Primer Hu Jkappa4-3'

<400> SEQUENCE: 32
acgtttgatc tccaccttgg tccc                24

<210> SEQ ID NO 33
<211> LENGTH: 24
<212> TYPE: DNA
<213> ORGANISM: Artificial sequence
<220> FEATURE:
<223> OTHER INFORMATION: VL Primer Hu Jkappa5-3'

<400> SEQUENCE: 33
acgtttaatc tccagtcgtg tccc                24

<210> SEQ ID NO 34
<211> LENGTH: 23
<212> TYPE: DNA
<213> ORGANISM: Artificial sequence
<220> FEATURE:
<223> OTHER INFORMATION: VL Primer Hu Jlambda1-3'

<400> SEQUENCE: 34
cagtctgtgt tgacgcagcc gcc                 23

<210> SEQ ID NO 35
<211> LENGTH: 23
<212> TYPE: DNA
<213> ORGANISM: Artificial sequence
<220> FEATURE:
<223> OTHER INFORMATION: VL Primer Hu Jlambda2-3'

<400> SEQUENCE: 35
cagtctgccc tgactcagcc tgc                 23

<210> SEQ ID NO 36
<211> LENGTH: 23
<212> TYPE: DNA
<213> ORGANISM: Artificial sequence
<220> FEATURE:
<223> OTHER INFORMATION: VL Primer Hu Jlambda3--3'

<400> SEQUENCE: 36
tcctatgtgc tgactcagcc acc                 23

<210> SEQ ID NO 37
<211> LENGTH: 23
<212> TYPE: DNA
<213> ORGANISM: Artificial sequence

```
<220> FEATURE:
<223> OTHER INFORMATION: VL Primer Hu Jlambda3b-3'

<400> SEQUENCE: 37
tcttctgagc tgactcagga ccc                                               23

<210> SEQ ID NO 38
<211> LENGTH: 23
<212> TYPE: DNA
<213> ORGANISM: Artificial sequence
<220> FEATURE:
<223> OTHER INFORMATION: VL Primer Hu Jlambda4-3'

<400> SEQUENCE: 38
cacgttatac tgactcaacc gcc                                               23

<210> SEQ ID NO 39
<211> LENGTH: 23
<212> TYPE: DNA
<213> ORGANISM: Artificial sequence
<220> FEATURE:
<223> OTHER INFORMATION: VL Primer Hu Jlambda5-3'

<400> SEQUENCE: 39
caggctgtgc tcactcagcc gtc                                               23

<210> SEQ ID NO 40
<211> LENGTH: 23
<212> TYPE: DNA
<213> ORGANISM: Artificial sequence
<220> FEATURE:
<223> OTHER INFORMATION: VL Primer Hu Jlambda6-3'

<400> SEQUENCE: 40
aattttatgc tgactcagcc cca                                               23

<210> SEQ ID NO 41
<211> LENGTH: 26
<212> TYPE: DNA
<213> ORGANISM: Artificial Sequence
<220> FEATURE:
<223> OTHER INFORMATION: 5' primer for amplifying C3a Receptor
      containing a BamHI restriction enzyme site followed by four
      nucleotides resembling an efficient signal for the initiation of
      translation in eukaryotic cells

<400> SEQUENCE: 41
cgggatccct catgcgtctt tctgct                                            26

<210> SEQ ID NO 42
<211> LENGTH: 24
<212> TYPE: DNA
<213> ORGANISM: Artificial Sequence
<220> FEATURE:
<223> OTHER INFORMATION: 3' primer for amplifying C3a Receptor
      containing the cleavage site for the restriction endonuclease
      BamHI and 18 nucleotides complementary to the 3' non-translated
      sequence of the C3a Receptor gene

<400> SEQUENCE: 42
cgggatcccg ctcacacagg tact                                              24

<210> SEQ ID NO 43
<211> LENGTH: 257
<212> TYPE: PRT
<213> ORGANISM: Artificial sequence
<220> FEATURE:
```

<223> OTHER INFORMATION: D098G01 scFv

<400> SEQUENCE: 43

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Gly Tyr Asn Gly Asp Thr Asn Tyr Ala Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Ile Tyr Tyr Cys
                85                  90                  95

Thr Arg Asp Leu Pro Gly Leu Asn Trp Ala Tyr Ser Tyr Asp Tyr Met
            100                 105                 110

Asp Val Trp Gly Arg Gly Thr Leu Val Thr Val Ser Ser Gly Gly Gly
        115                 120                 125

Gly Ser Gly Gly Gly Gly Ser Gly Gly Gly Gly Ser Ala Gln Ala Val
    130                 135                 140

Leu Thr Gln Pro Ser Ser Leu Ser Ala Ser Pro Gly Thr Ser Ala Ser
145                 150                 155                 160

Leu Thr Cys Thr Leu Arg Ser Gly Ile Asn Val Gly Thr Tyr Arg Ile
                165                 170                 175

Tyr Trp Tyr Gln Gln Lys Pro Gly Ser Pro Pro His Phe Leu Leu Arg
            180                 185                 190

Tyr Lys Ser Asp Ser Asp Lys Gln Gln Gly Ser Gly Val Pro Ser Arg
        195                 200                 205

Phe Ser Gly Ser Lys Asp Ala Ser Ala Asn Ala Gly Ile Leu Leu Ile
    210                 215                 220

Ser Gly Leu Gln Ser Asp Asp Glu Ala Asp Tyr Tyr Cys Met Ile Trp
225                 230                 235                 240

His Ser Ser Ala Trp Val Phe Gly Gly Gly Thr Lys Val Thr Val Leu
                245                 250                 255

Gly

<210> SEQ ID NO 44
<211> LENGTH: 247
<212> TYPE: PRT
<213> ORGANISM: Artificial sequence
<220> FEATURE:
<223> OTHER INFORMATION: D185G07 scFv

<400> SEQUENCE: 44

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

-continued

```
Leu Gln Met Asn Ser Leu Arg Ala Glu Asp Thr Ala Val Tyr Tyr Cys
                 85                  90                  95
Ala Arg Gly Pro Asp Tyr Asp Ser Tyr Asp Ala Phe Asp Ile Trp Gly
            100                 105                 110
Lys Gly Thr Leu Val Thr Val Ser Leu Gly Gly Gly Gly Ser Gly Gly
        115                 120                 125
Gly Gly Ser Gly Gly Gly Ser Gln Ser Val Leu Thr Gln Pro Pro
    130                 135                 140
Ser Val Ser Ala Ala Pro Gly Gln Lys Val Thr Ile Ser Cys Ser Gly
145                 150                 155                 160
Ser Thr Ser Asn Ile Gly Asn Asn Tyr Val Ser Trp Tyr Gln Gln His
                165                 170                 175
Pro Gly Lys Ala Pro Lys Leu Met Ile Tyr Asp Val Ser Lys Arg Pro
            180                 185                 190
Ser Gly Val Pro Asp Arg Phe Ser Gly Ser Lys Ser Gly Asn Ser Val
        195                 200                 205
Ser Leu Asp Ile Ser Gly Leu Gln Ser Glu Asp Glu Ala Asp Tyr Tyr
    210                 215                 220
Cys Ala Ala Trp Asp Asp Ser Leu Ser Glu Phe Leu Phe Gly Thr Gly
225                 230                 235                 240
Thr Lys Leu Thr Val Leu Gly
                245
```

```
<210> SEQ ID NO 45
<211> LENGTH: 771
<212> TYPE: DNA
<213> ORGANISM: Artificial Sequence
<220> FEATURE:
<223> OTHER INFORMATION: polynucleotide encoding D098G01 DNA

<400> SEQUENCE: 45
```

| | | | | | |
|---|---|---|---|---|---|
| gaggtgcagc | tggtgcagtc | tggggctgag | gtgaggaagc | tggggcctc | agtgaaggtc | 60 |
| tcctgcaagg | cttctggtta | cagttttacc | aactacggta | tcacctgggt | gcgacaggcc | 120 |
| cctggacagg | gcttgagtg | gatgggatgg | atcagcggtt | acaatggtga | cacaaactat | 180 |
| gcacagaagc | tccagggcag | agtcaccatg | accacagaca | catccacgaa | cacagcctac | 240 |
| atggagctga | ggagcctgag | atctgacgac | acggccattt | attactgtac | gagagaccta | 300 |
| cccggactta | actgggcata | ctcctacgac | tacatggacg | tctggggccg | ggaaccctg | 360 |
| gtcaccgtct | cgagtggagg | cggcggttca | ggcggaggtg | gctctggcgg | tggcggaagt | 420 |
| gcacaggctg | tgctgactca | gccgtcttcc | ctctctgcat | ctcctggaac | atcagccagt | 480 |
| ctcacctgca | ccttgcgcag | tggcatcaat | gttggtacct | acaggatata | ctggtaccag | 540 |
| cagaagccag | ggagtcctcc | ccatttctc | ctgcggtaca | aatcagactc | agataaacag | 600 |
| cagggctctg | gagtccccag | ccgcttctct | ggatccaaag | atgcttcggc | caatgcaggg | 660 |
| attttactca | tctctgggct | ccagtctgac | gatgaggctg | actattactg | tatgatttgg | 720 |
| cacagcagcg | cttgggtgtt | cggcggaggg | accaaggtca | ccgtcctagg | t | 771 |

```
<210> SEQ ID NO 46
<211> LENGTH: 741
<212> TYPE: DNA
<213> ORGANISM: Artificial sequence
<220> FEATURE:
<223> OTHER INFORMATION: Polynucleotide encoding D185G07 scFv

<400> SEQUENCE: 46
```

-continued

```
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtagtagtta cacaaactac   180
gcagactctg tgaagggccg attcaccatc tccagagaca acgccaagaa ctcactgtat   240
ctgcaaatga acagcctgag agccgaggac acggccgtgt attactgtgc gagaggcccc   300
gactatgata gttatgatgc ttttgatatc tggggcaagg gaaccctggt caccgtctcc   360
ttaggtggag gcggttcagg cggaggtggc agcggcggtg gcggatcgca gtctgtgttg   420
acgcagccgc cctcagtgtc tgcggcccca ggacagaagg tcaccatttc ctgctctgga   480
agcacctcca acattgggaa taattatgtc tcctggtacc aacagcaccc aggcaaagcc   540
cccaaactca tgatttatga tgtcagtaag cggccctcag ggtccctga ccgattctct   600 ggctccaagt ctggcaactc agtctccctg gacatcagtg gctccagtc tgaggatgag   660 gctgattatt actgtgcagc atgggatgac agcctgagtg aatttctctt cggaactggg   720
accaagctga ccgtcctagg t                                             741
```

```
<210> SEQ ID NO 47
<211> LENGTH: 137
<212> TYPE: PRT
<213> ORGANISM: Homo sapiens
<220> FEATURE:
<223> OTHER INFORMATION: human mature J chain

<400> SEQUENCE: 47

Gln Glu Asp Glu Arg Ile Val Leu Val Asp Asn Lys Cys Lys Cys Ala
1               5                  10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135
```

```
<210> SEQ ID NO 48
<211> LENGTH: 137
<212> TYPE: PRT
<213> ORGANISM: Artificial sequence
<220> FEATURE:
<223> OTHER INFORMATION: Mutant form of human mature J chain with C134S
      mutation compared to wild type Mature form of human J chain
      (SEQ ID NO:47)

<400> SEQUENCE: 48

Gln Glu Asp Glu Arg Ile Val Leu Val Asp Asn Lys Cys Lys Cys Ala
1               5                  10                  15

Arg Ile Thr Ser Arg Ile Ile Arg Ser Ser Glu Asp Pro Asn Glu Asp
```

```
                    20                  25                  30
Ile Val Glu Arg Asn Ile Arg Ile Val Pro Leu Asn Asn Arg Glu
            35                  40                  45

Asn Ile Ser Asp Pro Thr Ser Pro Leu Arg Thr Arg Phe Val Tyr His
        50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
            115                 120                 125

Leu Thr Pro Asp Ala Ser Tyr Pro Asp
            130                 135

<210> SEQ ID NO 49
<211> LENGTH: 112
<212> TYPE: PRT
<213> ORGANISM: Artificial sequence
<220> FEATURE:
<223> OTHER INFORMATION: Mutant form of human mature J chain with amino
      acids 113-137 deleted compared to wild type Mature form of human J
      chain (SEQ ID NO:47)

<400> SEQUENCE: 49

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Val Pro Leu Asn Asn Arg Glu
            35                  40                  45

Asn Ile Ser Asp Pro Thr Ser Pro Leu Arg Thr Arg Phe Val Tyr His
        50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

<210> SEQ ID NO 50
<211> LENGTH: 137
<212> TYPE: PRT
<213> ORGANISM: Artificial sequence
<220> FEATURE:
<223> OTHER INFORMATION: Mutant form of human mature J chain with C109S
      and C134S mutation compared to wild type mature form of human J
      chain (SEQ ID NO:47)

<400> SEQUENCE: 50

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Val Pro Leu Asn Asn Arg Glu
            35                  40                  45

Asn Ile Ser Asp Pro Thr Ser Pro Leu Arg Thr Arg Phe Val Tyr His
        50                  55                  60
```

```
Leu Ser Asp Leu Cys Lys Lys Cys Asp Pro Thr Glu Val Glu Leu Asp
 65              70                  75                  80

Asn Gln Ile Val Thr Ala Thr Gln Ser Asn Ile Cys Asp Glu Asp Ser
                 85                  90                  95

Ala Thr Glu Thr Cys Tyr Thr Tyr Asp Arg Asn Lys Ser Tyr Thr Ala
            100                 105                 110

Val Val Pro Leu Val Tyr Gly Gly Glu Thr Lys Met Val Glu Thr Ala
            115             120                 125

Leu Thr Pro Asp Ala Ser Tyr Pro Asp
    130             135
```

ANTIBODIES AGAINST C3A RECEPTOR

CROSS REFERENCE TO RELATED APPLICATIONS

This application is a continuation-in-part of International Application No. PCT/US2003/023826, filed Jul. 31, 2003, which claims the benefit of U.S. Provisional Application No. 60/400,057, filed Aug. 2, 2002.

BACKGROUND OF THE INVENTION

The present invention relates to antibodies and related molecules that specifically bind to C3a Receptor. Such antibodies have uses, for example, in the prevention and treatment of asthma, allergy, inflammatory and immune disorders. The invention also relates to nucleic acid molecules encoding anti-C3a Receptor antibodies, vectors and host cells containing these nucleic acids, and methods for producing the same. The present invention relates to methods and compositions for preventing, detecting, diagnosing, treating or ameliorating a disease or disorder, especially asthma, allergy, inflammatory and immune disorders, comprising administering to an animal, preferably a human, an effective amount of one or more antibodies or fragments or variants thereof, or related molecules, that specifically bind to C3a Receptor.

Activation of the complement cascade results in the generation of proinflammatory mediators such as the anaphylotoxins C3a, C4a and C5a. The receptor for C3a is a seven transmembrane G protein coupled receptor protein. The C3a Receptor shares 40% homology with C5a Receptor. The C3a Receptor also contains an unusually large second extracellular loop between transmembrane segments 4 and 5, which contains the major binding site for C3a. A large portion of the second extracellular loop may be mutated without affecting C3a function at the receptor. This data coupled with the knowledge that the second extracellular loop is conserved across species leaves open the possibility that there may be another as yet unidentified ligand for C3a (Chao et al., (1999) *J. Biol. Chem.* 274 9721-9728). C3aR is expressed predominantly on granulocytes and monocytes, but has also been found in lung, spleen, heart, placenta, spinal cord and brain, suggesting an important role in inflammatory reactions in tissues. High levels of expression are found on eosinophils and the mast cell line HMC-1. C3a Receptor expression is also expressed on airway smooth muscle cells. C3a is known to activate and induce chemotaxis of human eosinophils and mast cells (Daffern, P. J. et al., (1995) *J. Exp. Med.* 181:2119-2127; Nilsson, G. et al., (1996) *J. Immunol.* 1693-1698; and Stimler-Gerard, N. P., and Galli, S. J., (1987) *J. Immunol.* 138:1908-13) as well as to induce contraction of human lung parenchymal strips (Stimler, N. P. et al, *Platelet Activating Factor*, eds. Benveniste, J. and Amoux, B. Elsevier, Amsterdam, 1983 pp. 195-203).

Expression of C3a Receptor in airway smooth muscle cells and on cells associated with allergic responses, suggested that c3A receptor may be involved in the pathophysiology of asthma and allergy. Asthma is a chronic inflammatory disease of the airways and lung mucosa with a strong correlation to atopy and acquired (IgE) immunity. However, many features of bronchial asthma, such as smooth muscle contraction, mucus secretion and recruitment of inflammatory cells, are consistent with the actions of complement anaphylatoxins, in particular C3a and C5a. The anaphylatoxins C3a and C5a are liberated as activation byproducts and are potent pro-inflammatory mediators that bind to specific cell surface receptors and cause leukocyte activation, smooth muscle contraction and vascular permeability. Genetic deletion of the C3a Receptor protects against the changes in lung physiology seen after allergen challenge. Furthermore, human asthmatics develop significant levels of C3a following intra-pulmonary deposition of allergen, but not saline. (Humbles et al., (2000) *Nature* 406:998-1001).

Because of the involvement of the C3a Receptor in the promotion of the asthmatic response and other allergic and inflammatory responses in general, there is a clear need in the art for agents that can be used to monitor the expression of C3a Receptor and/or modulate the biological activities of C3a Receptor.

SUMMARY OF THE INVENTION

The present invention encompasses antibodies (including molecules comprising, or alternatively consisting of, antibody fragments or variants thereof) that specifically bind to a C3a Receptor polypeptide or polypeptide fragment or variant of a C3a Receptor. In particular, the invention encompasses antibodies (including molecules comprising, or alternatively consisting of, antibody fragments or variants thereof) that specifically bind to a polypeptide or polypeptide fragment or variant of human C3a Receptor such as those of SEQ ID NO:2.

In addition, the present invention encompasses antibodies (including molecules comprising, or alternatively consisting of, antibody fragments or variants thereof) that specifically bind to a C3a Receptor polypeptide or polypeptide fragment or variant of a C3a Receptor as expressed on the surface of a cell.

The present invention relates to methods and compositions for preventing, treating or ameliorating a disease or disorder comprising administering to an animal, preferably a human, an effective amount of one or more antibodies or fragments or variants thereof, or related molecules, that specifically bind to a C3a Receptor polypeptide or a fragment or variant thereof. In specific embodiments, the present invention relates to methods and compositions for preventing, treating or ameliorating a disease or disorder associated with aberrant C3a Receptor function or expression, comprising administering to an animal, preferably a human, an effective amount of one or more antibodies or fragments or variants thereof, or related molecules, that specifically bind to a C3a Receptor polypeptide or a fragment or variant thereof. In preferred embodiments, the present invention relates to antibody-based methods and compositions for preventing, treating or ameliorating inflammatory disorders or conditions associated with inflammatory disorders. In specific preferred embodiments, the present invention relates to antibody based methods and compositions for preventing, treating or ameliorating asthma and conditions associated with asthma. In specific highly preferred embodiments, the present invention also relates to antibody based methods and compositions for preventing, treating or ameliorating allergy and conditions associated with allergy.

Other diseases, disorders or conditions that may be treated, prevented or ameliorated with the antibodies of the invention include, but are not limited to, autoimmune disorders such as rheumatoid arthritis and systemic lupus erythematosus; arthritis; immunological hypersensitivities; physical trauma; organ transplant rejection; infectious diseases cardiovascular disorders and/or proliferative disorders.

The present invention also encompasses methods and compositions for detecting, diagnosing, or prognosing diseases or disorders comprising administering to an animal, preferably a human, an effective amount of one or more antagonistic antibodies or fragments or variants thereof, or related molecules, that specifically bind to a C3a Receptor or a fragment or variant thereof.

In specific highly preferred embodiments, the present invention also encompasses methods of inhibiting eosinophil and/or mast cell activation, comprising administering to an animal, preferably a human, an effective amount of one or more antibodies or fragments or variants thereof, or related molecules, that specifically bind to a C3a Receptor or a fragment or variant thereof.

In specific embodiments, the present invention encompasses methods of inhibiting chemotaxis of eosinophils and/or mast cells, comprising administering to an animal, preferably a human, an effective amount of one or more antibodies or fragments or variants thereof, or related molecules, that specifically bind to a C3a Receptor or a fragment or variant thereof.

In specific embodiments, the present invention also encompasses methods of inhibiting chemotaxis of cells of the immune system, such as basophils, comprising administering to an animal, preferably a human, an effective amount of one or more antagonistic antibodies or fragments or variants thereof, or related molecules, that specifically bind to a C3a Receptor or a fragment or variant thereof.

In specific highly preferred embodiments, the present invention also encompasses methods of inhibiting mast cell activation, comprising contacting a mast cell with one or more antagonistic antibodies or fragments or variants thereof, or related molecules, that specifically bind to a C3a Receptor or a fragment or variant thereof.

In additional embodiments, the present invention encompasses methods and compositions for detecting, diagnosing, or prognosing diseases or disorders associated with aberrant C3a or C3a Receptor function or expression, comprising administering to an animal, preferably a human, an effective amount of one or more antibodies or fragments or variants thereof, or related molecules, that specifically bind to a C3a Receptor or a fragment or variant thereof. In preferred embodiments, the present invention relates to antibody-based methods and compositions for detecting, diagnosing, or treating or ameliorating inflammatory disorders or conditions associated with inflammatory disorders. Other diseases and disorders which can be treated, prevented or ameliorated with the antibodies of the invention include, but are not limited to, autoimmune disorders such as rheumatoid arthritis and systemic lupus erythematosus; arthritis; immunological hypersensitivities; physical trauma; organ transplant rejection; infectious diseases cardiovascular disorders and/or proliferative disorders.

Another embodiment of the present invention includes the use of the antibodies of the invention as a diagnostic tool to monitor the expression of C3a Receptor expression on cells.

The present inventors have generated antibodies that specifically bind C3a Receptor polypeptides (SEQ ID NO:2). The invention encompasses the cell lines expressing these antibodies, listed in Table 1. In addition the invention encompasses cell lines engineered to express antibodies corresponding to these antibodies which are deposited with the American Type Culture Collection ("ATCC") as of the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the International Recognition of the Deposit of Microorganisms For Purposes of Patent Procedure.

Further, the present invention encompasses polynucleotides encoding the antibodies, as well as the amino acid sequences of the antibodies. Molecules comprising, or alternatively consisting of, fragments or variants of these antibodies (e.g., VH domains, VH CDRs, VL domains, or VL CDRs having an amino acid sequence of any one of the antibodies referred to in Table 1), that specifically bind to C3a Receptor polypeptides or fragments or variants thereof are also encompassed by the invention, as are nucleic acid molecules that encode these antibodies and/or molecules. In highly preferred embodiments, the present invention encompasses antibodies, or fragments or variants thereof, that bind to the mature form of the C3a Receptor polypeptide (or fragments and variants thereof).

The present invention also provides anti-C3a Receptor antibodies that are coupled to a detectable label, such as an enzyme, a fluorescent label, a luminescent label, or a bioluminescent label. The present invention also provides anti-C3a Receptor antibodies that are coupled to a therapeutic or cytotoxic agent. The present invention also provides anti-C3a Receptor antibodies that are coupled to a radioactive material, directly or indirectly.

The present invention further provides antibodies that inhibit or abolish C3a Receptor activity. In highly preferred embodiments of the present invention, anti-C3a Receptor antibodies of the present invention are used to treat, prevent or ameliorate asthma and/or conditions associated with asthma. In other highly preferred embodiments, anti-C3a Receptor antibodies of the present invention are administered to an individual alone or in combination with other therapeutic compounds to treat, prevent or ameliorate asthma.

The present invention also provides antibodies that bind one or more C3a Receptor polypeptides that act as either C3a Receptor agonists or C3a Receptor antagonists. In other specific embodiments, the antibodies of the invention downregulate or inhibit C3a Receptor expression.

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs).

The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (ie., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

DETAILED DESCRIPTION OF THE INVENTION

Definitions

The term "antibody," as used herein, refers to immunoglobulin molecules and immunologically active portions of immunoglobulin molecules, ie., molecules that contain an antigen binding site that specifically binds an antigen. As such, the term antibody encompasses not only whole antibody molecules, but also antibody multimers, antibody fragments as well as variants (including derivatives) of antibodies, antibody multimers, and antibody fragments. Examples of molecules which are described by the term "antibody" herein include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody. Antibodies that specifically bind to C3a Receptor may have cross-reactivity with other antigens. Preferably, antibodies that specifically bind to C3a Receptor do not cross-react with other antigens. Antibodies that specifically bind to C3a Receptor can be identified, for example, by immunoassays or other techniques known to those of skill in the art, e.g., the immunoassays described in the Examples below.

Antibodies of the invention include, but are not limited to, monoclonal, multispecific, human or chimeric antibodies, single chain antibodies, Fab fragments, F(ab') fragments, anti-idiotypic (anti-Id) antibodies (including, eg., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. Preferably, an antibody of the invention comprises, or alternatively consists of, a VH domain, VH CDR, VL domain, or VL CDR having an amino acid sequence of any one of those referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers withon an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the J chain polypeptide (SEQ ID NO:47). Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31 and Frigerio et al., (2000) Plant Physiology 123:1483-94., both of which are hereby incorporated by reference in their entireties), IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to to contain a J chain interaction domain) is not desired, it can be greatly reduced by expressing the antibody molecule in association with a mutant J chain that does not interact well with pIgR (e.g., SEQ ID NOS:48-50). Expression of an antibody with one of these mutant J chains will reduce its ability to bind to the polymeric IgA receptor on epithelial cells, thereby reducing transport of the antibody across the epithelial cell and its resultant secretion into the lumen of mucosa lined organs. ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

By "isolated antibody" is intended an antibody removed from its native environment. Thus, an antibody produced, purified from and/or contained within a hybridoma and/or recombinant host cell is considered isolated for purposes of the present invention.

Unless otherwise defined in the specification, specific binding by an antibody to C3a Receptor means that an antibody binds C3a Receptor but does not significantly bind to (i.e., cross react with) proteins other than C3a Receptor, such as other proteins in the same family of proteins). An antibody that binds C3a Receptor protein and does not cross-react with other proteins is not necessarily an antibody that does not bind said other proteins in all conditions; rather, the C3a Receptor-specific antibody of the invention preferentially binds C3a Receptor compared to its ability to bind said other proteins such that it will be suitable for use in at least one type of assay or treatment, e.g., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that C3a Receptor-specific antibodies bind to epitopes of C3a Receptor, an antibody that specifically binds C3a Receptor may or may not bind fragments of C3a Receptor and/or variants of C3a Receptor (e.g., proteins that are at least 90% identical to C3a Receptor) depending on the presence or absence of the epitope bound by a given C3a Receptor-specific antibody in the C3a Receptor fragment or variant. Likewise, C3a Receptor-specific antibodies of the invention may bind species orthologues of C3a Receptor (including fragments thereof) depending on the presence or absence of the epitope recognized by the antibody in the orthologue. Additionally, C3a Receptor-specific antibodies of the invention may bind modified forms of C3a Receptor, for example, C3a Receptor fusion proteins. In such a case when antibodies of the invention bind C3a Receptor fusion proteins, the antibody must make binding contact with the C3a Receptor moiety of the fusion protein in order for the binding to be specific. Antibodies that specifically bind to C3a Receptor can be identified, for example, by immunoassays or other techniques known to those of skill in the art, e.g., the immunoassays described in the Examples below.

The term "variant" as used herein refers to a polypeptide that possesses a similar or identical amino acid sequence as a C3a Receptor polypeptide, a fragment of a C3a Receptor polypeptide, an anti-C3a Receptor antibody and/or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a C3a Receptor polypeptide, or a fragment thereof, an anti-C3a Receptor antibody or antibody fragment thereof (including a VH domain, VHCDR, VL domain, or VLCDR having an amino acid sequence referred to in Table 1) described herein; (b) a polypeptide encoded by a nucleotide sequence, the complementary sequence of which hybridizes under stringent conditions to a nucleotide sequence encoding a C3a Receptor polypeptide (e.g., SEQ ID NO:2), a fragment of a C3a Receptor polypeptide, an anti-C3a Receptor antibody or antibody fragment thereof (including a VH domain, VHCDR, VL domain, or VLCDR having an amino acid sequence of any one of those referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding a C3a Receptor polypeptide, a fragment of a C3a Receptor polypeptide, an anti-C3a Receptor antibody or antibody fragment thereof (including a VH domain, VHCDR, VL domain, or VLCDR having an amino acid sequence referred to in Table 1), described herein. Preferably, a variant C3a Receptor polypeptide, a variant fragment of a C3a Receptor polypeptide, or a variant anti-C3a Receptor antibody and/or antibody fragment possesses similar or identical function and/or structure as the reference C3a Receptor polypeptide, the reference fragment of a C3a Receptor polypeptide, or the reference anti-C3a Receptor antibody and/or antibody fragment, respectively.

A polypeptide with similar structure to a C3a Receptor polypeptide, a fragment of a C3a Receptor polypeptide, an anti-C3a Receptor antibody or antibody fragment thereof, described herein refers to a polypeptide that has a similar secondary, tertiary or quaternary structure of a C3a Receptor polypeptide, a fragment of a C3a Receptor polypeptide, an anti-C3a Receptor antibody, or antibody fragment thereof, described herein. The structure of a polypeptide can determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl Acad. Sci. USA* 87:2264-2268(1990), modified as in Karlin and Altschul *Proc. Natl. Acad. Sci. USA* 90:5873-5877(1993). The BLASTn and BLASTx programs of Altschul, et al. *J. Mol. Biol.* 215:403-410(1990) have incorporated such an alogrithm. BLAST nucleotide searches can be performed with the BLASTn program (score=100, wordlength=12) to obtain nucleotide sequences homologous to a nucleic acid molecules of the invention. BLAST protein searches can be performed with the BLASTx program (score=50, wordlength=3) to obtain amino acid sequences homologous to a protein molecules of the invention. To obtain gapped alignment for comparison purposes, Gapped BLAST can be utilized as described in Altschul et al. *Nucleic Acids Res.* 25:3589-3402(1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used.

Another example of a mathematical algorithm utilized for the comparison of sequences is the algorithm of Myers and Miller, CABIOS (1989). The ALIGN program (version 2.0) which is part of the GCG sequence alignment software package has incorporated such an alogrithm. Other algorithms for sequence analysis known in the art include ADVANCE and ADAM as described in Torellis and Robotti *Comput. Appl. Biosci.*, 10 :3-5(1994); and FASTA described in Pearson and Lipman *Proc. Natl. Acad. Sci.* 85:2444-8(1988). Within FASTA, ktup is a control option that sets the sensitivity and speed of the search.

The term "derivative" as used herein, refers to a variant polypeptide of the invention that comprises, or alternatively consists of, an amino acid sequence of a C3a Receptor polypeptide, a fragment of a C3a Receptor polypeptide, or an antibody of the invention that specifically binds to a C3a Receptor polypeptide, which has been altered by the introduction of amino acid residue substitutions, deletions or additions. The term "derivative" as used herein also refers to a C3a Receptor polypeptide, a fragment of a C3a Receptor polypeptide, or an antibody that specifically binds to a C3a Receptor polypeptide which has been modified, e.g., by the covalent attachment of any type of molecule to the polypeptide. For example, but not by way of limitation, a C3a Receptor polypeptide, a fragment of a C3a Receptor polypeptide, or an anti-C3a Receptor antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a C3a Receptor polypeptide, a fragment of a C3a Receptor polypeptide, or an anti-C3a Receptor antibody, may be modified by chemical modifications using techniques known to those of skill in the art, including, but not limited to, specific chemical cleavage, acetylation, formylation, metabolic synthesis of tunicamycin, etc. Further, a derivative of a C3a Receptor polypeptide, a fragment of a C3a Receptor polypeptide, or an anti-C3a Receptor antibody, may contain one or more non-classical amino acids. A polypeptide derivative possesses a similar or identical function as a C3a Receptor polypeptide, a fragment of a C3a Receptor polypeptide, or an anti-C3a Receptor antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino acid residues, at least 70 amino acid residues, at least 80 amino acid residues, at least 90 amino acid residues, or at least 100 amino acid residues of the amino acid sequence of C3a Receptor, or an anti-C3a Receptor antibody (including molecules such as scFv's, that comprise, or alternatively consist of, antibody fragments or variants thereof) that specifically binds to C3a Receptor.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

As used herein the phrase "splice variant" refers to cDNA molecules produced from a RNA molecules initially transcribed from the same genomic DNA sequence which have undergone alternative RNA splicing. Alternative RNA splicing occurs when a primary RNA transcript undergoes splicing, generally for the removal of introns, which results in the production of more than one mRNA molecule each of which may encode different amino acid sequences. The term "splice variant" also refers to the proteins encoded by the above cDNA molecules.

Herein, "C3a Receptor proteins" and "C3a Receptor polypeptides" may refer to not only to the protein of SEQ ID NO:2, but also to fragments and variants of the protein of SEQ ID NO:2, as well as proteins resulting from the alternate splicing of the genomic DNA sequences encoding proteins having regions of amino acid sequence identity and C3a Receptor activity which correspond to the protein of SEQ ID NO:2 as well as C3a Receptor allelic variants.

Herein, the phrase "antibody compositions" includes antibodies of the invention (including fragments and variants thereof) as well as polynucleotides encoding antibodies of the invention. The antibodies and polynucleotide may be associated (covalently or non-covalently) with heterologous amino acid or nucleotide sequences, respectively. In addition, antibody compositions may include other therapeutic or diagnostic agents, such as those described herein.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamuna, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J Mol. Biol.* 196: 901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547 1553 (1992). In addition, bispecific antibodies may be formed as "diabodies" (Holliger et al. "Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int J Cancer Suppl* 7:51-52(1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

fragments or variants thereof) that specifically bind to a polypeptide or a polypeptide fragment of C3a Receptor. In particular, the invention provides antibodies corresponding to the scFvs referred to in Table 1, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule.

Cell lines that express IgG1 antibodies that comprise the VH and VL domains of scFvs of the invention have been deposited with the American Type Culture Collection ("ATCC") on the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the International Recognition of the Deposit of Microorganisms for Purposes of Patent Procedure.

Accordingly, in one embodiment, the invention provides antibodies that comprise the VH and VL domains of scFvs of the invention.

In a preferred embodiment, an antibody of the invention is an antibody expressed by any one of the cell lines disclosed in Table 1.

Table 1 defines the SEQ ID NOS corresponding to the amino acid sequences of the VH and VL domains of the scFvs. Table 1 further defines the amino acid residues within the corresponding SEQ ID NOS that make up the various VH CDR and VL CDR regions of the scFvs.

TABLE 1

| scFv | scFv Protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 |
|---|---|---|---|---|---|---|---|---|---|---|
| D098G01 | 43 | 45 | 1-125 | 26-35 | 50-66 | 99-114 | 142-257 | 164-177 | 194-203 | 238-246 |
| D185G07 | 44 | 46 | 1-121 | 26-35 | 50-66 | 99-110 | 137-247 | 159-171 | 187-193 | 226-236 |

Anti-C3a Receptor Antibodies

Using phage display technology, single chain antibody molecules ("scFvs") have been identified that specifically bind to C3a Receptor (or fragments or variants thereof). Molecules comprising, or alternatively consisting of, fragments or variants of these scFvs (e.g., including a VH domain, VHCDR, VL domain, or VLCDR having an amino acid sequence of the corresponding portion of any one or more scFvs referred to in Table 1), that specifically bind to C3a Receptor (or fragments or variants thereof) are also encompassed by the invention, as are nucleic acid molecules that encode these scFvs, and/or molecules.

In particular, the invention relates to scFvs comprising, or alternatively consisting of the amino acid sequence of any one of SEQ ID NOs:43 and 44, referred to in Table 1 below. Molecules comprising, or alternatively consisting of, fragments or variants (e.g., including VH domains, VH CDRs, VL domains, or VL CDRs identified in Table 1) of the scFvs referred to in Table 1, that specifically bind to C3a Receptor are also encompassed by the invention, as are nucleic acid molecules that encode these scFvs, and/or molecules (e.g., SEQ ID NOs:45 and 46).

The present invention provides antibodies (including molecules comprising, or alternatively consisting of, antibody The present invention encompasses antibodies (including molecules comprising, or alternatively consisting of, antibody fragments or variants thereof) that specifically bind to a C3a Receptor polypeptide or a fragment, variant, or fusion protein thereof. A C3a Receptor polypeptide includes, but is not limited to, C3a Receptor (SEQ ID NO:2) or the polypeptide encoded by the cDNA contained in ATCC Deposit No. 75982 on Aug. 21, 1997. C3a Receptor may be produced through recombinant expression of nucleic acids encoding the polypeptide of SEQ ID NO:2 (e.g., the cDNA in the ATCC Deposit Number 75982). Antibodies of the invention may specifically bind C3a Receptor as well as fragments and variants thereof, and are described in more detail below.

C3a Receptor Polypeptides

In certain embodiments of the present invention, the antibodies of the present invention bind C3a Receptor polypeptide, or fragments or variants thereof. The following section describes the C3a Receptor polypeptides, fragments and variants that may be bound by the antibodies of the invention in more detail. C3a Receptor is also described in United States Application Publication Number US20030022130 and International Publication Number WO96/25432, which are herein incorporated by reference in their entireties.

In certain embodiments, the antibodies of the present invention specifically bind C3a Receptor polypeptide. An antibody that specifically binds C3a Receptor may, in some embodiments, bind fragments, variants (including species orthologs and allelic variants of C3a Receptor), multimers or modified forms of C3a Receptor. For example, an antibody specific for C3a Receptor may bind the C3a Receptor moiety of a fusion protein comprising all or a portion of C3a Receptor.

Antibodies that bind C3a Receptor polypeptides may bind them as isolated polypeptides or in their naturally occurring state. For, example antibodies of the present invention may bind recombinantly produced C3a Receptor polypeptides. In a specific embodiment, antibodies of the present invention bind a C3a Receptor polypeptide purified from a cell culture wherein the cells in said cell culture comprise a polynucleotide encoding amino acids 1 to 482 of SEQ ID NO:2 operably associated with a regulatory sequence that controls expression of said polynucleotide. Antibodies of the present invention may also bind C3a Receptor expressed on the surface of a cell, wherein said C3a Receptor is encoded by a polynucleotide encoding amino acids 1 to 482 of SEQ ID NO:2 operably associated with a regulatory sequence that controls expression of said polynucleotide.

Antibodies of the present invention may bind C3a Receptor polypeptide fragments comprising or alternatively, consisting of, the amino acid sequence of SEQ ID NO:2, encoded by the cDNA contained in ATCC Deposit Number 75982, or encoded by nucleic acids which hybridize (e.g., under stringent hybridization conditions) to the nucleotide sequence contained in ATCC deposit Number 75982, or the complementary strand thereto. Protein fragments may be "freestanding", or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 23, 24 to 43, 44 to 63, 64 to 83 and/or 84 to 104, 105 to 125, 126-150, 151 to 175, 176 to 200, 201 to 225, 2226 to 250, 251 to 275, 276 to 300, 301 to 325, 326 to 350, 351 to 375, 376 to 400, 401 to 425, 426 to 450, 451 to 875, 476 to 482 of SEQ ID NO:2. In this context "about" includes the particularly recited value, larger or smaller by several (5, 4, 3, 2, or 1) amino acids, at either extreme or at both extremes. Moreover, polypeptide fragments bound by the antibodies of the invention can be at least about 10, 20, 30, 40, 50, 60, 70, 80, 90, or 100 amino acids in length. In this context "about" includes the particularly recited value, larger or smaller by several (5, 4, 3, 2, or 1) amino acids, at either extreme or at both extremes.

Preferably, antibodies of the present invention bind polypeptide fragments selected from the group: a polypeptide comprising or alternatively, consisting of, a fragment of the predicted mature C3a Receptor polypeptide, wherein the fragment has a C3a Receptor functional activity (e.g., antigenic activity or biological activity); and a polypeptide comprising, or alternatively, consisting of, one, two, three, four or more, epitope bearing portions of the C3a Receptor protein. In additional embodiments, the polypeptide fragments of the invention comprise, or alternatively, consist of, any combination of 1, 2, 3, 4, or all 5 of the above members. The amino acid residues constituting the preferred epitopes have been predicted by computer analysis. Thus, as one of ordinary skill would appreciate, the amino acid residues constituting these domains may vary slightly (e.g., by about 1 to about 15 amino acid residues) depending on the criteria used to define each epitope. Polynucleotides encoding these polypeptides are also encompassed by the invention.

In another preferred embodiment, antibodies of the present invention bind C3a Receptor polypeptides comprising, or alternatively consisting of, the expressed and/or mature polypeptide of C3a Receptor (amino acid residues 1-1482 of SEQ ID NO:2). In highly preferred embodiments, the antibodies of the invention that bind all or a portion of the mature C3a Receptor polypeptide inhibit C3a Receptor-induced biological activities (e.g., constriction of airway smooth muscle; activation, chemotaxis/and or degranulation of granulocytes and/or mast cells) in the C3a Receptor expressing cells (e.g., airway smooth muscle cells, mast cells and granulocytes such as eosinophils).

In another embodiment, antibodies of the present invention bind C3a Receptor polypeptides comprising, or alternatively consisting of, the extracellular domains of C3a Receptor (e.g., amino acid residues 1-21, 84-96, 162-332, and 404-416 in SEQ IN NO:2). In a preferred embodiment, antibodies of the present invention bind C3a Receptor polypeptides comprising, or alternatively consisting of, the second extracellular loop of C3a Receptor (amino acid residues 162-332 in SEQ ID NO:2). In another preferred embodiment, antibodies of the present invention bind C3a Receptor polypeptides comprising, or alternatively consisting of, amino acid residues 162-183 or 308-332 in SEQ ID NO:2. In another preferred embodiment, antibodies of the present invention bind C3a Receptor polypeptides comprising, or alternatively consisting of, amino acid residues 161-186 or 309-341 in SEQ ID NO:2 and inhibit or abolish C3a binding to C3a receptor.

In another embodiment, antibodies of the present invention bind C3a Receptor polypeptides comprising, or alternatively consisting of, a transmembrane domain (e.g., amino acid residues 22-50, 58-83, 97-118, 138-161, 333-361, 378-403, 417-440 in SEQ ID NO:2) or an intracellular domain (e.g., amino acid residues 51-57, 119-137, 362-377, 441-482 in SEQ ID NO:2).

Antibodies of the invention may also bind fragments comprising, or alternatively, consisting of, structural or functional attributes of C3a Receptor. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) C3a Receptor. Certain preferred regions are those set out in Table 2 and include, but are not limited to, regions of the aforementioned types identified by analysis of the amino acid sequence depicted in (SEQ ID NO:2), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs.

The data representing the structural or functional attributes of C3a Receptor set forth in Table 2, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column III represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions; Column VIII represents a Kyte-Doolittle hydrophilicity plot; Column; Column IX represents a Hopp-Woods hydrophobicity plot; Column IX represents the results of an Eisenberg analysis of alpha amphipathic regions; Column X represents the results of an Eisenberg analysis of beta amphipathic regions; Column XI represents the results of a Karplus-Schultz analysis of flexible regions; Column XII represents the Jameson-Wolf antigenic index score; and Column XIII represents the Emini surface probability plot.

In a preferred embodiment, the data presented in columns VIII, XII, and XII of Table 2 can be used to determine regions of C3a Receptor which exhibit a high degree of potential for antigenicity. Regions of high antigenicity are determined from the data presented in columns VIII, XII, and XII by choosing values which represent regions of the polypeptide which are likely to be exposed on the surface of the polypeptide in an environment in which antigen recognition may occur in the process of initiation of an immune response.

The above-mentioned preferred regions set out in Table 2 include, but are not limited to, regions of the aforementioned types identified by analysis of the amino acid sequence set out in SEQ ID NO:2. As set out in Table 2, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Among preferred polypeptide fragments bound by one or more antibodies of the invention are those that comprise regions of C3a Receptor that combine several structural features, such as several (e.g., 1, 2, 3, or 4) of the same or different region features set out above and in Table 2.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | −0.54 | 0.57 | . | . | . | −0.40 | 0.43 |
| Ala | 2 | . | . | B | . | . | . | . | −0.74 | 0.53 | . | * | . | −0.40 | 0.46 |
| Ser | 3 | . | . | B | . | . | . | . | −0.36 | 0.60 | . | * | . | −0.40 | 0.36 |
| Phe | 4 | . | . | B | . | . | . | . | −0.28 | 0.17 | . | * | . | −0.10 | 0.63 |
| Ser | 5 | . | . | B | . | . | . | . | 0.11 | 0.04 | . | * | . | −0.10 | 0.90 |
| Ala | 6 | . | . | . | . | . | . | C | 0.41 | −0.06 | . | * | F | 1.34 | 1.08 |
| Glu | 7 | . | . | . | . | . | . | C | 0.69 | −0.06 | . | * | F | 1.68 | 1.67 |
| Thr | 8 | . | . | . | . | . | . | C | 0.99 | −0.36 | . | * | F | 2.02 | 1.80 |
| Asn | 9 | . | . | . | . | T | . | . | 0.88 | −0.74 | . | * | F | 2.86 | 2.98 |
| Ser | 10 | . | . | . | . | T | T | . | 0.37 | −0.56 | . | . | F | 3.40 | 1.42 |
| Thr | 11 | . | . | . | . | T | T | . | 0.66 | 0.13 | * | . | F | 2.01 | 0.81 |
| Asp | 12 | . | . | . | . | T | T | . | 0.66 | 0.03 | . | . | F | 1.67 | 0.67 |
| Leu | 13 | . | . | B | . | . | T | . | 0.76 | 0.03 | * | . | F | 0.93 | 0.87 |
| Leu | 14 | . | . | B | . | . | . | . | 0.47 | 0.07 | * | . | F | 0.39 | 0.93 |
| Ser | 15 | . | . | B | . | . | . | . | 0.77 | 0.50 | * | . | F | −0.13 | 0.59 |
| Gln | 16 | . | . | . | . | . | T | C | 1.08 | 0.90 | * | . | F | 0.54 | 1.15 |
| Pro | 17 | . | . | . | . | T | T | . | 0.87 | 0.21 | * | . | F | 1.16 | 2.41 |
| Trp | 18 | . | . | . | . | T | T | . | 1.47 | −0.04 | . | . | F | 1.88 | 2.78 |
| Asn | 19 | . | . | . | . | . | T | C | 1.42 | 0.00 | . | . | F | 1.20 | 2.48 |
| Glu | 20 | . | . | . | . | . | . | C | 0.83 | 0.24 | . | . | F | 0.88 | 1.19 |
| Pro | 21 | . | . | . | B | . | . | C | 0.02 | 0.50 | . | . | F | 0.11 | 0.79 |
| Pro | 22 | . | . | . | B | T | . | . | −0.07 | 0.27 | . | . | F | 0.49 | 0.41 |
| Val | 23 | . | . | B | B | . | . | . | −0.38 | 0.26 | . | . | . | −0.18 | 0.32 |
| Ile | 24 | . | . | B | B | . | . | . | −1.23 | 0.87 | . | . | . | −0.60 | 0.20 |
| Leu | 25 | . | . | B | B | . | . | . | −2.12 | 1.09 | . | . | . | −0.60 | 0.10 |
| Ser | 26 | . | . | B | B | . | . | . | −2.72 | 1.34 | . | . | . | −0.60 | 0.09 |
| Met | 27 | . | . | B | B | . | . | . | −2.81 | 1.39 | . | . | . | −0.60 | 0.11 |
| Val | 28 | . | . | B | B | . | . | . | −2.77 | 1.09 | . | . | . | −0.60 | 0.17 |
| Ile | 29 | . | . | B | B | . | . | . | −2.19 | 1.09 | . | * | . | −0.60 | 0.11 |
| Leu | 30 | . | . | B | B | . | . | . | −2.08 | 1.19 | . | . | . | −0.60 | 0.16 |
| Ser | 31 | . | . | B | B | . | . | . | −2.59 | 1.36 | . | * | . | −0.60 | 0.18 |
| Leu | 32 | . | . | B | B | . | . | . | −2.80 | 1.40 | . | . | . | −0.60 | 0.22 |
| Thr | 33 | . | . | B | B | . | . | . | −2.29 | 1.40 | . | * | . | −0.60 | 0.22 |
| Phe | 34 | . | . | B | B | . | . | . | −2.21 | 1.14 | . | * | . | −0.60 | 0.16 |
| Leu | 35 | . | . | B | B | . | . | . | −1.61 | 1.44 | . | * | . | −0.60 | 0.16 |
| Leu | 36 | . | . | B | B | . | . | . | −1.66 | 1.19 | . | * | . | −0.60 | 0.17 |
| Gly | 37 | . | . | B | B | . | . | . | −0.84 | 1.13 | . | * | . | −0.60 | 0.19 |
| Leu | 38 | . | . | . | . | . | T | C | −0.88 | 0.74 | . | . | F | 0.15 | 0.38 |
| Pro | 39 | . | . | . | . | . | T | C | −0.99 | 0.49 | . | * | F | 0.15 | 0.46 |
| Gly | 40 | . | . | . | . | T | T | . | −1.03 | 0.49 | . | . | F | 0.35 | 0.38 |
| Asn | 41 | . | . | . | . | . | T | C | −1.03 | 0.70 | . | * | F | 0.15 | 0.34 |
| Gly | 42 | . | . | B | B | . | . | . | −0.98 | 0.70 | . | . | F | −0.45 | 0.18 |
| Leu | 43 | . | . | B | B | . | . | . | −1.02 | 1.19 | . | . | . | −0.60 | 0.19 |
| Val | 44 | . | . | B | B | . | . | . | −1.40 | 1.40 | . | . | . | −0.60 | 0.09 |
| Leu | 45 | . | . | B | B | . | . | . | −1.40 | 1.50 | . | . | . | −0.60 | 0.09 |
| Trp | 46 | . | . | B | B | . | . | . | −2.21 | 1.50 | . | . | . | −0.60 | 0.11 |
| Val | 47 | . | . | B | B | . | . | . | −1.82 | 1.50 | . | * | . | −0.60 | 0.12 |
| Ala | 48 | . | . | B | B | . | . | . | −1.61 | 0.86 | . | * | . | −0.60 | 0.29 |
| Gly | 49 | . | . | B | B | . | . | . | −0.76 | 0.79 | * | . | . | −0.60 | 0.28 |
| Leu | 50 | . | . | B | . | . | . | . | 0.17 | 0.27 | * | . | . | −0.10 | 0.65 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 51 | . | . | B | . | . | . | . | 0.14 | −0.37 | * | . | . | 0.65 | 1.26 |
| Met | 52 | . | . | B | B | . | . | . | 0.14 | −0.39 | * | * | F | 0.60 | 1.83 |
| Gln | 53 | . | . | B | B | . | . | . | 0.73 | −0.17 | * | * | F | 0.60 | 1.65 |
| Arg | 54 | . | . | B | B | . | . | . | 0.77 | −0.46 | * | . | F | 0.60 | 1.33 |
| Thr | 55 | . | . | B | B | . | . | . | 0.69 | 0.03 | * | * | F | 0.00 | 1.93 |
| Val | 56 | . | . | B | B | . | . | . | 0.36 | 0.10 | * | . | F | −0.15 | 0.78 |
| Asn | 57 | . | . | B | B | . | . | . | 0.26 | 0.61 | * | . | . | −0.60 | 0.42 |
| Thr | 58 | . | . | B | B | . | . | . | −0.56 | 1.40 | * | . | . | −0.60 | 0.25 |
| Ile | 59 | . | . | B | B | . | . | . | −0.70 | 1.60 | * | * | . | −0.60 | 0.28 |
| Trp | 60 | . | . | B | B | . | . | . | −1.20 | 1.46 | . | . | . | −0.60 | 0.24 |
| Phe | 61 | . | . | B | B | . | . | . | −0.66 | 1.74 | . | * | . | −0.60 | 0.14 |
| Leu | 62 | . | . | B | B | . | . | . | −1.47 | 1.74 | . | . | . | −0.60 | 0.28 |
| His | 63 | . | . | B | B | . | . | . | −1.74 | 1.74 | . | . | . | −0.60 | 0.22 |
| Leu | 64 | . | . | B | B | . | . | . | −0.86 | 1.33 | . | . | . | −0.60 | 0.26 |
| Thr | 65 | . | . | . | B | T | . | . | −1.38 | 0.54 | . | . | . | −0.20 | 0.52 |
| Leu | 66 | . | . | . | B | T | . | . | −1.49 | 0.54 | . | . | . | −0.20 | 0.31 |
| Ala | 67 | . | . | . | B | T | . | . | −1.34 | 0.73 | . | . | . | −0.20 | 0.31 |
| Asp | 68 | . | . | B | B | . | . | . | −1.98 | 0.61 | . | . | . | −0.60 | 0.12 |
| Leu | 69 | . | . | B | B | . | . | . | −1.98 | 0.70 | . | . | . | −0.60 | 0.08 |
| Leu | 70 | . | . | B | B | . | . | . | −1.97 | 0.70 | . | * | . | −0.60 | 0.06 |
| Cys | 71 | . | . | B | B | . | . | . | −1.97 | 0.59 | . | * | . | −0.60 | 0.05 |
| Cys | 72 | . | . | B | B | . | . | . | −1.59 | 1.27 | . | * | . | −0.60 | 0.05 |
| Leu | 73 | . | . | B | B | . | . | . | −2.29 | 1.01 | * | * | . | −0.60 | 0.09 |
| Ser | 74 | . | . | B | B | . | . | . | −1.78 | 1.11 | . | * | . | −0.60 | 0.15 |
| Leu | 75 | . | . | B | . | . | T | . | −1.78 | 0.93 | . | * | . | −0.20 | 0.37 |
| Pro | 76 | . | . | B | . | . | T | . | −1.70 | 1.04 | . | * | . | −0.20 | 0.37 |
| Phe | 77 | . | . | B | . | . | T | . | −1.07 | 0.86 | . | * | . | −0.20 | 0.28 |
| Ser | 78 | . | . | B | . | . | T | . | −1.07 | 0.97 | . | * | . | −0.20 | 0.47 |
| Leu | 79 | . | A | B | . | . | . | . | −1.36 | 0.97 | . | * | . | −0.60 | 0.25 |
| Ala | 80 | . | A | B | . | . | . | . | −1.36 | 1.04 | . | * | . | −0.60 | 0.29 |
| His | 81 | . | A | B | . | . | . | . | −1.14 | 0.94 | . | * | . | −0.60 | 0.18 |
| Leu | 82 | . | A | B | . | . | . | . | −0.79 | 0.96 | . | * | . | −0.60 | 0.37 |
| Ala | 83 | . | A | B | . | . | . | . | −0.49 | 0.70 | . | * | . | −0.60 | 0.37 |
| Leu | 84 | . | A | B | . | T | . | . | 0.03 | 0.60 | . | * | . | −0.60 | 0.47 |
| Gln | 85 | . | A | . | . | T | . | . | 0.41 | 1.01 | . | * | F | −0.05 | 0.60 |
| Gly | 86 | . | A | . | . | T | . | . | 0.20 | 0.76 | . | * | F | −0.05 | 0.91 |
| Gln | 87 | . | . | . | . | T | . | . | 0.67 | 1.01 | . | * | F | 0.30 | 1.73 |
| Trp | 88 | . | . | . | . | . | T | C | 1.37 | 0.76 | * | * | . | 0.00 | 0.99 |
| Pro | 89 | . | . | . | . | . | T | C | 1.48 | 0.36 | * | * | . | 0.45 | 1.96 |
| Tyr | 90 | . | . | . | . | T | T | . | 0.67 | 0.71 | * | * | . | 0.20 | 0.98 |
| Gly | 91 | . | . | . | . | T | T | . | 0.34 | 1.00 | * | * | . | 0.20 | 0.77 |
| Arg | 92 | . | . | . | B | T | . | . | 0.39 | 0.66 | * | * | . | −0.20 | 0.27 |
| Phe | 93 | . | . | B | B | . | . | . | −0.13 | 0.23 | * | * | . | −0.30 | 0.34 |
| Leu | 94 | . | . | B | B | . | . | . | −0.81 | 0.16 | * | * | . | −0.30 | 0.28 |
| Cys | 95 | . | . | B | B | . | . | . | −0.78 | 0.41 | * | * | . | −0.60 | 0.10 |
| Lys | 96 | . | . | B | B | . | . | . | −0.73 | 0.84 | * | * | . | −0.60 | 0.18 |
| Leu | 97 | . | . | B | B | . | . | . | −1.73 | 0.44 | * | * | . | −0.60 | 0.29 |
| Ile | 98 | . | . | B | B | . | . | . | −1.92 | 0.44 | * | * | . | −0.60 | 0.38 |
| Pro | 99 | . | . | B | B | . | . | . | −1.97 | 0.56 | * | . | . | −0.60 | 0.13 |
| Ser | 100 | . | . | B | B | . | . | . | −2.11 | 1.20 | * | * | . | −0.60 | 0.12 |
| Ile | 101 | . | . | B | B | . | . | . | −2.16 | 1.20 | . | * | . | −0.60 | 0.14 |
| Ile | 102 | . | . | B | B | . | . | . | −1.94 | 0.91 | . | . | . | −0.60 | 0.15 |
| Val | 103 | . | . | B | B | . | . | . | −1.76 | 1.10 | . | . | . | −0.60 | 0.11 |
| Leu | 104 | . | . | B | B | . | . | . | −2.13 | 1.50 | . | . | . | −0.60 | 0.14 |
| Asn | 105 | . | . | B | B | . | . | . | −2.13 | 1.31 | . | . | . | −0.60 | 0.20 |
| Met | 106 | . | . | B | B | . | . | . | −2.10 | 1.01 | . | * | . | −0.60 | 0.35 |
| Phe | 107 | . | . | B | B | . | . | . | −1.91 | 1.01 | . | * | . | −0.60 | 0.32 |
| Ala | 108 | . | . | B | B | . | . | . | −1.87 | 1.11 | * | . | . | −0.60 | 0.17 |
| Ser | 109 | . | . | B | B | . | . | . | −1.87 | 1.40 | . | . | . | −0.60 | 0.14 |
| Val | 110 | . | . | B | B | . | . | . | −2.18 | 1.47 | . | . | . | −0.60 | 0.14 |
| Phe | 111 | . | . | B | B | . | . | . | −2.17 | 1.17 | . | . | . | −0.60 | 0.19 |
| Leu | 112 | . | . | B | B | . | . | . | −2.36 | 1.17 | . | . | . | −0.60 | 0.15 |
| Leu | 113 | . | . | B | B | . | . | . | −2.07 | 1.47 | . | . | . | −0.60 | 0.14 |
| Thr | 114 | . | . | B | B | . | . | . | −2.58 | 1.21 | . | * | . | −0.60 | 0.21 |
| Ala | 115 | . | . | B | B | . | . | . | −1.72 | 1.11 | . | . | . | −0.60 | 0.21 |
| Ile | 116 | . | . | B | B | . | . | . | −0.91 | 0.43 | * | . | . | −0.60 | 0.43 |
| Ser | 117 | . | . | B | . | . | . | . | −0.77 | −0.26 | . | . | . | 0.50 | 0.59 |
| Leu | 118 | . | . | B | . | . | . | . | −0.77 | −0.17 | . | . | . | 0.50 | 0.31 |
| Asp | 119 | . | . | B | . | . | . | . | −1.31 | 0.01 | . | . | . | −0.10 | 0.37 |
| Arg | 120 | . | . | B | B | . | . | . | −1.58 | −0.03 | * | . | . | 0.30 | 0.20 |
| Cys | 121 | . | . | B | B | . | . | . | −1.39 | 0.23 | * | * | . | −0.30 | 0.18 |
| Leu | 122 | . | . | B | B | . | . | . | −1.04 | 0.33 | * | * | . | −0.30 | 0.09 |
| Val | 123 | . | . | B | B | . | . | . | −0.44 | 0.33 | * | . | . | −0.30 | 0.10 |
| Val | 124 | . | . | B | B | . | . | . | −1.33 | 0.76 | * | * | . | −0.60 | 0.28 |
| Phe | 125 | . | . | B | B | . | . | . | −1.73 | 0.87 | * | * | . | −0.60 | 0.24 |
| Lys | 126 | . | . | B | B | . | . | . | −1.73 | 1.10 | . | . | . | −0.60 | 0.34 |
| Pro | 127 | . | . | . | B | T | . | . | −0.92 | 1.03 | . | . | . | −0.20 | 0.24 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ile | 128 | . | . | . | B | T | . | . | -0.07 | 0.79 | . | . | . | -0.20 | 0.49 |
| Trp | 129 | . | . | B | B | . | . | . | 0.76 | 0.40 | * | . | . | -0.60 | 0.39 |
| Cys | 130 | . | . | B | . | . | T | . | 1.57 | 0.90 | * | . | . | 0.04 | 0.34 |
| Gln | 131 | . | . | . | . | . | T | T | 1.52 | 0.47 | * | . | . | 0.68 | 0.96 |
| Asn | 132 | . | . | . | . | . | T | T | 0.88 | 0.19 | * | . | . | 1.37 | 1.47 |
| His | 133 | . | . | . | . | . | T | T | 1.42 | -0.09 | * | . | . | 2.21 | 2.03 |
| Arg | 134 | . | . | . | . | . | T | . | 1.11 | -0.23 | * | . | F | 2.40 | 1.16 |
| Asn | 135 | . | . | . | . | . | T | T | 1.19 | -0.01 | * | . | . | 2.06 | 0.71 |
| Val | 136 | . | . | . | . | . | T | T | 0.52 | 0.09 | * | . | . | 1.22 | 0.53 |
| Gly | 137 | . | . | . | . | . | T | T | 0.22 | 0.16 | . | . | . | 0.98 | 0.15 |
| Met | 138 | . | . | B | . | . | . | T | -0.63 | 0.54 | * | . | . | 0.04 | 0.12 |
| Ala | 139 | . | . | B | B | . | . | . | -1.41 | 0.83 | * | . | . | -0.60 | 0.11 |
| Cys | 140 | . | . | B | B | . | . | . | -1.76 | 0.76 | . | * | . | -0.60 | 0.06 |
| Ser | 141 | . | . | B | B | . | . | . | -1.57 | 0.76 | . | * | . | -0.60 | 0.06 |
| Ile | 142 | . | . | B | B | . | . | . | -2.11 | 0.71 | . | . | . | -0.60 | 0.03 |
| Cys | 143 | . | . | B | B | . | . | . | -1.80 | 0.90 | . | * | . | -0.60 | 0.04 |
| Gly | 144 | . | . | . | B | T | . | . | -2.07 | 1.24 | . | . | . | -0.20 | 0.03 |
| Cys | 145 | . | . | B | B | . | . | . | -2.26 | 1.50 | . | * | . | -0.60 | 0.04 |
| Ile | 146 | . | . | B | B | . | . | . | -2.54 | 1.46 | . | . | . | -0.60 | 0.05 |
| Trp | 147 | . | . | B | B | . | . | . | -2.32 | 1.39 | . | * | . | -0.60 | 0.05 |
| Val | 148 | . | . | B | B | . | . | . | -2.51 | 1.53 | . | . | . | -0.60 | 0.05 |
| Val | 149 | . | . | B | B | . | . | . | -2.77 | 1.60 | . | . | . | -0.60 | 0.05 |
| Ala | 150 | . | . | B | B | . | . | . | -2.77 | 1.53 | . | . | . | -0.60 | 0.05 |
| Cys | 151 | . | . | B | B | . | . | . | -2.77 | 1.19 | . | . | . | -0.60 | 0.04 |
| Val | 152 | . | . | B | B | . | . | . | -2.69 | 1.23 | . | . | . | -0.60 | 0.03 |
| Met | 153 | . | . | B | B | . | . | . | -2.69 | 1.01 | . | . | . | -0.60 | 0.05 |
| Cys | 154 | . | . | B | B | . | . | . | -2.53 | 1.16 | . | . | . | -0.60 | 0.07 |
| Ile | 155 | . | . | B | B | . | . | . | -2.80 | 1.37 | . | . | . | -0.60 | 0.08 |
| Pro | 156 | . | . | B | B | . | . | . | -2.38 | 1.37 | * | . | . | -0.60 | 0.06 |
| Val | 157 | . | . | B | B | . | . | . | -1.41 | 1.51 | * | . | . | -0.60 | 0.19 |
| Phe | 158 | . | . | B | B | . | . | . | -0.81 | 0.94 | * | . | . | -0.60 | 0.52 |
| Val | 159 | . | . | B | B | . | . | . | -1.03 | 0.26 | * | . | . | -0.30 | 0.58 |
| Tyr | 160 | . | . | B | B | . | . | . | -0.84 | 0.51 | * | . | . | -0.60 | 0.55 |
| Arg | 161 | . | . | B | B | . | . | . | -0.94 | 0.66 | * | . | . | -0.60 | 0.55 |
| Glu | 162 | . | . | B | B | . | . | . | -0.40 | 0.36 | . | . | . | -0.15 | 1.07 |
| Ile | 163 | . | . | B | B | . | . | . | 0.30 | 0.20 | * | . | . | -0.30 | 0.98 |
| Phe | 164 | . | . | B | B | . | . | . | 1.16 | -0.56 | * | . | . | 0.94 | 0.84 |
| Thr | 165 | . | . | . | . | T | T | . | 1.37 | -0.16 | * | . | F | 1.93 | 0.78 |
| Thr | 166 | . | . | . | . | T | T | . | 1.26 | 0.34 | * | * | F | 1.82 | 1.51 |
| Asp | 167 | . | . | . | . | T | T | . | 1.37 | 0.06 | . | * | F | 2.16 | 2.81 |
| Asn | 168 | . | . | . | . | T | T | . | 1.59 | -0.73 | . | . | F | 3.40 | 3.81 |
| His | 169 | . | . | . | . | T | . | . | 1.94 | -0.64 | . | * | F | 2.86 | 1.41 |
| Asn | 170 | . | . | . | . | T | T | . | 2.01 | -0.70 | * | * | . | 2.42 | 0.84 |
| Arg | 171 | . | . | . | . | T | T | . | 2.37 | 0.06 | * | * | . | 1.18 | 0.82 |
| Cys | 172 | . | . | . | . | T | T | . | 1.67 | -0.34 | * | * | . | 1.59 | 1.20 |
| Gly | 173 | . | . | . | . | T | T | . | 1.32 | -0.06 | * | * | . | 1.10 | 0.65 |
| Tyr | 174 | . | . | B | . | . | T | . | 0.54 | -0.03 | * | * | . | 0.70 | 0.33 |
| Lys | 175 | . | . | B | . | . | T | . | 0.24 | 0.66 | * | * | . | -0.20 | 0.50 |
| Phe | 176 | . | . | B | . | . | T | . | -0.17 | 0.47 | * | * | . | -0.03 | 0.68 |
| Gly | 177 | . | . | B | . | . | T | . | 0.20 | 0.43 | . | * | . | 0.14 | 0.58 |
| Leu | 178 | . | . | B | . | . | . | . | -0.27 | 0.06 | . | * | F | 0.56 | 0.39 |
| Ser | 179 | . | . | B | . | . | T | . | -0.02 | 0.74 | . | * | F | 0.63 | 0.37 |
| Ser | 180 | . | . | B | . | . | T | . | -0.31 | -0.04 | . | * | F | 1.70 | 0.63 |
| Ser | 181 | . | . | . | . | . | T | C | 0.18 | 0.29 | . | * | F | 1.28 | 1.19 |
| Leu | 182 | . | . | B | . | . | T | . | 0.52 | 0.03 | . | . | F | 0.91 | 1.37 |
| Asp | 183 | . | . | B | . | . | . | . | 0.63 | -0.36 | . | * | F | 1.14 | 1.71 |
| Tyr | 184 | . | . | B | . | . | T | . | 0.69 | 0.04 | . | . | . | 0.42 | 1.11 |
| Pro | 185 | . | . | B | . | . | T | . | 0.64 | 0.41 | . | * | F | 0.10 | 2.10 |
| Asp | 186 | . | . | . | . | T | T | . | 0.94 | 0.16 | . | * | F | 0.80 | 1.25 |
| Phe | 187 | . | . | B | . | . | T | . | 1.54 | 0.16 | * | . | . | 0.25 | 1.33 |
| Tyr | 188 | . | . | B | . | . | T | . | 0.73 | -0.17 | * | . | . | 0.85 | 1.33 |
| Gly | 189 | . | . | . | . | . | T | C | 0.98 | 0.09 | * | . | F | 0.45 | 0.66 |
| Asp | 190 | . | . | . | . | . | T | C | 1.19 | 0.09 | . | * | F | 0.60 | 1.31 |
| Pro | 191 | . | . | . | . | . | T | C | 1.30 | -0.30 | . | * | F | 1.54 | 1.35 |
| Leu | 192 | . | . | . | . | . | . | C | 1.70 | -1.06 | . | . | F | 1.98 | 2.66 |
| Glu | 193 | . | . | . | B | . | . | . | 1.13 | -1.10 | * | . | . | 2.12 | 2.14 |
| Asn | 194 | . | . | . | . | . | T | C | 1.48 | -0.41 | * | . | F | 2.56 | 1.14 |
| Arg | 195 | . | . | . | . | T | T | . | 1.48 | -0.84 | * | * | F | 3.40 | 2.39 |
| Ser | 196 | . | . | . | . | . | T | C | 0.80 | -1.13 | * | * | F | 2.86 | 2.22 |
| Leu | 197 | . | . | . | . | . | T | C | 0.76 | -0.44 | * | * | F | 2.07 | 0.97 |
| Glu | 198 | . | . | B | . | . | . | . | 0.76 | -0.20 | * | . | . | 1.18 | 0.37 |
| Asn | 199 | . | . | B | . | . | . | . | 0.54 | 0.20 | * | . | . | 0.24 | 0.47 |
| Ile | 200 | . | . | B | . | . | . | . | 0.22 | 0.24 | * | . | . | -0.10 | 0.89 |
| Val | 201 | . | . | B | . | . | . | . | 0.18 | -0.01 | * | . | . | 0.50 | 0.79 |
| Gln | 202 | . | . | B | . | . | . | . | 0.99 | 0.41 | * | * | F | 0.09 | 0.49 |
| Pro | 203 | . | . | . | . | . | T | C | 0.39 | 0.01 | * | * | F | 1.28 | 1.21 |
| Pro | 204 | . | . | . | . | . | T | C | 0.39 | -0.06 | * | . | F | 2.22 | 1.61 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 205 | . | . | . | . | T | T | . | 1.28 | −0.30 | * | * | F | 2.76 | 1.49 |
| Glu | 206 | . | . | . | . | T | T | . | 2.24 | −0.70 | * | * | F | 3.40 | 1.61 |
| Met | 207 | . | . | B | . | . | . | . | 1.43 | −1.13 | * | * | F | 2.46 | 2.05 |
| Asn | 208 | . | . | B | . | . | T | . | 1.64 | −0.87 | * | * | F | 2.62 | 1.70 |
| Asp | 209 | . | . | B | . | . | T | . | 1.64 | −1.30 | * | * | F | 2.58 | 1.64 |
| Arg | 210 | . | . | B | . | . | T | . | 1.69 | −0.87 | . | * | F | 2.54 | 2.57 |
| Leu | 211 | . | . | . | . | . | T | C | 1.39 | −1.10 | . | * | F | 2.70 | 2.14 |
| Asp | 212 | . | . | . | . | . | T | C | 1.29 | −1.11 | . | * | F | 3.00 | 1.72 |
| Pro | 213 | . | . | . | . | . | T | C | 1.29 | −0.33 | . | * | F | 2.25 | 0.76 |
| Ser | 214 | . | . | . | . | T | T | . | 0.98 | 0.07 | . | * | F | 1.98 | 1.59 |
| Ser | 215 | . | . | . | . | . | T | C | 0.87 | −0.13 | . | * | F | 2.36 | 1.38 |
| Phe | 216 | . | . | B | . | . | . | . | 1.68 | 0.27 | . | . | F | 1.34 | 1.43 |
| Gln | 217 | . | . | B | . | . | . | . | 1.64 | −0.16 | . | . | F | 2.12 | 1.79 |
| Thr | 218 | . | . | . | . | T | T | . | 1.64 | −0.04 | . | . | F | 2.80 | 1.81 |
| Asn | 219 | . | . | . | . | T | T | . | 1.66 | 0.00 | . | . | F | 1.92 | 3.24 |
| Asp | 220 | . | . | . | . | T | T | . | 1.64 | 0.13 | . | * | F | 1.64 | 1.97 |
| His | 221 | . | . | . | . | . | T | C | 1.49 | 0.21 | . | * | F | 1.16 | 1.97 |
| Pro | 222 | . | . | . | . | T | T | . | 1.28 | 0.37 | . | . | . | 0.78 | 0.91 |
| Trp | 223 | . | . | . | . | T | T | . | 1.28 | 0.40 | . | . | . | 0.20 | 0.84 |
| Thr | 224 | . | . | B | . | . | T | . | 0.42 | 0.89 | . | . | . | −0.20 | 0.89 |
| Val | 225 | . | . | B | B | . | . | . | −0.28 | 1.03 | * | * | . | −0.60 | 0.43 |
| Pro | 226 | . | . | B | B | . | . | . | −0.24 | 1.39 | . | . | . | −0.60 | 0.35 |
| Thr | 227 | . | . | B | B | . | . | . | −0.24 | 0.87 | . | * | . | −0.60 | 0.42 |
| Val | 228 | . | . | B | B | . | . | . | 0.04 | 0.81 | . | * | . | −0.60 | 0.88 |
| Phe | 229 | . | . | B | B | . | . | . | 0.04 | 0.57 | . | . | . | −0.60 | 0.99 |
| Gln | 230 | . | . | B | B | . | . | . | 0.20 | 0.63 | . | . | F | −0.45 | 0.99 |
| Pro | 231 | . | . | B | B | . | . | . | 0.41 | 0.93 | . | . | F | −0.30 | 1.15 |
| Gln | 232 | . | . | B | . | . | . | . | 0.83 | 0.69 | . | . | F | −0.10 | 2.30 |
| Thr | 233 | . | . | B | . | . | . | . | 1.48 | −0.10 | . | . | F | 0.80 | 2.60 |
| Phe | 234 | . | . | B | . | . | . | . | 1.88 | −0.07 | . | * | F | 1.14 | 2.60 |
| Gln | 235 | . | . | B | . | . | . | . | 1.29 | −0.11 | . | * | F | 1.48 | 2.01 |
| Arg | 236 | . | . | B | . | . | . | . | 1.50 | −0.01 | * | * | F | 1.82 | 1.41 |
| Pro | 237 | . | . | . | . | T | . | . | 1.20 | −0.50 | * | . | F | 2.56 | 2.72 |
| Ser | 238 | . | . | . | . | T | T | . | 0.70 | −0.90 | * | . | F | 3.40 | 2.10 |
| Ala | 239 | . | . | . | . | T | T | . | 1.19 | −0.61 | * | * | F | 2.91 | 0.89 |
| Asp | 240 | . | . | . | . | T | T | . | 1.30 | −0.19 | * | * | F | 2.27 | 0.89 |
| Ser | 241 | . | . | B | . | . | T | . | 0.84 | −0.61 | * | * | F | 2.32 | 1.29 |
| Leu | 242 | . | . | . | . | . | T | C | 0.76 | −0.57 | * | * | F | 2.52 | 1.27 |
| Pro | 243 | . | . | B | . | . | T | . | 0.47 | −0.69 | * | * | F | 2.32 | 1.02 |
| Arg | 244 | . | . | . | . | T | T | . | 1.17 | −0.19 | * | * | F | 2.61 | 0.77 |
| Gly | 245 | . | . | . | . | T | T | . | 0.36 | −0.57 | * | * | F | 3.40 | 1.82 |
| Ser | 246 | . | . | B | . | . | . | . | 0.34 | −0.57 | * | * | F | 2.31 | 0.97 |
| Ala | 247 | . | . | B | . | . | . | . | 0.86 | −0.51 | * | * | F | 1.97 | 0.72 |
| Arg | 248 | . | . | B | . | . | . | . | 1.07 | −0.13 | * | * | F | 1.33 | 0.97 |
| Leu | 249 | . | . | B | . | . | . | . | 0.96 | −0.16 | * | * | F | 1.14 | 1.25 |
| Thr | 250 | . | . | B | . | . | . | . | 0.49 | −0.14 | * | * | F | 0.80 | 1.99 |
| Ser | 251 | . | . | B | . | . | T | . | 0.54 | 0.04 | * | * | F | 0.25 | 0.84 |
| Gln | 252 | . | . | B | . | . | T | . | 0.83 | 0.80 | * | * | F | 0.10 | 1.60 |
| Asn | 253 | . | . | B | . | . | T | . | 0.72 | 0.50 | * | * | F | 0.10 | 1.48 |
| Leu | 254 | . | . | B | . | . | T | . | 0.68 | 0.41 | . | . | F | 0.10 | 1.78 |
| Tyr | 255 | . | . | B | . | . | T | . | 0.29 | 0.67 | * | . | . | −0.20 | 0.76 |
| Ser | 256 | . | . | B | . | . | T | . | 0.63 | 1.06 | * | . | . | −0.20 | 0.41 |
| Asn | 257 | . | . | B | . | . | T | . | 0.42 | 0.66 | * | . | . | −0.20 | 0.99 |
| Val | 258 | . | . | B | . | . | T | . | −0.17 | 0.40 | * | . | . | −0.20 | 0.98 |
| Phe | 259 | . | . | B | . | . | . | . | 0.64 | 0.14 | * | . | . | −0.10 | 0.74 |
| Lys | 260 | . | . | B | . | . | . | . | 0.03 | −0.24 | * | . | F | 0.65 | 0.77 |
| Pro | 261 | . | . | B | . | . | . | . | −0.52 | 0.00 | * | . | F | 0.05 | 0.77 |
| Ala | 262 | . | . | B | B | . | . | . | −0.82 | 0.00 | * | . | F | −0.15 | 0.66 |
| Asp | 263 | . | . | B | B | . | . | . | −0.18 | −0.40 | * | . | . | 0.30 | 0.44 |
| Val | 264 | . | . | B | B | . | . | . | 0.57 | 0.03 | * | * | . | −0.30 | 0.44 |
| Val | 265 | . | . | B | B | . | . | . | −0.37 | −0.40 | * | * | . | 0.30 | 0.87 |
| Ser | 266 | . | . | B | B | . | . | . | −0.37 | −0.21 | . | * | F | 0.45 | 0.37 |
| Pro | 267 | . | . | B | . | . | . | . | −0.08 | 0.21 | * | . | F | 0.05 | 0.76 |
| Lys | 268 | . | . | B | . | . | . | . | −0.42 | −0.04 | * | . | F | 0.80 | 1.38 |
| Ile | 269 | . | . | . | . | . | T | C | −0.27 | −0.26 | . | * | F | 1.20 | 1.02 |
| Pro | 270 | . | . | . | . | . | T | C | 0.38 | 0.14 | . | * | F | 0.45 | 0.57 |
| Ser | 271 | . | . | . | . | T | T | . | −0.21 | 0.14 | . | * | F | 0.65 | 0.44 |
| Gly | 272 | . | . | . | . | . | T | C | 0.00 | 0.83 | . | * | F | 0.15 | 0.44 |
| Phe | 273 | . | A | B | . | . | . | . | −0.04 | 0.14 | . | * | F | −0.15 | 0.49 |
| Pro | 274 | . | A | B | . | . | . | . | 0.81 | −0.29 | . | * | . | 0.30 | 0.62 |
| Ile | 275 | . | A | B | . | . | . | . | 1.02 | −0.17 | . | . | . | 0.30 | 0.85 |
| Glu | 276 | . | A | B | . | . | . | . | 1.01 | −0.60 | . | . | F | 0.90 | 1.69 |
| Asp | 277 | . | A | . | . | . | T | . | 1.06 | −0.90 | . | . | F | 1.30 | 1.58 |
| His | 278 | . | A | . | . | . | T | . | 1.54 | −0.94 | . | . | F | 1.30 | 3.02 |
| Glu | 279 | . | A | . | . | . | T | . | 0.94 | −1.20 | * | . | F | 1.30 | 2.70 |
| Thr | 280 | . | A | . | . | . | . | C | 1.83 | −0.51 | * | . | F | 1.44 | 1.33 |
| Ser | 281 | . | . | . | . | . | T | C | 1.83 | −0.51 | . | . | F | 2.18 | 1.64 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 282 | . | . | . | . | T | T | . | 1.53 | −0.61 | . | . | F | 2.72 | 1.52 |
| Leu | 283 | . | . | . | . | T | T | . | 1.57 | −0.23 | . | . | F | 2.76 | 1.41 |
| Asp | 284 | . | . | . | . | T | T | . | 0.98 | −0.71 | . | . | F | 3.40 | 1.76 |
| Asn | 285 | . | . | . | . | . | T | C | 0.59 | −0.60 | . | . | F | 2.86 | 1.15 |
| Ser | 286 | . | . | . | . | . | T | C | 0.08 | −0.24 | . | . | F | 2.22 | 1.21 |
| Asp | 287 | . | . | B | . | . | T | . | −0.01 | −0.24 | . | . | F | 1.53 | 0.60 |
| Ala | 288 | . | . | B | . | . | T | . | 0.49 | 0.14 | . | . | F | 0.59 | 0.50 |
| Phe | 289 | . | . | B | . | . | . | . | 0.46 | 0.23 | . | * | . | −0.10 | 0.53 |
| Leu | 290 | . | . | B | . | . | . | . | −0.36 | 0.34 | . | * | . | −0.10 | 0.44 |
| Ser | 291 | . | . | B | . | . | . | . | −0.01 | 1.03 | . | * | . | −0.40 | 0.36 |
| Thr | 292 | . | A | B | . | . | . | . | −0.82 | 0.53 | * | * | F | −0.45 | 0.82 |
| His | 293 | . | A | B | . | . | . | . | −0.93 | 0.43 | * | * | . | −0.60 | 0.82 |
| Leu | 294 | . | A | B | . | . | . | . | −0.44 | 0.53 | * | * | . | −0.60 | 0.53 |
| Lys | 295 | . | A | B | . | . | . | . | 0.77 | 0.57 | * | * | . | −0.60 | 0.57 |
| Leu | 296 | . | A | B | . | . | . | . | −0.22 | 0.47 | * | * | . | −0.60 | 0.56 |
| Phe | 297 | . | . | B | . | . | T | . | −0.21 | 0.47 | * | * | . | −0.20 | 0.69 |
| Pro | 298 | . | . | B | . | . | T | . | −0.48 | 0.17 | * | * | F | 0.25 | 0.46 |
| Ser | 299 | . | . | . | . | . | T | C | 0.33 | 0.56 | * | * | F | 0.15 | 0.75 |
| Ala | 300 | . | . | . | . | . | T | C | −0.01 | 0.27 | * | * | F | 0.60 | 1.39 |
| Ser | 301 | . | . | . | . | . | T | C | 0.10 | −0.13 | . | . | F | 1.20 | 1.20 |
| Ser | 302 | . | . | . | . | . | T | C | 0.56 | 0.23 | . | . | F | 0.45 | 0.78 |
| Asn | 303 | . | . | . | . | . | T | C | 0.77 | 0.60 | . | . | F | 0.30 | 1.20 |
| Ser | 304 | . | . | . | . | . | T | C | 0.77 | 0.10 | . | . | F | 0.60 | 1.56 |
| Phe | 305 | . | . | . | . | . | . | C | 1.36 | 0.10 | . | . | F | 0.60 | 1.56 |
| Tyr | 306 | . | . | B | . | . | . | . | 0.84 | −0.29 | . | . | F | 1.20 | 1.68 |
| Glu | 307 | . | . | B | . | . | . | . | 0.93 | 0.00 | . | . | F | 0.80 | 1.03 |
| Ser | 308 | . | . | B | . | . | . | . | 0.93 | 0.04 | . | . | F | 1.00 | 1.84 |
| Glu | 309 | . | . | . | . | . | . | C | 0.89 | −0.34 | . | . | F | 2.00 | 2.03 |
| Leu | 310 | . | . | . | . | . | . | C | 0.89 | −0.67 | * | . | F | 2.10 | 1.16 |
| Pro | 311 | . | . | . | . | T | T | . | 1.13 | 0.11 | * | . | F | 1.25 | 0.75 |
| Gln | 312 | . | . | . | . | T | T | . | 1.13 | 0.13 | * | . | F | 1.05 | 0.75 |
| Gly | 313 | . | . | . | . | T | T | . | 1.19 | 0.13 | * | . | F | 1.00 | 1.52 |
| Phe | 314 | . | . | B | . | . | T | . | 0.94 | 0.20 | * | . | F | 0.40 | 1.54 |
| Gln | 315 | . | . | B | . | . | T | . | 1.76 | 0.53 | * | . | F | 0.10 | 1.39 |
| Asp | 316 | . | . | B | . | . | T | . | 1.16 | 0.53 | * | . | . | −0.05 | 2.27 |
| Tyr | 317 | . | . | B | . | . | T | . | 0.81 | 0.79 | * | . | . | −0.05 | 2.16 |
| Tyr | 318 | . | . | . | . | T | T | . | 1.16 | 0.43 | * | . | . | 0.35 | 1.23 |
| Asn | 319 | . | . | . | . | T | . | . | 1.16 | 0.43 | * | . | . | 0.15 | 1.28 |
| Leu | 320 | . | . | . | . | T | . | . | 0.84 | 1.21 | * | . | . | 0.00 | 0.71 |
| Gly | 321 | . | . | . | . | T | . | . | 0.84 | 0.94 | * | . | . | 0.00 | 0.65 |
| Gln | 322 | . | . | B | . | . | . | . | 1.09 | 0.19 | * | . | F | 0.39 | 0.68 |
| Phe | 323 | . | . | B | . | . | . | . | 1.33 | −0.21 | . | . | F | 1.48 | 1.37 |
| Thr | 324 | . | . | B | . | . | . | . | 1.33 | −0.90 | . | . | F | 2.12 | 2.31 |
| Asp | 325 | . | . | B | . | . | T | . | 1.29 | −0.93 | . | . | F | 2.66 | 2.31 |
| Asp | 326 | . | . | . | . | T | T | . | 1.42 | −0.69 | . | * | F | 3.40 | 1.98 |
| Asp | 327 | . | . | . | . | T | T | C | 1.11 | −1.04 | . | * | F | 3.06 | 2.12 |
| Gln | 328 | . | . | B | . | . | T | C | 1.60 | −1.04 | . | . | F | 2.52 | 1.83 |
| Val | 329 | . | . | . | . | . | T | C | 1.10 | −0.61 | . | . | F | 2.18 | 1.70 |
| Pro | 330 | . | . | B | . | . | T | . | 0.24 | 0.07 | . | . | F | 0.59 | 0.84 |
| Thr | 331 | . | . | B | . | . | T | . | −0.34 | 0.71 | . | . | F | −0.05 | 0.36 |
| Pro | 332 | . | . | B | . | . | T | . | −1.23 | 0.81 | * | . | F | −0.05 | 0.49 |
| Leu | 333 | . | . | B | B | . | . | . | −1.54 | 0.86 | . | * | . | −0.60 | 0.22 |
| Val | 334 | . | . | B | B | . | . | . | −1.58 | 0.91 | . | * | . | −0.60 | 0.22 |
| Ala | 335 | . | . | B | B | . | . | . | −1.68 | 1.11 | . | . | . | −0.60 | 0.10 |
| Ile | 336 | . | . | B | B | . | . | . | −1.26 | 1.17 | * | . | . | −0.60 | 0.18 |
| Thr | 337 | . | . | B | B | . | . | . | −1.86 | 0.49 | * | . | . | −0.60 | 0.46 |
| Ile | 338 | . | . | B | B | . | . | . | −1.90 | 0.53 | * | . | . | −0.60 | 0.38 |
| Thr | 339 | . | . | B | B | . | . | . | −1.90 | 0.67 | * | . | . | −0.60 | 0.40 |
| Arg | 340 | . | . | B | B | . | . | . | −1.66 | 0.63 | * | * | . | −0.60 | 0.21 |
| Leu | 341 | . | . | B | B | . | . | . | −1.47 | 0.57 | * | . | . | −0.60 | 0.29 |
| Val | 342 | . | . | B | B | . | . | . | −1.97 | 0.67 | * | * | . | −0.60 | 0.17 |
| Val | 343 | . | . | B | B | . | . | . | −1.89 | 0.87 | * | * | . | −0.60 | 0.07 |
| Gly | 344 | . | . | B | B | . | . | . | −1.79 | 1.56 | * | * | . | −0.60 | 0.07 |
| Phe | 345 | . | . | B | B | . | . | . | −2.20 | 1.30 | * | * | . | −0.60 | 0.15 |
| Leu | 346 | . | . | B | B | . | . | . | −2.24 | 1.04 | * | . | . | −0.60 | 0.28 |
| Leu | 347 | . | . | B | B | . | . | . | −2.28 | 1.04 | . | . | . | −0.60 | 0.21 |
| Pro | 348 | . | . | B | B | . | . | . | −2.02 | 1.30 | . | . | . | −0.60 | 0.17 |
| Ser | 349 | . | . | B | B | . | . | . | −2.57 | 1.13 | . | . | . | −0.60 | 0.20 |
| Val | 350 | . | . | B | B | . | . | . | −2.46 | 1.13 | . | . | . | −0.60 | 0.17 |
| Ile | 351 | . | . | B | B | . | . | . | −2.31 | 0.94 | . | . | . | −0.60 | 0.11 |
| Met | 352 | . | . | B | B | . | . | . | −1.74 | 1.09 | . | . | . | −0.60 | 0.04 |
| Ile | 353 | . | . | B | B | . | . | . | −1.83 | 1.46 | . | . | . | −0.60 | 0.09 |
| Ala | 354 | . | . | B | B | . | . | . | −2.23 | 1.20 | . | . | . | −0.60 | 0.18 |
| Cys | 355 | . | . | B | B | . | . | . | −2.27 | 1.30 | . | . | . | −0.60 | 0.16 |
| Tyr | 356 | . | . | B | B | . | . | . | −2.23 | 1.37 | . | . | . | −0.60 | 0.16 |
| Ser | 357 | . | . | B | B | . | . | . | −2.33 | 1.33 | * | * | . | −0.60 | 0.12 |
| Phe | 358 | . | . | B | B | . | . | . | −1.33 | 1.61 | * | * | . | −0.60 | 0.19 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ile | 359 | . | . | B | B | . | . | . | −1.34 | 1.04 | . | * | . | −0.60 | 0.23 |
| Val | 360 | . | . | B | B | . | . | . | −0.68 | 0.90 | * | . | . | −0.60 | 0.17 |
| Phe | 361 | . | . | B | B | . | . | . | −0.32 | 0.91 | * | . | . | −0.26 | 0.35 |
| Arg | 362 | . | . | B | B | . | . | . | −0.37 | 0.13 | . | * | . | 0.38 | 0.97 |
| Met | 363 | . | . | B | B | . | . | . | 0.44 | −0.13 | . | * | . | 1.47 | 1.29 |
| Gln | 364 | . | . | . | . | . | T | T | 0.63 | −0.77 | . | * | F | 3.06 | 2.92 |
| Arg | 365 | . | . | . | . | . | T | T | 0.90 | −0.77 | . | . | F | 3.40 | 1.29 |
| Gly | 366 | . | . | . | . | . | T | T | . | 1.64 | −0.27 | . | * | F | 2.76 | 1.32 |
| Arg | 367 | . | . | . | . | . | T | T | . | 1.23 | −0.89 | . | . | F | 2.72 | 1.52 |
| Phe | 368 | . | . | . | . | . | . | . | C | 1.83 | −0.90 | . | * | F | 2.32 | 1.04 |
| Ala | 369 | . | . | . | . | . | . | . | C | 1.53 | −0.50 | * | * | F | 2.02 | 1.82 |
| Lys | 370 | . | . | . | . | . | . | . | C | 1.47 | −0.54 | . | * | F | 2.32 | 1.25 |
| Ser | 371 | . | . | . | . | . | T | C | 1.50 | −0.54 | * | . | F | 2.86 | 2.88 |
| Gln | 372 | . | . | . | . | . | T | T | . | 0.69 | −0.84 | * | . | F | 3.40 | 4.12 |
| Ser | 373 | . | . | . | . | . | T | T | . | 1.50 | −0.56 | * | * | F | 3.06 | 1.78 |
| Lys | 374 | . | . | . | . | . | T | T | . | 1.23 | −0.56 | * | * | F | 2.72 | 2.60 |
| Thr | 375 | . | . | B | B | . | . | . | 0.60 | −0.30 | * | * | F | 1.28 | 1.12 |
| Phe | 376 | . | . | B | B | . | . | . | 0.04 | −0.20 | . | * | . | 0.64 | 0.84 |
| Arg | 377 | . | . | B | B | . | . | . | −0.81 | 0.06 | * | * | . | −0.30 | 0.31 |
| Val | 378 | . | . | B | B | . | . | . | −1.37 | 0.70 | * | * | . | −0.60 | 0.16 |
| Ala | 379 | . | . | B | B | . | . | . | −2.27 | 0.86 | * | * | . | −0.60 | 0.14 |
| Val | 380 | . | . | B | B | . | . | . | −2.54 | 0.71 | . | * | . | −0.60 | 0.05 |
| Val | 381 | . | . | B | B | . | . | . | −2.70 | 1.21 | * | * | . | −0.60 | 0.07 |
| Val | 382 | . | . | B | B | . | . | . | −3.51 | 1.21 | * | * | . | −0.60 | 0.05 |
| Val | 383 | . | . | B | B | . | . | . | −3.47 | 1.50 | . | . | . | −0.60 | 0.06 |
| Ala | 384 | . | . | B | B | . | . | . | −3.73 | 1.54 | . | . | . | −0.60 | 0.07 |
| Val | 385 | . | . | B | B | . | . | . | −3.54 | 1.54 | . | . | . | −0.60 | 0.07 |
| Phe | 386 | . | . | B | B | . | . | . | −2.98 | 1.47 | . | . | . | −0.60 | 0.05 |
| Leu | 387 | . | . | B | B | . | . | . | −2.43 | 1.74 | . | . | . | −0.60 | 0.05 |
| Val | 388 | . | . | B | B | . | . | . | −1.79 | 1.73 | . | . | . | −0.60 | 0.10 |
| Cys | 389 | . | . | . | B | T | . | . | −1.44 | 1.51 | . | . | . | −0.20 | 0.18 |
| Trp | 390 | . | . | B | B | . | . | . | −0.62 | 1.49 | . | . | . | −0.60 | 0.34 |
| Thr | 391 | . | . | B | . | . | T | . | −0.81 | 1.30 | . | . | . | −0.20 | 0.61 |
| Pro | 392 | . | . | . | . | T | T | . | −0.70 | 1.34 | . | . | . | 0.20 | 0.80 |
| Tyr | 393 | . | . | . | . | T | T | . | −0.19 | 1.56 | . | . | . | 0.20 | 0.66 |
| His | 394 | . | . | B | . | . | T | . | −0.38 | 1.07 | . | . | . | −0.20 | 0.45 |
| Ile | 395 | . | . | B | B | . | . | . | −0.90 | 0.23 | . | . | . | −0.60 | 0.22 |
| Phe | 396 | . | . | B | B | . | . | . | −0.89 | 1.49 | . | . | . | −0.60 | 0.11 |
| Gly | 397 | . | . | B | B | . | . | . | −1.49 | 1.11 | . | . | . | −0.60 | 0.11 |
| Val | 398 | . | . | B | B | . | . | . | −2.06 | 1.30 | . | . | . | −0.60 | 0.13 |
| Leu | 399 | . | . | B | B | . | . | . | −2.33 | 1.30 | * | . | . | −0.60 | 0.13 |
| Ser | 400 | . | . | B | B | . | . | . | −1.44 | 1.00 | * | . | . | −0.60 | 0.18 |
| Leu | 401 | . | . | B | B | . | . | . | −0.96 | 0.57 | * | . | . | −0.60 | 0.42 |
| Leu | 402 | . | . | . | B | . | . | C | −0.61 | 0.36 | * | . | . | −0.10 | 0.78 |
| Thr | 403 | . | . | . | B | . | . | C | −0.07 | −0.33 | * | . | F | 1.10 | 1.01 |
| Asp | 404 | . | . | . | . | . | T | C | 0.53 | −0.23 | * | * | F | 1.80 | 1.76 |
| Pro | 405 | . | . | . | . | . | T | C | 0.02 | −0.49 | . | . | F | 2.10 | 3.30 |
| Glu | 406 | . | . | B | . | . | T | . | 0.49 | −0.49 | * | . | F | 2.20 | 1.89 |
| Thr | 407 | . | . | . | . | . | T | C | 1.34 | −0.54 | * | . | F | 3.00 | 1.12 |
| Pro | 408 | . | . | . | . | . | . | C | 1.34 | −0.54 | * | . | F | 2.50 | 1.45 |
| Leu | 409 | . | . | . | . | T | . | . | 0.53 | −0.49 | * | . | F | 2.10 | 1.20 |
| Gly | 410 | . | . | . | . | T | . | . | 0.14 | 0.20 | * | . | F | 1.05 | 0.69 |
| Lys | 411 | . | A | B | . | . | . | . | −0.16 | 0.33 | * | . | F | 0.15 | 0.44 |
| Thr | 412 | . | A | B | . | . | . | . | −0.13 | 0.29 | * | . | F | −0.15 | 0.72 |
| Leu | 413 | . | A | B | . | . | . | . | 0.08 | 0.51 | * | . | . | −0.60 | 0.76 |
| Met | 414 | . | A | B | . | . | . | . | 0.86 | 0.09 | * | . | . | −0.30 | 0.64 |
| Ser | 415 | . | A | B | . | . | . | . | 0.34 | 0.59 | * | . | . | −0.60 | 0.60 |
| Trp | 416 | . | A | B | . | . | . | . | −0.37 | 0.74 | . | . | . | −0.60 | 0.54 |
| Asp | 417 | . | A | B | . | . | . | . | −0.94 | 0.63 | . | . | . | −0.60 | 0.29 |
| His | 418 | . | A | B | . | . | . | . | −0.72 | 0.70 | . | . | . | −0.60 | 0.15 |
| Val | 419 | . | A | B | . | . | . | . | −0.93 | 0.81 | . | . | . | −0.60 | 0.15 |
| Cys | 420 | . | A | B | . | . | . | . | −1.22 | 0.59 | . | . | . | −0.60 | 0.07 |
| Ile | 421 | . | A | B | . | . | . | . | −1.23 | 1.09 | . | . | . | −0.60 | 0.05 |
| Ala | 422 | . | A | B | . | . | . | . | −1.82 | 0.97 | . | . | . | −0.60 | 0.10 |
| Leu | 423 | . | A | B | . | . | . | . | −1.79 | 0.83 | . | . | . | −0.60 | 0.18 |
| Ala | 424 | . | A | B | . | . | . | . | −1.23 | 0.66 | . | . | . | −0.60 | 0.42 |
| Ser | 425 | . | . | B | . | . | T | . | −1.23 | 0.36 | . | . | . | 0.10 | 0.56 |
| Ala | 426 | . | . | . | . | T | T | . | −1.04 | 0.43 | . | * | . | 0.20 | 0.36 |
| Asn | 427 | . | . | . | . | T | T | . | −0.46 | 0.53 | * | * | . | 0.20 | 0.31 |
| Ser | 428 | . | . | . | . | T | T | . | 0.14 | 0.43 | * | . | . | 0.20 | 0.37 |
| Cys | 429 | . | . | . | . | T | . | . | 0.03 | 0.47 | * | * | . | 0.00 | 0.57 |
| Phe | 430 | . | . | B | . | . | . | . | −0.48 | 0.76 | * | * | . | −0.40 | 0.31 |
| Asn | 431 | . | . | B | . | . | T | . | −0.13 | 1.04 | * | . | . | −0.20 | 0.19 |
| Pro | 432 | . | . | B | . | . | T | . | −0.72 | 1.41 | * | . | . | −0.20 | 0.55 |
| Phe | 433 | . | . | B | . | . | T | . | −1.23 | 1.34 | * | . | . | −0.20 | 0.64 |
| Leu | 434 | . | . | B | . | . | T | . | −1.38 | 1.24 | * | . | . | −0.20 | 0.33 |
| Tyr | 435 | . | A | B | . | . | . | . | −1.02 | 1.53 | . | * | . | −0.60 | 0.18 |

TABLE 2-continued

| Res | Position | I | II | III | IV | V | VI | VII | VIII | IX | X | XI | XII | XIII | XIV |
|-----|----------|---|----|----|----|----|----|----|------|------|---|----|----|------|------|
| Ala | 436 | . | A | B | . | . | . | . | −0.98 | 1.53 | . | . | . | −0.60 | 0.20 |
| Leu | 437 | . | A | B | . | . | . | . | −0.77 | 0.74 | . | . | . | −0.60 | 0.49 |
| Leu | 438 | . | A | B | . | . | . | . | −0.77 | 0.06 | * | * | . | −0.30 | 0.52 |
| Gly | 439 | A | . | . | . | . | T | . | 0.16 | 0.09 | * | . | F | 0.25 | 0.45 |
| Lys | 440 | A | . | . | . | . | T | . | 0.44 | −0.41 | * | * | F | 1.00 | 1.06 |
| Asp | 441 | A | . | . | . | . | T | . | 1.08 | −1.10 | * | * | F | 1.30 | 2.57 |
| Phe | 442 | . | . | B | . | . | T | . | 1.30 | −1.79 | * | * | F | 1.30 | 5.19 |
| Arg | 443 | . | A | B | . | . | . | . | 2.22 | −1.71 | * | * | F | 0.90 | 2.62 |
| Lys | 444 | . | A | B | . | . | . | . | 2.57 | −1.71 | * | * | F | 0.90 | 3.08 |
| Lys | 445 | . | A | . | . | T | . | . | 2.22 | −1.31 | * | * | F | 1.30 | 6.15 |
| Ala | 446 | . | A | . | . | . | . | C | 1.33 | −1.71 | * | * | F | 1.10 | 4.21 |
| Arg | 447 | . | A | . | B | T | . | . | 2.03 | −1.03 | * | * | F | 1.30 | 1.48 |
| Gln | 448 | . | A | B | B | . | . | . | 1.58 | −0.63 | * | * | F | 0.90 | 1.28 |
| Ser | 449 | . | A | B | B | . | . | . | 0.64 | −0.20 | * | * | F | 0.60 | 1.25 |
| Ile | 450 | . | . | B | B | . | . | . | −0.21 | −0.01 | * | * | F | 0.45 | 0.45 |
| Gln | 451 | . | A | B | B | . | . | . | 0.38 | 0.67 | * | * | F | −0.45 | 0.21 |
| Gly | 452 | . | A | B | B | . | . | . | −0.32 | 0.27 | * | * | . | −0.30 | 0.28 |
| Ile | 453 | . | A | B | B | . | . | . | −0.91 | 0.39 | * | * | . | −0.30 | 0.40 |
| Leu | 454 | . | A | B | B | . | . | . | −1.31 | 0.20 | * | * | . | −0.30 | 0.23 |
| Glu | 455 | . | A | B | B | . | . | . | −0.72 | 0.59 | * | * | . | −0.60 | 0.20 |
| Ala | 456 | . | A | . | . | . | . | C | −0.72 | 0.54 | . | * | . | −0.40 | 0.39 |
| Ala | 457 | . | A | . | . | . | . | C | −0.38 | −0.14 | . | * | . | 0.50 | 0.81 |
| Phe | 458 | A | A | . | . | . | . | . | −0.30 | −0.83 | . | * | . | 0.60 | 0.81 |
| Ser | 459 | A | A | . | . | . | . | . | 0.20 | −0.14 | * | * | . | 0.30 | 0.66 |
| Glu | 460 | A | A | . | . | . | . | . | 0.31 | −0.16 | * | . | F | 0.45 | 0.95 |
| Glu | 461 | A | A | . | . | . | . | . | 0.60 | −0.66 | * | . | F | 0.90 | 2.15 |
| Leu | 462 | . | A | . | B | T | . | . | 0.88 | −1.06 | * | . | F | 1.30 | 2.15 |
| Thr | 463 | . | A | . | B | T | . | . | 1.54 | −0.96 | * | . | F | 1.30 | 1.79 |
| Arg | 464 | . | A | . | B | T | . | . | 1.18 | −0.46 | * | . | F | 1.00 | 1.41 |
| Ser | 465 | . | A | . | B | T | . | . | 0.97 | 0.11 | * | . | F | 0.25 | 0.91 |
| Thr | 466 | . | . | . | B | T | . | . | 0.67 | −0.14 | * | . | F | 0.85 | 0.98 |
| His | 467 | . | . | . | B | T | . | . | 1.48 | −0.24 | * | . | F | 0.85 | 0.67 |
| Cys | 468 | . | . | . | . | . | T | C | 1.79 | 0.16 | * | . | F | 0.45 | 0.80 |
| Pro | 469 | . | . | . | . | T | T | . | 0.82 | 0.17 | * | . | F | 0.65 | 0.90 |
| Ser | 470 | . | . | . | . | T | T | . | 0.23 | 0.33 | . | . | F | 0.65 | 0.49 |
| Asn | 471 | . | . | . | . | . | T | C | 0.24 | 0.51 | . | . | F | 0.15 | 0.64 |
| Asn | 472 | . | . | B | B | . | . | . | 0.28 | 0.33 | . | . | F | −0.15 | 0.55 |
| Val | 473 | . | . | B | B | . | . | . | 1.06 | −0.10 | . | . | . | 0.64 | 0.72 |
| Ile | 474 | . | . | B | B | . | . | . | 1.27 | −0.49 | . | . | . | 0.98 | 0.87 |
| Ser | 475 | . | . | B | B | . | . | . | 1.27 | −0.49 | . | . | F | 1.47 | 0.87 |
| Glu | 476 | . | . | B | . | . | T | . | 0.96 | −0.50 | . | . | F | 2.36 | 1.57 |
| Arg | 477 | . | . | . | . | T | T | . | 0.64 | −0.66 | . | . | F | 3.40 | 3.24 |
| Asn | 478 | . | . | . | . | T | T | . | 0.64 | −0.86 | . | * | F | 3.06 | 3.49 |
| Ser | 479 | . | . | . | . | T | T | . | 1.14 | −0.60 | . | * | F | 2.72 | 1.50 |
| Thr | 480 | . | . | . | B | . | . | C | 1.06 | −0.17 | . | . | . | 1.18 | 0.98 |
| Thr | 481 | . | . | B | B | . | . | . | 0.67 | 0.26 | * | . | . | 0.04 | 0.78 |
| Val | 482 | . | . | B | B | . | . | . | 0.17 | 0.29 | * | * | . | −0.30 | 0.74 |

In another aspect, the invention provides an antibody that binds a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Leamer, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides are therefore useful to raise antibodies, including monoclonal antibodies, that bind to a C3a Receptor polypeptide of the invention. See, for instance, Wilson et al., *Cell* 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:2.

Antibodies of the invention may bind one or more antigenic C3a Receptor polypeptides or peptides including, but not limited to: a polypeptide comprising amino acid residues from about 7 to about 12, a polypeptide comprising amino acid residues from about 165 to about 170, a polypeptide comprising amino acid residues from about 191 to about 197, a polypeptide comprising acid residues from about 204 to about 220, a polypeptide comprising amino acid residues from about 235 to about 247, a polypeptide comprising amino acid residues from about 280 to about 287, a polypeptide comprising amino acid residues from about 323 to about 329, a polypeptide comprising amino acid residues from about 363 to about 374, a polypeptide comprising amino acid residues from about 404 to about 409, and/or a polypeptide comprising amino acid residues from about 475 to about 479 of SEQ ID NO:2. In this context "about" includes the particularly recited range, larger or smaller by several (5, 4, 3, 2, or 1) amino acids, at either terminus or at both termini. As indicated above, the inventors have determined that the above polypeptide fragments are antigenic regions of the C3a Receptor protein. Epitope-bearing C3a Receptor peptides and polypeptides may be produced by any conventional means. Houghten, R. A., "General method for the rapid solid-phase synthesis of large numbers of peptides: specificity of antigen-antibody interaction at the level of individual amino acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, C3a Receptor polypeptides and the epitope-bearing fragments thereof described herein can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric C3a Receptor protein or protein fragment alone (Fountoulakis et al., *J. Biochem* 270:3958-3964 (1995)). Thus, antibodies of the invention may bind fusion proteins that comprise all or a portion of a C3a Receptor polypeptide.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified C3a Receptor polypeptides or C3a Receptor polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function, or loss of the ability to be bound by a specific antibody. For instance, Ron et al., *J. Biol. Chem.*, 268:2984-2988 (1993) reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other functional activities (e.g., biological activities, ability to multimerize, ability to reduce insulin and/or cellular glucose uptake) may still be retained. For example, the ability of shortened C3a Receptor polypeptides to induce and/or bind to antibodies which recognize the complete or mature forms of the C3a Receptor polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a C3a Receptor polypeptide with a large number of deleted N-terminal amino acid residues may retain some biological or immunogenic activities. In fact, peptides composed of as few as six C3a Receptor amino acid residues may be antigenic.

Accordingly, the present invention further provides antibodies that bind polypeptides having one or more residues deleted from the amino terminus of the C3a Receptor amino acid sequence of SEQ ID NO:2 up to the Valine residue at position 477 and polynucleotides encoding such polypeptides. In particular, the present invention provides antibodies that bind polypeptides comprising the amino acid sequence of residues $n^1$-482 of SEQ ID NO:2, where $n^1$ is an integer from 2 to 477 corresponding to the position of the amino acid residue in SEQ ID NO:2.

More in particular, the invention provides antibodies that bind polypeptides comprising, or alternatively consisting of, the amino acid sequence of residues of A-2 to V482; S-3 to V482; F4 to V482; S-5 to V482; A-6 to V-482; E-7 to V-482; T-8 to V-482; N-9 to V482; S-10 to V482; T-11 to V482; D-12 to V482; L-13 to V482; L-14 to V-482; S-15 to V-482; Q-16 to V-482; P-17 to V-482; W-18 to V482; N-19 to V482; E-20 to V-482; P-21 to V482; P-22 to V-482; V-23 to V-482; I-24 to V-482; L-25 to V-482; S-26 to V-482; M-27 to V482; V-28 to V-482; I-29 to V-482; L-30 to V-482; S-31 to V-482; L-32 to V-482; T-33 to V-482; F-34 to V-482; L-35 to V-482; L-36 to V-482; G-37 to V-482; L-38 to V-482; P-39 to V-482; G40 to V-482; N-41 to V-482; G-42 to V-482; G-42 to V-482; L-43 to V-482; V-44 to V-482; L-45 to V-482; W-46 to V-482; V-47 to V-482; A-48 to V-482; G-49 to V-482; L-50 to V-482; K-51 to V-482; M-52 to V-482; Q-53 to V-482; R-54 to V-482; T-55 to V-482; V-56 to V-482; N-57 to V-482; T-58 to V-482; I-59 to V-482; W-60 to V-482; F-61 to V-482; L-62 to V-482; H-63 to V-482; L-64 to V-482; T-65 to V-482; L-66 to V-482; A-67 to V-482; D-68 to V-482; L-69 to V-482; L-70 to V-482; C-71 to V-482; C-72 to V-482; L-73 to V-482; S-74 to V-482; L-75 to V-482; P-76 to V-482; F-77 to V-482; S-78 to V-482; L-79 to V-482; A-80 to V-482; H-81 to V-482; L-82 to V-482; A-83 to V-482; L-84 to V-482; Q-85 to V-482; G-86 to V-482; Q-87 to V-482; to W-88 to V-482; P-89 to V-482; Y-90 to V-482; G-91 to V-482; R-92 to V-482; F-93 to V-482; L-94 to V-482; C-95 to V-482; K-96 to V-482; L-97 to V-482; I-98 to V-482; P-99 to V-482; S-100 to V-482; I-101 to V-482; I-102 to V-482; V-103 to V-482; L-104 to V-482; N-105 to V-482; M-106 to V-482; F-107 to V-482; A-108 to V-482; S-109 to V-482; V-110 to V-482; F-111 to V-482; L-112 to V-482; L-113 to V-482; T-114 to V-482; A-115 to V-482; I-116 to V-482; S-117 to V-482; L-118 to V-482; D-119 to V-482; R-120 to V-482; C-121 to V-482; L-122 to V-482; V-123 to V-482; V-124 to V-482; F-125 to V-482; K-126 to V-482; P-127 to V-482; I-128 to V-482; W-129 to V-482; C-130 to V-482; Q-131 to V-482; N-132 to V-482; H-133 to V-482; R-134 to V-482; N-135 to V-482; V-136 to V-482; G-137 to V-482; M-138 to V-482; A-139 to V-482; C-140 to V-482; S-141 to V-482; I-142 to V-482; C-143 to V-482; G-144 to V-482; C-145 to V-482; I-146 to V-482; W-147 to V-482; V-148 to V-482; V-149 to V-482; A-150 to V-482; C-151 to V-482; V-152 to V-482; M-153 to V-482; C-154 to V-482; I-155 to V-482; P-156 to V-482; V-157 to V-482; F-158 to V-482; V-159 to V-482; Y-160 to V-482; R-161 to V-482; E-162 to V-482; I-163 to V-482; F-164 to V-482; T-165 to V-482; T-166 to V-482; D-167 to V-482; N-168 to V-482; H-169 to V-482; N-170 to V-482; R-171 to V-482; C-172 to V-482; G-173 to V-482; Y-174 to V-482; K-175 to V-482; F-176 to V-482; G-177 to V-482; L-178 to V-482; S-179 to V-482; S-180 to V-482; S-181 to V-482; L-182 to V-482; D-183 to V-482; Y-184 to V-482; P-185 to V-482; D-186 to V-482; F-187 to V-482; Y-188 to V-482; G-189 to V-482; D-190 to V-482; P-191 to V-482; L-192 to V-482; E-193 to V-482; N-194 to V-482; R-195 to V-482; S-196 to V-482; L-197 to V-482; E-198 to V-482; N-199 to V-482; I-200 to V482; V-201 to V-482; Q-202 to V-482 P-203 to V-482; P-204 to V-482; G-205 to V-482; E-206 to V-482; M-207 to V-482; N-208 to V-482; D-209 to V-482; R-210 to V-482; L-211 to V-482; D-212 to V-482; P-213 to V-482; S-214 to V-482; S-215 to V-482; F-216 to V-482; Q-217 to V-482; T-218 to V-482; N-219 to V-482; D-220 to V-482; H-221 to V-482; P-222 to V-482; W-223 to V-482; T-224 to V-482; V-225 to V-482; P-226 to V-482; T-227 to V-482; V-228 to V-482; F-229 to V-482; Q-230 to V-482; P-231 to V-482; Q-232 to V-482; T-233 to V-482; F-234 to V-482; Q-235 to V-482; R-236 to V-482; P-237 to V-482; S-238 to V-482; A-239 to V-482; D-240 to V-482; S-241 to V-482; L-242 to V-482; P-243 to V-482; R-244 to V-482; G-245 to V-482; S-246 to V-482; A-247 to V-482; R-248 to V-482; L-249 to V-482; T-250 to V-482; S-251 to V-482; Q-252 to V-482; N-253 to V-482; L-254 to V-482; Y-255 to V-482; S-256 to V-482; N-257 to V-482; V-258 to V-482; F-259 to V-482; K-260 to V-482; P-261 to V-482; A-262 to V-482; D-263 to V-482; V-264 to V-482; V-265 to V-482; S-266 to V-482; P-267 to V-482; K-268 to V-482; I-269 to V-482; P-270 to V-482; S-271 to V-482; G-272 to V-482; F-273 to V-482; P-274 to V-482; I-275 to V-482; E-276 to V-482; D-277 to V-482; H-278 to V-482; E-279 to V-482; T-280 to V-482; S-281 to V-482; P-282 to V-482; L-283 to V-482; D-284 to V-482; N-285 to V-482; S-286 to V-482; D-287 to V-482; A-288 to V-482; F-289 to V-482; L-290 to V-482; S-291 to V-482; T-292 to V-482; H-293 to V-482; L-294 to V-482; K-295 to V-482; L-296 to V-482; F-297 to V-482; P-298 to V-482; S-299 to V-482; A-300 to V-482; S-301 to V-482; S-302 to V-482; N-303 to V-482; S-304 to V-482; F-305 to V-482; Y-306 to V-482; E-307 to V-482; S-308 to V-482; E-309 to V-482; L-310 to V-482; P-311 to V-482; Q-312 to V-482; G-313 to V-482; F-314 to V-482; Q-315 to V-482; D-316 to V-482; Y-317 to V-482; Y-318 to V-482; N-319 to V-482; L-320 to V-482; G-321 to V-482; Q-322 to V-482; F-323 to V-482; T-324 to V-482; D-325 to V-482; D-326 to V-482; D-327 to V-482; Q-328 to V-482; V-329 to V-482; P-330 to V-482; T-331 to V-482; P-332 to V-482; L-333 to V-482; V-334 to V-482; A-335 to V-482; I-336 to V-482; T-337 to V-482; I-338 to V-482; T-339 to V-482; R-340 to V-482; L-341 to V-482; V-342 to V-482; V-343 to V-482; G-344 to V-482; F-345 to V-482; L-346 to V-482; L-347 to V-482; P-348 to V-482; S-349 to V-482; V-350 to V-482; I-351 to V-482; M-352 to V-482; I-353 to V-482; A-354 to V-482; C-355 to V-482; S-357 to V-482; F-358 to V-482; I-359 to V-482; V-360 to V-482; F-361 to V-482; R-362 to V-482; M-363 to V-482; Q-364 to V-482; R-365 to V-482; G-366 to V-482; R-367 to V-482; F-368 to V-482; A-369 to V-482; K-370 to V-482; S-371 to V-482; Q-372 to V-482; S-373 to V-482; K-374 to V-482; T-375 to V-482; F-376 to V-482; R-377 to V-482; V-378 to V-482; A-379 to V-482; V-380 to V-482; V-381 to V-482; V-382 to V-482; V-383 to V-482; A-384 to V-482; V-385 to V-482; F-386 to V-482; L-387 to V-482; V-388 to V-482; C-389 to V-482; W-390 to V-482; T-391 to V-482; P-392 to V-482; Y-393 to V-482; H-394 to V-482; I-395 to V-482; F-396 to V-482; G-397 to V-482; V-398 to V-482; L-399 to V-482; S-400 to V-482; L-401 to V-482; L-402 to V-482; T-403 to V-482; D-404 to V-482; P-405 to V-482; E-406 to V-482; T-407 to V-482; P-408 to V-482; L-409 to V-482; G-410 to V-482; K-411 to V-482; T-412 to V-482; L-413 to V-482; M-414 to V-482; S-415 to V-482; W-416 to V-482; D-417 to V-482; H-418 to V-482; V-419 to V-482; C-420 to V-482; I-421 to V-482; A-422 to V-482; L-423 to V-482; A-424 to V-482; S-425 to V-482; A-426 to V-482; N-427 to V-482; S-428 to V-482; C-429 to V-482; F-430 to V-482; N-431 to V-482; P-432 to V-482; F-433 to V-482; L-434 to V-482; Y-435 to V-482; A-436 to V-482; L-437 to V-482; L-438 to V-482; G-439 to V-482; K-440 to V-482; D-441 to V-482; F-442 to V-482; R-443 to V-482; K-444 to V-482; K-445 to V-482; A-446 to V-482; R-447 to V-482; Q-448 to V-482; S-449 to V-482; I-450 to V-482; Q-451 to V-482; G-452 to V-482; I-453 to V-482; L-454 to V-482; E-455 to V-482; A-456 to V-482; A-457 to V-482; F-458 to V-482; S-459 to V-482; E-460 to V-482; E-461 to V-482; L-462 to V-482; T-463 to V-482; R-464 to V-482; S-465 to V-482; T-466 to V-482; H-467 to V-482; C-468 to V-482; P-469 to V-482; S-470 to V-482; N-471 to V-482; N-472 to V-482; V-473 to V-482; I-474 to V-482; S-475 to V-482; E-476 to V-482; and/or R-477 to V-482; of SEQ ID NO:2. The present invention also encomapsses antibodies that bind C3a Receptor polypeptides that comprise, or alternatively consist of, an amino acid sequence at least 80%, 85%, 90%, 92%, 95%, 96%, 97%, 98%, 99% or 100% identical to the amino acid sequence described above.

As mentioned above, even if deletion of one or more amino acids from the C-terminus of a protein results in modification of loss of one or more biological functions of the protein, other functional activities (e.g., biological activities such as the ability to induce resistance to cellular insulin and/or glucose uptake) may still be retained. For example the ability of the shortened C3a Receptor polypeptide to induce and/or bind to antibodies which recognize the complete or mature forms of the C3a Receptor polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a C3a Receptor polypeptide with a large number of deleted C-terminal amino acid residues may retain some biological or immunogenic activities. In fact, peptides composed of as few as six C3a Receptor amino acid residues may be antigenic.

In another embodiment, antibodies of the invention bind C-terminal deletions of the C3a Receptor polypeptide that can be described by the general formula 1-$m^1$ where $m^1$ is a number from 6 to 481 corresponding to the amino acid sequence identified of SEQ ID NO:2. In specific embodiments, the invention provides antibodies that bind C3a Receptor polypeptides comprising, or alternatively consisting of, the amino acid sequence of residues: M-1 to T 481 ; M-1 to T-480; M-1 to S479; M-1 to N478; M-1 to R-477; M-1 to E-476; M-1 to S-475; M-1 to I-474; M-1 to V-473; M-1 to N-472; M-1 to N-471; M-1 to S-470; M-1 to P-469; M-1 to C-468; M-1 to H-467; M-1 to T-466; M-1 to S-465; M-1 to R-464; M-1 to T-463; M-1 to L-462; M-1 to E461; M-1 to E460; M-1 to S-459; M-1 to F-458; M-1 to A-457; M-1 to A-456; M-1 to E-455; M-1 to L-454; M-1 to I-453; M-1 to G-452; M-1 to Q-451; M-1 to I-450; M-1 to S-449; M-1 to Q-448; M-1 to R-447; M-1 to A-446; M-1 to K-445; M-1 to K-444; M-1 to R-443; M-1 to F-442; M-1 to D-441; M-1 to K-440; M-1 to G-439; M-1 to L-438; M-1 to L-437; M-1 to A-436; M-1 to Y-435; M-1 to L-434; M-1 to F-433; M-1 to P432; M-1 to N-431; M-1 to F-430; M-1 to C-429; M-1 to S-428; M-1 to N-427; M-1 to A-426; M-1 to S-425; M-1 to A-424; M-1 to L-423; M-1 to A-422; M-1 to I-421; M-1 to C-420; M-1 to V-419; M-1 to H-418; M-1 to D-417; M-1 to W-416; M-1 to S-415; M-1 to M-414; M-1 to L-413; M-1 to T-412; M-1 to K-411; M-1 to G-410; M-1 to L-409; M-1 to P-408; M-1 to T-407; M-1 to E-406; M-1 to P-405; M-1 to D-404; M-1 to T-403; M-1 to L-402; M-1 to L-401; M-1 to S-400; M-1 to L-399; M-1 to V-398; M-1 to G-397; M-1 to F-396; M-1 to I-395; M-1 to H-394; M-1 to Y-393; M-1 to P-392; M-1 to T-391; M-1 to W-390; M-1 to C-389; M-1 to V-388; M-1 to L-387; M-1 to F-386; M-1 to V-385; M-1 to A-384; M-1 to V-383; M-1 to V-382; M-1 to V-381; M-1 to V-380; M-1 to A-379; M-1 to V-378; M-1 to R-377; M-1 to F-376; M-1 to T-375; M-1 to K-374; M-1 to S-373; M-1 to Q-372; M-1 to S-371; M-1 to K-370; M-1 to A-369; M-1 to F-368; M-1 to R-367; M-1 to G-366; M-1 to R-365; M-1 to Q-364; M-1 to M-363; M-1 to R-362; M-1 to F-361; M-1 to V-360; M-1 to I-359; M-1 to F-358; M-1 to S-357; M-1 to Y-356; M-1 to C-355; M-1 to A-354; M-1 to I-353; M-1 to M-352; M-1 to I-351; M-1 to V-350; M-1 to S-349; M-1 to P-348; M-1 to L-347; M-1 to L-346; M-1 to F-345; M-1 to G-344; M-1 to V-343; M-1 to V-342; M-1 to L-341; M-1 to R-340; M-1 to T-339; M-1 to I-338; M-1 to T-377; M-1 to I-336; M-1 to A-335; M-1 to V-334; M-1 to L-333; M-1 to P-332; M-1 to T-331; M-1 to P-330; M-1 to V-329; M-1 to Q-328; M-1 to D-327; M-1 to D-326; M-1 to D-325; M-1 to T-324; M-1 to F-323; M-1 to Q-322; M-1 to G-321; M-1 to L-320; M-1 to N-319; M-1 to Y-318; M-1 to Y-317; M-1 to D-316; M-1 to Q-315; M-1 to F-314; M-1 to G-313; M-1 to Q-312; M-1 to P-311; M-1 to L-310; M-1 to E-309; M-1 to S-308; M-1 to E-307; M-1 to Y-306; M-1 to F-305; M-1 to S-304; M-1 to N-303; M-1 to S-302; M-1 to S-301; M-1 to A-300; M-1 to S-299; M-1 to P-298; M-1 to F-297; M-1 to L-296; M-1 to K-295; M-1 to L-294; M-1 to H-293; M-1 to T-292; M-1 to S-291; M-1 to L-290; M-1 to F-289; M-1 to A-288; M-1 to D-287; M-1 to S-286; M-1 to N-285; M-1 to D-284; M-1 to L-283 M-1 to P-282; M-1 to S-281; M-1 to T-280; M-1 to E-279; M-1 to H-278; M-1 to D-277; M-1 to E-276; M-1 to I-275; M-1 to P-274; M-1 to G-272; M-1 to S-271; M-1 to P-270; M-1 to I-269; M-1 to K-268; M-1 to P-267; M-1 to S-266; M-1 to V-265; M-1 to V-264; M-1 to D-263; M-1 to A-262; M-1 to P-261;M-1 to K-260; M-1 to F-259; M-1 to V-258; M-1 to N-257; M-1 to S-256; M-1 to Y-255; M-1 to L-254; M-1 to N-253; M-1 to Q-252; M-1 to S-251; M-1 to T-250; M-1 to L-249; M-1 to R-248; M-1 to A-247; M-1 to S-246; M-1 to G-245; M-1 to R-244; M-1 to P-243; M-1 to L-242; M-1 to S-241; M-1 to D-240; M-1 to A-239; M-1 to S-238; M-1 to P-237; M-1 to R-236; M-1 to Q-235; M-1 to F-234; M-1 to T-233; M-1 to Q-232; M-1 to P-231; M-1 to Q-230; M-1 to F-229; M-1 to V-228; M-1 to T-227; M-1 to P-226; M-1 to V-225; M-1 to T-224; M-1 to W-223; M-1 to P-222; M-1 to H-221; M-1 to D-220; M-1 to N-219; M-1 to T-218; M-1 to Q-217; M-1 to F-216; M-1 to S-215; M-1 to S-214; M-1 to P-213; M-1 to D-212; M-1 to L-211; M-1 to R-210; M-1 to D-209; M-1 to N-208; M-1 to M-207; M-1 to E-206; M-1 to G-205; M-1 to P-204; M-1 to P-203; M-1 to Q-202; M-1 to V-201; M-1 to I-200; M-1 to N-199; M-1 to E-198; M-1 to L-197; M-1 to S-196; M-1 to R-195; M-1 to N-194; M-1 to E-193; M-1 to L-192; M-1 to P-191; M-1 to D-190; M-1 to G-189; M-1 to Y-188; M-1 to F-187; M-1 to D-186; M-1 to P-185; M-1 to Y-184; M-1 to D-183; M-1 to L-182; M-1 to S-181; M-1 to to G-177; M-1 to F-176; M-1 to K-175; M-1 to Y-174; M-1 to G-173; M-1 to C-172; M-1 to R-171; M-1 to N-170; M-1 to H-169; M-1 to N-168; M-1 to D-167; M-1 to T-166; M-1 to T-165; M-1 to F-164; M-1 to I-163; M-1 to E-162; to R-161; M-1 to Y-160; M-1 to V-159; M-1 to F-158; M-1 to V-157; M-1 to P-156; M-1 to I-155; M-1 to C-154; M-1 to M-153; M-1 to V-152; M-1 to C-151; M-1 to A-150; M-1 to V-149; M-1 to V-148; M-1 to W-147; M-1 to I-146; M-1 to C-145; M-1 to G-144; M-1 to C-143; M-1 to I-142; M-1 to S-141; to M-1 to C-140; M-1 to A-139; M-1 to M-138; M-1 to G-137; M-1 to V-136; M-1 to N-135; M-1 to R-134; M-1 to H-133; M-1 to N-132; M-1 to Q-131; M-1 to C-130; M-1 to W-129; M-1 to I-128; M-1 to P-127; M-1 to K-126; M-1 to F-125; M-1 to V-124; M-1 to V-123; M-1 to L-122; M-1 to C-121; M-1 to R-120; M-1 to D-119; M-1 to L-118; M-1 to S-117; M-1 to I-116; M-1 to A-115; M-1 to T-114; M-1 to L-113; M-1 to L-112; M-1 to F-111; M-1 to V-110; M-1 to S-109; M-1 to A-108; M-1 to F-107; M-1 to M-106; M-1 to N-105; M-1 to L-104; M-1 to V-103; M-1 to I-102; M-1 to I-101; M-1 to S-100; M-1 to P-99; M-1 to I-98; M-1 to L-97; M-1 to K-96; M-1 to C-95; M-1 to L-94; M-1 to F-93; M-1 to R-92; M-1 to G-91; M-1 to Y-90; M-1 to P-89; M-1 to W-88; M-1 to Q-87; M-1 to G-86; M-1 to Q-85; M-1 to L-84; M-1 to A-83; M-1 to L-82; M-1 to H-81; M-1 to A-80; M-1 to L-79; M-1 to S-78; M-1 to F-77; M-1 to P-76; M-1 to L-75; M-1 to S-74; M-1 to L-73; M-1 to C-72; M-1 to C-71; M-1 to L-70; M-1 to L-69; M-1 to D-68; M-1 to A-67; M-1 to L-66; M-1 to T-65; M-1 to L-64; M-1 to H-63; M-1 to L-62; M-1 to F-61; M-1 to W-60; M-1 to I-59; M-1 to T-58; M-1 to N-57; M-1 to V-56; M-1 to T-55; M-1 to R-54; M-1 to Q-53; M-1 to M-52; M-1 to K-51; M-1 to L-50; M-1 to G-49; M-1 to A-48; M-1 to V-47; M-1 to W-46; M-1 to L-45; M-1 to V-44; M-1 to L-43; M-1 to G42; M-1 to N-41; M-1 to G-40; M-1 to P-39; M-1 to L-38; M-1 to G-37; M-1 to L-36; M-1 to L-35; to F-34; M-1 to T-33; M-1 to L-32; M-1 to S-31; M-1 to L-30; M-1 to I-29; M-1 to V-28; M-1 to M-27; M-1 to S-26; M-1 to L-25; M-1 to I-24; M-1 to V-23; M-1 to P-22; M-1 to P-21; M-1 to E-20; M-1 to N-19; M-1 to W-18; M-1 to P-17; M-1 to Q-16; M-1 to S-15; M-1 to L-14; M-1 to L-13; M-1 to D-12; M-1 to T-11; M-1 to S-10; M-1 to N-9; M-1 to T-8; M-1 to E-7; and/or M-1 to A-6; of SEQ ID NO:2.

The present invention also encomapsses antibodies that bind C3a Receptor polypeptides that comprise, or alternatively consist of, an amino acid sequence at least 80%, 85%, 90%, 92%, 95%, 96%, 97%, 98%, 99% or 100% identical to the amino acid sequence described above.

The invention also provides antibodies that bind polypeptides having one or more amino acids deleted from both the amino and the carboxyl termini of a C3a Receptor polypeptide, which may be described generally as having residues $n^1$-$m^1$ of SEQ ID NO:2, where $n^1$ and $m^1$ are integers as described above.

It will be recognized in the art that some amino acid sequence of C3a Receptor can be varied without significant effect of the structure or function of the protein. If such differences in sequence are contemplated, it should be remembered that there will be critical areas on the protein which determine activity. Such areas will usually comprise residues which make up the ligand binding site or which form tertiary structures which affect these domains.

Thus, the invention further includes antibodies that bind variations of the C3a Receptor protein which show substantial C3a Receptor protein activity or which include regions of C3a Receptor such as the protein fragments discussed below. Such mutants include deletions, insertions, inversions, repeats, and type substitution. Guidance concerning which amino acid changes are likely to be phenotypically silent can be found in Bowie, J. U. et al., Science 247:1306-1310 (1990).

Thus, antibodies of the present invention may bind a fragment, derivative, or analog of the polypeptide of SEQ ID NO:2, or that encoded by the cDNA in ATCC deposit 75982. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the C3a Receptor protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

In addition, antibodies of the present invention may bind a C3a Receptor that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 3).

TABLE 3

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of SEQ ID NO:2 and/or any of the polypeptide fragments described herein is 75, 70, 60, 50, 40, 35, 30, 25, 20, 15, 10, 9, 8, 7, 6, 5, 4, 3, 2, 1 or 30-20, 20-15, 20-10, 15-10,10-1, 5-10, 1-5,1-3 or 1-2.

In specific embodiments, the antibodies of the invention bind C3a Receptor polypeptides or fragments or variants thereof (especially a fragment comprising or alternatively consisting of, the secreted, mature form of C3a Receptor), that contains any one or more of the following conservative mutations in C3a Receptor: M1 replaced with M1 replaced with A, G, I, L, S, T, or V; A2 replaced with G, I, L, S, T, M, or V; S3 replaced with A, G, I, L, T, M, or V; F4 replaced with W, or Y; S5 replaced with A, G, I, L, T, M, or V; A6 replaced with G, I, L, S, T, M, or V; E7 replaced with D; T8 replaced with A, G, l, L, S, M, or V; N9 replaced with Q; S10 replaced with A, G, I, L, T, M, or V; T11 replaced with A, G, I, L, S, M, or V; D12 replaced with E; L13 replaced with A, G, I, S, T, M, or V; L14 replaced with A, G, I, S, T, M, or V; S15 replaced with A, G, I, L, T, M, or V; Q16 replaced with N; W18 replaced with F, or Y; N19 replaced with Q; E20 replaced with D; V23 replaced with A, G, I, L, S, T, or M; I24 replaced with A, G, L, S, T, M, or V; L25 replaced with A, G, I, S, T, M, or V; S26 replaced with A, G, I, L, T, M, or V; M27 replaced with A, G, I, L, S, T, or V; V28 replaced with A, G, I, L, S, T, or M; I29 replaced with A, G, L, S, T, M, or V; L30 replaced with A, G, I, S, T, M, or V; S31 replaced with A, G, 1, L, T, M, or V; L32 replaced with A, G, I, S, T, M, or V; T33 replaced with A, G, I, L, S, M, or V; F34 replaced with W, or Y; L35 replaced with A, G, I, S, T, M, or V; L36 replaced with A, G, I, S, T, M, or V; G37 replaced with A, I, L, S, T, M, or V; L38 replaced with A, G, I, S, T, M, or V; G40 replaced with A, I, L, S, T, M, or V; N41 replaced with Q; G42 replaced with A, I, L, S, T, M, or V; L43 replaced with A, G, I, S, T, M, or V; V44 replaced with A, G, I, L, S, T, or M; L45 replaced with A, G, I, S, T, M, or V; W46 replaced with F, or Y; V47 replaced with A, G, I, S, T, or M; A48 replaced with G, I, L, S, T, M, or V; G49 replaced with A, I, L, S, T, M, or V; L50 replaced with A, G, I, S, T, M, or V; K51 replaced with H, or R; M52 replaced with A, G, I, L, S, T, or V; Q53 replaced with N; R54 replaced with H, or K; T55 replaced with A, G, I, L, S, M, or V; V56 replaced with A, G, I, L, S, T, or M; N57 replaced with Q; T58 replaced with A, G, I, L, S, M, or V; I59 replaced with A, G, L, S, T, M, or V; W60 replaced with F, or Y; F61 replaced with W, or Y; L62 replaced with A, G, I, S, T, M, or V; H63 replaced with K, or R; L64 replaced with A, G, I, S, T, M, or V; T65 replaced with A, G, I, L, S, M, or V; L66 replaced with A, G, I, S, T, M, or V; A67 replaced with G, I, L, S, T, M, or V; D68 replaced with E; L69 replaced with A, G, I, S, T, M, or V; L70 replaced with A, G, I, S, T, M, or V; L73 replaced with A, G, I, S, T, M, or V; S74 replaced with A, G, I, L, T, M, or V; L75 replaced with A, G, I, S, T, M, or V; F77 replaced with W, or Y; S78 replaced with A, G, I, L, T, M, or V; L79 replaced with A, G, l, S, T, M, or V; A80 replaced with G, I, L, S, T, M, or V; H81 replaced with K, or R; L82 replaced with A, G, I, S, T, M, or V; A83 replaced with G, I, L, S, T, M, or V; L84 replaced with A, G, I, S, T, M, or V; Q85 replaced with N; G86 replaced with A, I, L, S, T, M, or V; Q87 replaced with N; W88 replaced with F, or Y; Y90 replaced with F, or W; G91 replaced with A, I, L, S, T, M, or V; R92 replaced with H, or K; F93 replaced with W, or Y; L94 replaced with A, G, I, S, T, M, or V; K96 replaced with H, or R; L97 replaced with A, G, I, S, T, M, or V; 198 replaced with A, G, L, S, T, M, or V; S100 replaced with A, G, I, L, T, M, or V; I101 replaced with A, G, L, S, T, M, or V; I102 replaced with A, G, L, S, T, M, or V; V103 replaced with A, G, I, L, S, T, or M; L104 replaced with A, G, I, S, T, M, or V; N105 replaced with Q; M106 replaced with A, G, I, L, S, T, or V; F107 replaced with W, or Y; A108 replaced with G, I, L, S, T, M, or V; S109 replaced with A, G, I, L, T, M, or V; V110 replaced with A, G, I, L, S, T, or M; F111 replaced with W, or Y; L112 replaced with A, G, I, S, T, M, or V; L113 replaced with A, G, I, S, T, M, or V; T114 replaced with A, G, I, L, S, M, or V; A115 replaced with G, I, L, S, T, M, or V; I116 replaced with A, G, L, S, T, M, or V; S117 replaced with A, G, I, L, T, M, or V; L118 replaced with A, G, I, S, T, M, or V; D119 replaced with E; R120 replaced with H, or K; L122 replaced with A, G, I, S, T, M, or V; V123 replaced with A, G, I, L, S, T, or M; V124 replaced with A, G, I, L, S, T, or M; F125 replaced with W, or Y; K126 replaced with H, or R; I128 replaced with A, G, L, S, T, M, or V; W129 replaced with F, or Y; Q131 replaced with N; N132 replaced with Q; H133 replaced with K, or R; R134 replaced with H, or K; N135 replaced with Q; V136 replaced with A, G, I, L, S, T, or M; G137 replaced with A, I, L, S, T, M, or V; M138 replaced with A, G, I, L, S, T, or V; A139 replaced with G, I, L, S, T, M, or V; S141 replaced with A, G, I, L, T, M, or V; I142 replaced with A, G, L, S, T, M, or V; G144 replaced with A, I, L, S, T. M, or V; I146 replaced with A, G, L, S, T, M, or V; W147 replaced with F, or Y; V148 replaced with A, G, I, L, S, T, or M; V149 replaced with A, G, I, L, S, T, or M; A150 replaced with G, I, L, S, T, M, or V; V152 replaced with A, G, I, L, S, T, or M; M153 replaced with A, G, I, L, S, T, or V; I155 replaced with A, G, L, S, T, M, or V; V157 replaced with A, G, I, L, S, T, or M; F158 replaced with W, or Y; V159 replaced with A, G, I, L, S, T, or M; Y160 replaced with F, or W; R161 replaced with H, or K; E162 replaced with D; I163 replaced with A, G, L, S, T, M, or V; F164 replaced with W, or Y; T165 replaced with A, G, I, L, S, M, or V; T166 replaced with A, G, I, L, S, M, or V; D167 replaced with E; N168 replaced with Q; H169 replaced with K, or R; N170 replaced with Q; R171 replaced with H, or K; G173 replaced with A, I, L, S, T, or V; Y174 replaced with F, or W; K175 replaced with H, or R; F176 replaced with W, or Y; G177 replaced with A, I, L, S, T, M, or V; L178 replaced with A, G, I, S, T, M, or V; S179 replaced with A, G, I, L, T, M, or V; S180 replaced with A, G, I, L, T, M, or V; S181 replaced with A, G, I, L, T, M, or V; L182 replaced with A, G, I, S, T, M, or V; D183 replaced with E; Y184 replaced with F, or W; D186 replaced with E; F187 replaced with W, or Y; Y188 replaced with F, or W; G189 replaced with A, I, L, S, T, M, or V; D190 replaced with E; L192 replaced with A, G, I, S, T, M, or V; E193 replaced with D; N194 replaced with Q; R195 replaced with H, or K; S196 replaced with A, G, I, L, T, M, or V; L197 replaced with A, G, I, S, T, M, or V; E198 replaced with D; N199 replaced with Q; I200 replaced with A, G, L, S, T, M, or V; V201 replaced with A, G, I, L, S, T, or M; Q202 replaced with N; G205 replaced with A, I, L, S, T, M, or V; E206 replaced with D; M207 replaced with A, G, I, L, S, T, or V; N208 replaced with Q; D209 replaced with E; R210 replaced with H, or K; L211 replaced with A, G, I, S, T, M, or V; D212 replaced with E; S214 replaced with A, G, I, L, T, M, or V; S215 replaced with A, G, I, L, T, M, or F216 replaced with W, or Y; Q217 replaced with N; T218 replaced with A, G, I, L, S, M, or V; N219 replaced with Q; D220 replaced with E; H221 replaced with K, or R; W223 replaced with F, or Y; T224 replaced with A, G, I, L, S, M, or V; V225 replaced with A, G, I, L, S, T, or M; T227 replaced with A, G, I, L, S, M, or V; V228 replaced with A, G, I, L, S, T, or M; F229 replaced with W, or Y; Q230 replaced with N; Q232 replaced with N; T233 replaced with A, G, I, L, S, M, or V; F234 replaced with W, or Y; Q235 replaced with N; R236 replaced with H, or K; S238 replaced with A, G, I, L, T, M, or V; A239 replaced with G, 1, L, S, T, M, or V; D240 replaced with E; S241 replaced with A, G, I, L, T, M, or V; L242 replaced with A, G, I, S, T, M, or V; R244 replaced with H, or K; G245 replaced with A, I, L, S, T, M, or V; S246 replaced with A, G, I, L, T, M, or V; A247 replaced with G, I, L, S, T, M, or V; R248 replaced with H, or K; L249 replaced with A, G, I, S, T, M, or V; T250 replaced with A, G, I, L, S, M, or V; S251 replaced with A, G, I, L, T, M, or V; Q252 replaced with N; N253 replaced with Q; L254 replaced with A, G, I, S, T, M, or V; Y255 replaced with F, or W; S256 replaced with A, G, I, L, T, M, or V; N257 replaced with Q; V258 replaced with A, G, I, L, S, T, or M; F259 replaced with W, or Y; K260 replaced with H, or R; A262 replaced with G, I, L, S, T, M, or V; D263 replaced with E; V264 replaced with A, G, I, L, S, T, or M; V265 replaced with A, G, I, L, S, T, or M; S266 replaced with A, G, I, L, T, M, or V; K268 replaced with H, or R; I269 replaced with A, G, L, S, T, M, or V; S271 replaced with A, G, I, L, T, M, or V; G272 replaced with A, I, L, S, T, M, or V; F273 replaced with W, or Y; I275 replaced with A, G, L, S, T, M, or V; E276 replaced with D; D277 replaced with E; H278 replaced with K, or R; E279 replaced with D; T280 replaced with A, G, I, L, S, M, or V; S281 replaced with A, G, I, L, T, M, or V; L283 replaced with A, G, I, S, T, M, or V; D284 replaced with E; N285 replaced with Q; S286 replaced with A, G, I, L, T, M, or V; D287 replaced with E; A288 replaced with G, I, L, S, T, M, or V; F289 replaced with W, or Y; L290 replaced with A, G, I, S, T, M, or V; S291 replaced with A, G, I, L, T, M, or V; T292 replaced with A, G, I, L, S, M, or V; H293 replaced with K, or R; L294 replaced with A, G, I, S, T, M, or V; K295 replaced with H, or R; L296 replaced with A, G, I, S, T, M, or V; F297 replaced with W, or Y; S299 replaced with A, G, I, L, T, M, or V; A300 replaced with G, I, L, S, T, M, or V; S301 replaced with A, G, I, L, T, M, or V; S302 replaced with A, G, I, L, T, M, or V; N303 replaced with Q; S304 replaced with A, G, I, L, T, M, or V; F305 replaced with W, or Y; Y306 replaced with F, or W; E307 replaced with D; S308 replaced with A, G, I, L, T, M, or V; E309 replaced with D; L310 replaced with A, G, I, S, T, M, or V; Q312 replaced with N; G313 replaced with A, I, L, S, T, M, or V; F314 replaced with W, or Y; Q315 replaced with N; D316 replaced with E; Y317 replaced with F, or W; Y318 replaced with F, or W; N319 replaced with Q; L320 replaced with A, G, I, S, T, M, or V; G321 replaced with A, I, L, S, T, M, or V; Q322 replaced with N; F323 replaced with W, or Y; T324 replaced with A, G, I, L, S, M, or V; D325 replaced with E; D326 replaced with E; D327 replaced with E; Q328 replaced with N; V329 replaced with A, G, I, L, S, T, or M; T331 replaced with A, G, I, L, S, M, or V; L333 replaced with A, G, I, S, T, M, or V; V334 replaced with A, G, I, L, S, T, or M; A335 replaced with G, I, L, S, T, M, or V; I336 replaced with A, G, L, S, T, M, or V; T337 replaced with A, G, I, L, S, M, or V; I338 replaced with A, G, L, S, T, M, or V; T339 replaced with A, G, I, L, S, M, or V; R340 replaced with H, or K; L341 replaced with A, G, I, S, T, M, or V; V342 replaced with A, G, I, L, S, T, or M; V343 replaced with A, G, I, L, S, T, or M; G344 replaced with A, I, L, S, T, M, or V; F345 replaced with W, or Y; L346 replaced with A, G, I, S, T, M, or V; L347 replaced with A, G, I, S, T, M, or V; S349 replaced with A, G, I, L, T, M, or V; V350 replaced with A, G, I, L, S, T, or M; I351 replaced with A, G, L, S, T, M, or V; M352 replaced with A, G, I, L, S, T, or V; I353 replaced with A, G, L, S, T, M, or V; A354 replaced with G, I, L, S, T, M, or V; Y356 replaced with F, or W; S357 replaced wtih A, G, I, L, T, M, or V; F358 replaced with W, or Y; 1359 replaced with A, G, L, S, T, M, or V; V360 replaced with A, G, I, L, S, T, or M; F361 replaced with W, or Y; R362 replaced with H, or K; M363 replaced with A, G, I, L, S, T, or V; Q364 replaced with N; R365 replaced with H, or K; G366 replaced with A, I, L, S, T, M, or V; R367 replaced with H, or K; F368 replaced with W, or Y; A369 replaced with G, I, L, S, T, M, or V; K370 replaced with H, or R; S371 replaced with A, G, I, L, T, M, or V; Q372 replaced with N; S373 replaced with A, G, I, L, T, M, or V; K374 replaced with H, or R; T375 replaced with A, G, I, L, S, M, or V; F376 replaced with W, or Y; R377 replaced with H, or K; V378 replaced with A, G, I, L, S, T, or M; A379 replaced with G, I, L, S, T, M, or V; V380 replaced with A, G, I, L, S, T, or M; V381 replaced with A, G, I, L, S, T, or M; V382 replaced with A, G, I, L, S, T, or M; V383 replaced with A, G, I, L, S, T, or M; A384 replaced with G, I, L, S, T, M, or V; V385 replaced with A, G, I, L, S, T, or M; F386 replaced with W, or Y; L387 replaced with A, G, I, S, T, M, or V; V388 replaced with A, G, I, L, S, T, or M; W390 replaced with F, or Y; T391 replaced with A, G, I, L, S, M, or V; Y393 replaced with F, or W; H394 replaced with K, or R; I395 replaced with A, G, L, S, T, M, or V; F396 replaced with W, or Y; G397 replaced with A, I, L, S, T, M, or V; V398 replaced with A, G, I, L, S, T, or M; L399 replaced with A, G, I, S, T, M, or V; S400 replaced with A, G, I, L, T, M, or V; L401 replaced with A, G, I, S, T, M, or V; L402 replaced with A, G, I, S, T, M, or V; T403 replaced with A, G, I, L, S, M, or V; D404 replaced with E; E406 replaced with D; T407 replaced with A, G, I, L, S, M, or V; L409 replaced with A, G, I, S, T, M, or V; G410 replaced with A, I, L, S, T, M, or V; K411 replaced with H, or R; T412 replaced with A, G, I, L, S, M, or V; L413 replaced with A, G, I, S, T, M, or V; M414 replaced with A, G, I, L, S, T, or V; S415 replaced with A, G, I, L, T, M, or V; W416 replaced with F, or Y; D417 replaced with E; H418 replaced with K, or R; V419 replaced with A, G, I, L, S, T, or M; I421 replaced with A, G, L, S, T, M, or V; A422 replaced with G, I, L, S, T, M, or V; L423 replaced with A, G, I, S, T, M, or V; A424 replaced with G, I, L, S, T, M, or V; S425 replaced with A, G, I, L, T, M, or V; A426 replaced with G, I, L, S, T, M, or V; N427 replaced with Q; S428 replaced with A, G, I, L, T, M, or V; F430 replaced with W, or Y; N431 replaced with Q; F433 replaced with W, or Y; L434 replaced with A, G, I, S, T, M, or V; Y435 replaced with F, or W; A436 replaced with G, I, L, S, T, M, or V; L437 replaced with A, G, I, S, T, M, or V; L438 replaced with A, G, I, S, T, M, or V; G439 replaced with A, I, L, S, T, M, or V; K440 replaced with H, or R; D441 replaced with E; F442 replaced with W, or Y; R443 replaced with H, or K; K444 replaced with H, or R; K445 replaced with H, or R; A446 replaced with G, I, L, S, T, M, or V; R447 replaced with H, or K; Q448 replaced with N; S449 replaced with A, G, I, L, T, M, or V; I450 replaced with A, G, L, S, T, M, or V; Q451 replaced with N; G452 replaced with A, I, L, S, T, M, or V; I453 replaced with A, G, L, S, T, M, or V; I454 replaced with A, G, I, S, T, M, or V; E455 replaced with D; A456 replaced with G, I, L, S, T, M, or V; A457 replaced with G, I, L, S, T, M, or V; F458 replaced with W, or Y; S459 replaced with A, G, I, L, T, M, or V; E460 replaced with D; E461 replaced with D; L462 replaced with A, G, I, S, T, M, or V; T463 replaced with A, G, I, L, S, M, or V; R464 replaced with H, or K; S465 replaced with A, G, I, L, T, M, or V; T466 replaced with A, G, I, L, S, M, or V; H467 replaced with K, or R; S470 replaced with A, G, I, L, T, M, or V; N471 replaced with Q; N472 replaced with Q; V473 replaced with A, G, I, L, S, T, or M; I474 replaced with A, G, L, S, T, M, or V; S475 replaced with A, G, I, L, T, M, or V; E476 replaced with D; R477 replaced with H, or K; N478 replaced with Q; S479 replaced with A, G, I, L, T, M, or V; T480 replaced with A, G, I, L, S, M, or V; T481 replaced with A, G, I, L, S, M, or V; and/or V482 replaced with A, G, I, L, S, T, or M.

In specific embodiments, the antibodies of the invention bind C3a Receptor polypeptides or fragments or variants thereof (especially a fragment comprising or alternatively consisting of, the extracellular domains of C3a Receptor), that contains any one or more of the following non-conservative mutations in C3a Receptor: M1 replaced with D, E, H, K, R, N, Q, F, W, Y, P, or C; A2 replaced with D, E, H, K, R, N, Q, F, W, Y, P, or C; S3 replaced with D, E, H, K, R, N, Q, F, W, Y, P, or C; F4 replaced with D, E, H, K, R, N, Q, A, G, I, L, S, T, M, V, P, or C; S5 replaced with D, E, H, K, R, N, Q, F, W, Y, P, or C; A6 replaced with D, E, H, K, R, N, Q, F, W, Y, P, or C; E7 replaced with H, K, R, A, G, I, L, S, T, M, V, N, Q, F, W, Y, P, or C; T8 replaced with D, E, H, K, R, N, Q, F, W, Y, P, or C; N9 replaced with D, E, H, K, R, A, G, I, L, S, T, M, V, F, W, Y, P, or C; S10 replaced with D, E, H, K, R, N, Q, F, W, Y, P, or C; T11 replaced with D, E, H, K, R, N, Q, F, W, Y, P, or C; D12 replaced with H, K, R, A, G, I, L, S, T, M, V, N, Q, F, W, Y, P, or C; L13 replaced with D, E, H, K, R, N, Q, F, W, Y, P, or C; L14 replaced with D, E, H, K, R, N, Q, F, W, Y, P, or C; S15 replaced with D, E, H, K, R, N, Q, F, W, Y, P, or C; Q16 replaced with D, E, H, K, R, A, G, I, L, S, T, M, V, F, W, Y, P, or C; P17 replaced with D, E, H, K, R, A, G, I, L, S, T, M, V, N, Q, F, W, Y, or C; W18 replaced with D, E, H, K, R, N, Q, A, G, I, L, S, T, M, V, P, or C; N19 replaced with D, E, H, K, R, A, G, I, L, S, T, M, V, F, W, Y, P, or C; E20 replaced with H, K, R, A, G, I, L, S, T, M, V, N, Q, F, W, Y, P, or C; P21 replaced with D, E, H, K, R, A, G, I, L, S, T, M, V, N, Q, F, W, Y, or C; P22 replaced with D, E, H, K, R, A, G, I, L, S, T, M, V, N, Q, F, W, Y, or C; V23 replaced with D, E, H, K, R, N, Q, F, W, Y, P, or C; I24 replaced with D, E, H, K, R, N, Q, F, W, Y, P, or C; L25 replaced with D, E, H, K, R, N, Q, F, W, Y, P, or C; S26 replaced with D, E, H, K, R, N, Q, F, W, Y, P, or C; M27 replaced with D, E, H, K, R, N, Q, F, W, Y, P, or C; V28 replaced with D, E, H, K, R, N, Q, F, W, Y, P, or C; I29 replaced with D, E, H, K, R, N, Q, F, W, Y, P, or C; L30 replaced with D, E, H, K, R, N, Q, F, W, Y, P, or C; S31 replaced with D, E, H, K, R, N, Q, F, W, Y, P, or C; L32 replaced with D, E, H, K, R, N, Q, F, W, Y, P, or C; T33 replaced with D, E, H, K, R, N, Q, F, W, Y, P, or C; F34 replaced with D, E, H, K, R, N, Q, A, G, I, L, S, T, M, V, P, or C; L35 replaced with D, E, H, K, R, N, Q, F, W, Y, P, or C; L36 replaced with D, E, H, K, R, N, Q, F, W, Y, P, or C; G37 replaced with D, E, H, K, R, N, Q, F, W, Y, P, or C; L38 replaced with D, E, H, K, R, N, Q, F, W, Y, P, or C; P39 replaced with D, E, H, K, R, A, G, I, L, S, T, M, V, N, Q, F, W, Y, or C; G40 replaced with D, E, H, K, R, N, Q, F, W, Y, P, or C; N41 replaced with D, E, H, K, R, A, G, I, L, S, T, M, V, F, W, Y, P, or C; G42 replaced with D, E, H, K, R, N, Q, F, W, Y, P, or C; L43 replaced with D, E, H, K, R, N, Q, F, W, Y, P, or C; V44 replaced with D, E, H, K, R, N, Q, F, W, Y, P, or C; L45 replaced with D, E, H, K, R, N, Q, F, W, Y, P, or C; W46 replaced with D, E, H, K, R, N, Q, A, G, I, L, S, T, M, V, P, or C; V47 replaced with D, E, H, K, R, N, Q, F, W, Y, P, or C; A48 replaced with D, E, H. K, R, N, Q, F, W, Y, P, or C; G49 replaced with D, E, H, K, R, N, Q, F, W, Y, P, or C; L50 replaced with D, E, H, K, R, N, Q, F, W, Y, P, or C; K51 replaced with D, E, A, G, I, L, S, T, M, V, N, Q, F, W, Y, P, or C; M52 replaced with D, E, H, K, R, N, Q, F, W, Y, P, or C; Q53 replaced with D, E, H, K, R, A, G, I, L, S, T, M, V, F, W, Y, P, or C; R54 replaced with D, E, A, G, I, L, S, T, M, V, N, Q, F, W, Y, P, or C; T55 replaced with D, E, H, K, R, N, Q, F, W, Y, P, or C; V56 replaced with D, E, H, K, R, N, Q, F, W, Y, P, or C; N57 replaced with D, E, H, K, R, A, G, I, L, S, T, M, V, F, W, Y, P, or C; T58 replaced with D, E, H, K, R, N, Q, F, W, Y, P, or C; I59 replaced with D, E, H, K, R, N, Q, F, W, Y, P, or C; W60 replaced with D, E, H, K, R, N, Q, A, G, I, L, S, T, M, V, P, or C; F61 replaced with D, E, H, K, R, N, Q, A, G, I, L, S, T, M, V, P, or C; L62 replaced with D, E, H, K, R, N, Q, F, W, Y, P, or C; H63 replaced with D, E, A, G, I, L, S, T, M, V, N, Q, F, W, Y, P, or C; L64 replaced with D, E, H, K, R, N, Q, F, W, Y, P, or C; T65 replaced with D, E, H, K, R, N, Q, F, W, Y, P, or C; L66 replaced with D, E, H, K, R, N, Q, F, W, Y, P, or C; A67 replaced with D, E, H, K, R, N, Q, F, W, Y, P, or C; D68 replaced with H, K, R, A, G, I, L, S, T, M, V, N, Q, F, W, Y, P, or C; L69 replaced with D, E, H, K, R, N, Q, F, W, Y, P, or C; L70 replaced with D, E, H, K, R, N, Q, F, W, Y, P, or C; C71 replaced with D, E, H, K, R, A, G, I, L, S, T, M, V, N, Q, F, W, Y, or P; C72 replaced with D, E, H, K, R, A, G, I, L, S, T, M, V, N, Q, F, W, Y, or P; L73 replaced with D, E, H, K, R, N, Q, F, W, Y, P, or C; S74 replaced with D, E, H, K, R, N, Q, F, W, Y, P, or C; L75 replaced with D, E, H, K, R, N, Q, F, W, Y, P, or C; P76 replaced with D, E, H, K, R, A, G, I, L, S, T, M, V, N, Q, F, W, Y, or C; F77 replaced with D, E, H, K, R, N, Q, A, G, I, L, S, T, M, V, P, or C; S78 replaced with D, E, H, K, R, N, Q, F, W, Y, P, or C; L79 replaced with D, E, H, K, R, N, Q, F, W, Y, P, or C; A80 replaced with D, E, H, K, R, N, Q, F, W, Y, P, or C; H81 replaced with D, E, A, G, I, L, S, T, M, V, N, Q, F, W, Y, P, or C; L82 replaced with D, E, H, K, R, N, Q, F, W, Y, P, or C; A83 replaced with D, E, H, K, R, N, Q, F, W, Y, P, or C; L84 replaced with D, E, H, K, R, N, Q, F, W, Y, P, or C; Q85 replaced with D, E, H, K, R, A, G, I, L, S, T, M, V, F, W, Y, P, or C; G86 replaced with D, E, H, K, R, N, Q, F, W, Y, P, or C; Q87 replaced with D, E, H, K, R, A, G, I, L, S, T, M, V, F, W, Y, P, or C; W88 replaced with D, E, H, K, R, N, Q, A, G, I, L, S, T, M, V, P, or C; P89 replaced with D, E, H, K, R, A, G, I, L, S, T, M, V, N, Q, F, W, Y, or C; Y90 replaced with D, E, H, K, R, N, Q, A, G, I, L, S, T, M, V, P, or C; G91 replaced with D, E, H, K, R, N, Q, F, W, Y, P, or C; R92 replaced with D, E, A, G, I, L, S, T, M, V, N, Q, F, W, Y, P, or C; F93 replaced with D, E, H, K, R, N, Q, A, G, I, L, S, T, M, V, P, or C; L94 replaced with D, E, H, K, R, N, Q, F, W, Y, P, or C; C95 replaced with D, E, H, K, R, A, G, I, L, S, T, M, V, N, Q, F, W, Y, or P; K96 replaced with D, E, A, G, I, L, S, T, M, V, N, Q, F, W, Y, P, or C; L97 replaced with D, E, H, K, R, N, Q, F, W, Y, P, or C; 198 replaced with D, E, H, K, R, N, Q, F, W, Y, P, or C; P99 replaced with D, E, H, K, R, A, G, I, L, S, T, M, V, N, Q, F, W, Y, or C; S100 replaced with D, E, H, K, R, N, Q, F, W, Y, P, or C; I101 replaced with D, E, H, K, R, N, Q, F, W, Y, P, or C; I102 replaced with D, E, H, K, R, N, Q, F, W, Y, P, or C; V103 replaced with D, E, H, K, R, N, Q, F, W, Y, P, or C; L104 replaced with D, E, H, K, R, N, Q, F, W, Y, P, or C; N105 replaced with D, E, H, K, R, A, G, I, L, S, T, M, V, F, W, Y, P, or C; M106 replaced with D, E, H, K, R, N, Q, F, W, Y, P, or C; F107 replaced with D, E, H, K, R, N, Q, A, G, I, L, S, T, M, V, P, or C; A108 replaced with D, E, H, K, R, N, Q, F, W, Y, P, or C; S109 replaced with D, E, H, K, R, N, Q, F, W, Y, P, or C; V110 replaced with D, E, H, K, R, N, Q, F, W, Y, P, or C; F111 replaced with D, E, H, K, R, N, Q, A, G, I, L, S, T, M, V, P, or C; L112 replaced with D, E, H, K, R, N, Q, F, W, Y, P, or C; L113 replaced with D, E, H, K, R, N, Q, F, W, Y, P, or C; T114 replaced with D, E, H, K, R, N, Q, F, W, Y, P, or C; A115 replaced with D, E, H, K, R, N, Q, F, W, Y, P, or C; I116 replaced with D, E, H, K, R, N, Q, F, W, Y, P, or C; S117 replaced with D, E, H, K, R, N, Q, F, W, Y, P, or C; L118 replaced with D, E, H, K, R, N, Q, F, W, Y, P, or C; D119 replaced with H, K, R, A, G, I, L, S, T, M, V, N, Q, F, W, Y, P, or C; R120 replaced with D, E, A, G, I, L, S, T, M, V, N, Q, F, W, Y, P, or C; C121 replaced with D, E, H, K, R, A, G, I, L, S, T, M, V, N, Q, F, W, Y, or P; L122 replaced with D, E, H, K, R, N, Q, F, W, Y, P, or C; V123 replaced with D, E, H, K, R, N, Q, F, W, Y, P, or C; V124 replaced with D, E, H, K, R, N, Q, F, W, Y, P, or C; F125 replaced with D, E, H, K, R, N, Q, A, G, I, L, S, T, M, V, P, or C; K126 replaced with D, E, A, G, I, L, S, T, M, V, N, Q, F, W, Y, P, or C; P127 replaced with D, E, H, K, R, A, G, I, L, S, T, M, V, N, Q, F, W, Y, or C; I128 replaced with D, E, H, K, R, N, Q, F, W, Y, P, or C; W129 replaced with D, E, H, K, R, N, Q, A, G, I, L, S, T, M, V, P, or C; C130 replaced with D, E, H, K, R, A, G, I, L, S, T, M, V, N, Q, F, W, Y, or P Q131 replaced with D, E, H, K, R,A, G, I, L, S, T, M, V, F, W, Y, P, or C; N132 replaced with D, E, H, K, R, A, G, I, L, S, T, M, V, F, W, Y, P, or C; H133 replaced with D, E, A, G, I, L, S, T, M, V, N, Q, F, W, Y, P, or C; R134 replaced with D, E, A, G, I, L, S, T, M, V, N, Q, F, W, Y, P, or C; N135 replaced with D, E, H, K, R, A, G, I, L, S, T, M, V, F, W, Y, P, or C; V136 replaced with D, E, H, K, R, N, Q, F, W, Y, P, or C; G137 replaced with D, E, H, K, R, N, Q, F, W, Y, P, or C; M138 replaced with D, E, H, K, R, N, Q, F, W, Y, P, or C; A139 replaced with D, E, H, K, R, N, Q, F, W, Y, P, or C; C140 replaced with D, E, H, K, R, A, G, I, L, S, T, M, V, N, Q, F, W, Y, or P; S141 replaced with D, E, H, K, R, N, Q, F, W, Y, P, or C; I142 replaced with D, E, H, K, R, N, Q, F, W, Y, P, or C; C143 replaced with D, E, H, K, R, A, G, I, L, S, T, M, V, N, Q, F, W, Y, or P; G144 replaced with D, E, H, K, R, N, Q, F, W, Y, P, or C; C145 replaced with D, E, H, K, R, A, G, I, L, S, T, M, V, N, Q, F, W, Y, or P; I146 replaced with D, E, H, K, R, N, Q, F, W, Y, P, or C; W147 replaced with D, E, H, K, R, N, Q, A, G, I, L, S, T, M, V, P, or C; V148 replaced with D, E, H, K, R, N, Q, F, W, Y, P, or C; V149 replaced with D, E, H, K, R, N, Q, F, W, Y, P, or C; A150 replaced with D, E, H, K, R, N, Q, F, W, Y, P, or C; C151 replaced with D, E, H, K, R, A, G, I, L, S, T, M, V, N, Q, F, W, Y, or P; V152 replaced with D, E, H, K, R, N, Q, F, W, Y, P, or C; M153 replaced with D, E, H, K, R, N, Q, F, W, Y, P, or C; C154 replaced with D, E, H, K, R, A, G, I, L, S, T, M, V, N, Q, F, W, Y, or P; I155 replaced with D, E, H, K, R, N, Q, F, W, Y, P, or C; P156 replaced with D, E, H, K, R, A, G, I, L, S, T, M, V, N, Q, F, W, Y, or C; V157 replaced with D, E, H, K, R, N, Q, F, W, Y, P, or C; F158 replaced with D, E, H, K, R, N, Q, A, G, I, L, S, T, M, V, P, or C; V159 replaced with D, E, H, K, R, N, Q, F, W, Y, P, or C; Y160 replaced with D, E, H, K, R, N, Q, A, G, I, L, S, T, M, V, P, or C; R161 replaced with D, E, A, G, I, L, S, T, M, V, N, Q, F, W, Y, P, or C; E162 replaced with H, K, R, A, G, I, L, S, T, M, V, N, Q, F, W, Y, P, or C; I163 replaced with D, E, H, K, R, N, Q, F, W, Y, P, or C; F164 replaced with D, E, H, K, R, N, Q, A, G, I, L, S, T, M, V, P, or C; T165 replaced with D, E, H, K, R, N, Q, F, W, Y, P, or C; T166 replaced with D, E, H, K, R, N, Q, F, Q, Y, P, or C; D167 replaced with H, K, R, A, G, I, L, S, T, M, V, N, Q, F, W, Y, P, or C; N168 replaced with D, E, H, K, R, A, G, I, L, S, T, M, V, F, W, Y, P, or C; H169 replaced with D, E, A, G, I, L, S, T, M, V, N, Q, F, W, Y, P, or C; N170 replaced with D, E, H, K, R, A, G, I, L, S, T, M, V, F, W, Y, P, or C; R171 replaced with D, E, A, G, I, L, S, T, M, V, N, Q, F, W, Y, P, or C; C172 replaced with D, E, H, K, R, A, G, I, L, S, T, M, V, N, Q, F, W, Y, or P; G173 replaced with D, E, H, K, R, N, Q, F, W, Y, P, or C; Y174 replaced with D, E, H, K, R, N, Q, A, G, I, L, S, T, M, V, P, or C; K175 replaced with D, E, A, G, I, L, S, T, M, V, N, Q, F, W, Y, P, or C; F176 replaced with D, E, H, K, R, N, Q, A, G, I, L, S, T, M, V, P, or C; G177 replaced with D, E, H, K, R, N, Q, F, W, Y, P, or C; L178 replaced with D, E, H, K, R, N, Q, F, W, Y, P, or C; S179 replaced with D, E, H, K, R, N, Q, F, W, Y, P, or C; S180 replaced with D, E, H, K, R, N, Q, F, W, Y, P, or C; S181 replaced with D, E, H, K, R, N, Q, F, W, Y, P, or C; L182 replaced with D, E, H, K, R, N, Q, F, W, Y, P, or C; D183 replaced with H, K, R, A, G, I, L, S, T, M, V, N, Q, F, W, Y, P, or C; Y184 replaced with D, E, H, K, R, N, Q, A, G, I, L, S, T, M, V, P, or C; P185 replaced with D, E, H, K, R, A, G, I, L, S, T, M, V, N, Q, F, W, Y, or C; D186 replaced with H, K, R, A, G, I, L, S, T, M, V, N, Q, F, W, Y, P, or C; F187 replaced with D, E, H, K, R, N, Q, A, G, I, L, S, T, M, V, P, or C; Y188 replaced with D, E, H, K, R, N, Q, A, G, I, L, S, T, M, V, P, or C; G189 replaced with D, E, H, K, R, N, Q, F, W, Y, P, or C; D190 replaced with H, K, R, A, G, I, L, S, T, M, V, N, Q, F, W, Y, P, or C; P191 replaced with D, E, H, K, R, A, G, I, L, S, T, M, V, N, Q, F, W, Y, or C; L192 replaced with D, E, H, K, R, N, Q, F, W, Y, P, or C; E193 replaced with H, K, R, A, G, I, L, S, T, M, V, N, Q, F, W, Y, P, or C; N194 replaced with D, E, H, K, R, A, G, I, L, S, T, M, V, F, W, Y, P, or C; R195 replaced with D, E, A, G, I, L, S, T, M, V, N, Q, F, W, Y, P, or C; S196 replaced with D, E, H, K, R, N, Q, F, W, Y, P, or C; L197 replaced with D, E, H, K, R, N, Q, F, W, Y, P, or C; E198 replaced with H, K, R, A, G, I, L, S, T, M, V, N, Q, F, W, Y, P, or C; N199 replaced with D, E, H, K, R, A, G, I, L, S, T, M, V, F, W, Y, P, or C; 1200 replaced with D, E, H, K, R, N, Q, F, W, Y, P, or C; V201 replaced with D, E, H, K, R, N, Q, F, W, Y, P, or C; Q202 replaced with D, E, H, K, R, A, G, I, L, S, T, M, V, F, W, Y, P, or C; P203 replaced with D, E, H, K, R, A, G, I, L, S, T, M, V, N, Q, F, W, Y, or C; P204 replaced with D, E, H, K, R, A, G, I, L, S, T, M, V, N, Q, F, W, Y, or C; G205 replaced with D, E, H, K, R, N, Q, F, W, Y, P, or C; E206 replaced with H, K, R, A, G, I, L, S, T, M, V, N, Q, F, W, Y, P, or C; M207 replaced with D, E, H, K, R, N, Q, F, W, Y, P, or C; N208 replaced with D, E, H, K, R, A, G, I, L, S, T, M, V, F, W, Y, P or C; D209 replaced with H, K, R, A, G, I, L, S, T, M, V, N, Q, F, W, Y, P, or C; R210 replaced with D, E, A, G, I, L, S, T, M, V, N, Q, F, W, Y, P, or C; L211 replaced with D, E, H, K, R, N, Q, F, W, Y, P, or C; D212 replaced with H, K, R, A, G, I, L, S, T, M, V, N, Q, F, W, Y, P, or C; P213 replaced with D, E, H, K, R, A, G, I, L, S, T, M, V, N, Q, F, W, Y, or C; S214 replaced with D, E, H, K, R, N, Q, F, W, Y, P, or C; S215 replaced with D, E, H, K, R, N, Q, F, W, Y, P, or C; F216 replaced with D, E, H, K, R, N, Q, A, G, I, L, S, T, M, V, P, or C; Q217 replaced with D, E, H, K, R, A, G, I, L, S, T, M, V, F, W, Y, P, or C; T218 replaced with D, E, H, K, R, N, Q, F, W, Y, P, or C; N219 replaced with D, E, H, K, R, A, G, I, L, S, T, M, V, F, W, Y, P, or C; D220 replaced with H, K, R, A, G, I, L, S, T, M, V, N, Q, F, W, Y, P, or C; H221 replaced with D, E, A, G, I, L, S, T, M, V, N, Q, F, W, Y, P, or C; P222 replaced with D, E, H, K, R, A, G, I, L, S, T, M, V, N, Q, F, W, Y, or C; W223 replaced with D, E, H, K, R, N, Q, A, G, I, L, S, T, M, V, P, or C; T224 replaced with D, E, H, K, R, N, Q, F, W, Y, P, or C; V225 replaced with D, E, H, K, R, N, Q, F, W, Y, P, or C; P226 replaced with D, E, H, K, R, A, G, I, L, S, T, M, V, N, Q, F, W, Y, or C; T227 replaced with D, E, H, K, R, N, Q, F, W, Y, P, or C; V228 replaced with D, E, H, K, R, N, Q, F, W, Y, P, or C; F229 replaced with D, E, H, K, R, N, Q, A, G, I, L, S, T, M, V, P, or C; Q230 replaced with D, E, H, K, R, A, G, I, L, S, T, M, V, F, W, Y, P, or C; P231 replaced with D, E, H, K, R, A, G, I, L, S, T, M, V, N, Q, F, W, Y, or C; Q232 replaced with D,E, H, K, R, A, G, I, L, S, T, M, V, F, W, Y, P, or C; T233 replaced with D, E, H, K, R, N, Q, F, W, Y, P, or C; F234 replaced with D, E, H, K, R, N, Q, A, G, I, L, S, T, M, V, P, or C; Q235 replaced with D, E, H, K, R, A, G, I, L, S, T, M, V, F, W, Y, P, or C; R236 replaced with D, E, A, G, I, L, S, T, M, V, N, Q, F, W, Y, P, or C; P237 replaced with D, E, H, K, R, A, G, I, L, S, T, M, V, N, Q, F, W, Y, or C; S238 replaced with D, E, H. K, R, N, Q, F, W, Y, P, or C; A239 replaced with D, E, H, K, R, N, Q, F, W, Y, P, or C; D240 replaced with H, K, R, A, G, I, L, S, T, M, V, N, Q, F, W, Y, P, or C; S241 replaced with D, E, H, K, R, N, Q, F, W, Y, P, or C; L242 replaced with D, E, H, K, R, N, Q, F, W, Y, P, or C; P243 replaced with D, E, H, K, R, A, G, I, L, S, T, M, V, N, Q, F, W, Y, or C; R244 replaced with D, E, A, G, I, L, S, T, M, V, N, Q, F, W, Y, P, or C; G245 replaced with D, E, H, K, R, N, Q, F, W, Y, P, or C; S246 replaced with D, E, H, K, R, N, Q, F, W, Y, P, or C; A247 replaced with D, E, H, K, R, N, Q, F, W, Y, P, or C; R248 replaced with D, E, A, G, I, L, S, T, M, V, N, Q, F, W, Y, P, or C; L249 replaced with D, E, H, K, R, N, Q, F, W, Y, P, or C; T250 replaced with D, E, H, K, R, N, Q, F, W, Y, P, or C; S251 replaced with D, E, H, K, R, N, Q, F, W, Y, P, or C; Q252 replaced with D, E, H, K, R, A, G, I, L, S, T, M, V, F, W, Y, P, or C; N253 replaced with D, E, H, K, R, A, G, I, L, S, T, M, V, F, W, Y, P, or C; L254 replaced with D, E, H, K, R, N, Q, F, W, Y, P, or C; Y255 replaced with D, E, H, K, R, N, Q, A, G, I, L, S, T, M, V, P, or C; S256 replaced with D, E, H, K, R, N, Q, F, W, Y, P, or C; N257 replaced with D, E, H, K, R, A, G, I, L, S, T, M, V, F, W, Y, P, or C; V258 replaced with D, E, H, K, R, N, Q, F, W, Y, P, or C; F259 replaced with D, E, H. K, R. N, Q, A, G, I, L, S, T, M, V, P, or C; K260 replaced with D, E, A, G, I, L, S, T, M, V, N, Q, F, W, Y, P, or C; P261 replaced with D, E, H, K, R, A, G, I, L, S, T, M, V, N, Q, F, W, Y, or C; A262 replaced with D, E, H, K, R, N, Q, F, W, Y, P, or C; D263 replaced with H, K, R, A, G, I, L, S, T, M, V, N, Q, F, W, Y, P, or C; V264 replaced with D, E, H, K, R, N, Q, F, W, Y, P, or C; V265 replaced with D, E, H, K, R, N, Q, F, W, Y, P, or C; S266 replaced with D, E, H, K, R, N, Q, F, W, Y, P, or C; P267 replaced with D, E, H, K, R, A, G, I, L, S, T, M, V, N, Q, F, W, Y, or C; K268 replaced with D, E, A, G, I, L, S, T, M, V, N, Q, F, W, Y, P, or C; I269 replaced with D, E, H, K, R, N, Q, F, W, Y, P, or C; P270 replaced with D, E, H, K, R, A, G, I, L, S, T, M, V, N, Q, F, W, Y, or C; S271 replaced with D, E, H, K, R, N, Q, F, W, Y, P, or C; G272 replaced with D, E, H, K, R, N, Q, F, W, Y, P, or C; F273 replaced with D, E, H, K, R, N, Q, A, G, I, L, S, T, M, V, P, or C; P274 replaced with D, E, H, K, R, A, G, I, L, S, T, M, V, N, Q, F, W, Y, or C; I275 replaced with D, E, H, K, R, N, Q, F, W, Y, P, or C; E276 replaced with H, K, R, A, G, I, L, S, T, M, V, N, Q, F, W, Y, P, or C; D277 replaced with H, K, R, A, G, I, L, S, T, M, V, N, Q, F, W, Y, P, or C; H278 replaced with D, E, A, G, I, L, S, T, M, V, N, Q, F, W, Y, P, or C; E279 replaced with H, K, R, A, G, I, L, S, T, M, V, N, Q, F, W, Y, P, or C; T280 replaced with D, E, H, K, R, N, Q, F, W, Y, P, or C; S281 replaced with D, E, H, K, R, N, Q, F, W, Y, P, or C; P282 replaced with D, E, H, K, R, A, G, I, L, S, T, M, V, N, Q, F, W, Y, or C; L283 replaced with D, E, H, K, R, N, Q, F, WY, P, or C; D284 replaced with H, K, R, A, G, I, L, S, T, M, V, N, Q, F, W, Y, P, or C; N285 replaced with D, E, H, K, R, A, G, I, L, S, T, M, V, F, W, Y, P, or C; S286 replaced with D, E, H, K, R, N, Q, F, W, Y, P, or C; D287 replaced with H, K, R, A, G, I, L, S, T, M, V, N, Q, F, W, Y, P, or C; A288 replaced with D, E, H, K, R, N, Q, F, W, Y, P, or C; F289 replaced with D, E, H, K, R, N, Q, A, G, I, L, S, T, M, V, P, or C; L290 replaced with D, E, H, K, R, N, Q, F, W, Y, P, or C; S291 replaced with D, E, H, K, R, N, Q, F, W, Y, P, or C; T292 replaced with D, E, H, K, R, N, Q, F, W, Y, P, or C; H293 replaced with D, E, A, G, I, L, S, T, M, V, N, Q, F, W, Y, P, or C; L294 replaced with D, E, H, K, R, N, Q, F, W, Y, P, or C; K295 replaced with D, E, H, K, R, N, Q, I, L, S, T, M, V, N, Q, F, W, Y, P, or C; L296 replaced with D, E, H, K, R, N, Q, F, W, Y, P, or C; F297 replaced with D, E, H, K, R, N, Q, A, G, I, L, S, T, M, V, P, or C; P298 replaced with D, E, H, K, R, A, G, I, L, S, T, M, V, N, Q, F, W, Y, or C; S299 replaced with D, E, H, K, R, N, Q, F, W, Y, P, or C; A300 replaced with D, E, H, K, R, N, Q, F, W, Y, P, or C; S301 replaced with D, E, H, K, R, N, Q, F, W, Y, P, or C; S302 replaced with D, E, H, K, R, N, Q, F, W, Y, P, or C; N303 replaced with D, E, H, K, R, A, G, I, L, S, T, M, V, F, W, Y, P, or C; S304 replaced with D, E, H, K, R, N, Q, F, W, Y, P, or C; F305 replaced with D, E, H, K, R, N, Q, A, G, I, L, S, T, M, V, P, or C; Y306 replaced with D, E, H, K, R, N, Q, A, G, I, L, S, T, M, V, P, or C; E307 replaced with H, K, R, A, G, I, L, S, T, M, V, N, Q, F, W, Y, P, or C; S308 replaced with D, E, H, K, R, N, Q, F, W, Y, P, or C; E309 replaced with H, K, R, A, G, I, L, S, T, M, V, N, Q, F, W, Y, P, or C; L310 replaced with D, E, H, K, R, N, Q, F, W, Y, P, or C; P311 replaced with D, E, H, K, R, A, G, I, L, S, T, M, V, N, Q, F, W, Y, or C; Q312 replaced with D, E, H, K, R, A, G, I, L, S, T, M, V, F, W, Y, P, or C; G313 replaced with D, E, H, K, R, N, Q, F, W, Y, P, or C; F314 replaced with D, E, H, K, R, N, Q, A, G, I, L, S, T, M, V, P, or C; Q315 replaced with D, E, H, K, R, A, G, I, L, S, T, M, V, F, W, Y, P, or C; D316 replaced with H, K, R, A, G, I, L, S, T, M, V, N, Q, F, W, Y, P, or C; Y317 replaced with D, E, H, K, R, N, Q, A, G, I, L, S, T, M, V, P, or C; Y318 replaced with D, E, H, K, R, N, Q, A, G, I, L, S, T, M, V, P, or C; N319 replaced with D, E, H, K, R, A, G, I, L, S, T, M, V, F, W, Y, P, or C; L320 replaced with D, E, H, K, R, N, Q, F, W, Y, P, or C; G321 replaced with D, E, H, K, R, N, Q, F, W, Y, P, or C; Q322 replaced with D, E, H, K, R, A, G, I, L, S, T, M, V, F, W, Y, P, or C; F323 replaced with D, E, H. K, R. N, Q, A, G, I, L, S, T, M, V, P, or C; T324 replaced with D, E, H, K, R, N, Q, F, W, Y, P, or C; D325 replaced with H, K, R, A, G, I, L, S, T, M, V, N, Q, F, W, Y, P, or C; D326 replaced with H, K, R, A, G, I, L, S, T, M, V, N, Q, F, W, Y, P, or C; D327 replaced with H, K, R, A, G, I, L, S, T, M, V, N, Q, F, W, Y, P, or C; Q328 replaced with D, E, H, K, R, A, G, I, L, S, T, M, V, F, W, Y, P, or C; V329 replaced with D, E, H, K, R, N, Q, F, W, Y, P, or C; P330 replaced with D, E, H, K, R, A, G, I, L, S, T, M, V, N, Q, F, W, Y, or C; T331 replaced with D, E, H, K, R, N, Q, F, W, Y, P, or C; P332 replaced with D, E, H, K, R, A, G, I, L, S, T, M, V, N, Q, F, W, Y, or C; L333 replaced with D, E, H, K, R, N, Q, F, W, Y, P, or C; V334 replaced with D, E, H, K, R, N, Q, F, W, Y, P, or C; A335 replaced with D, E, H, K, R, N, Q, F, W, Y, P, or C; I336 replaced with D, E, H, K, R, N, Q, F, W, Y, P, or C; T337 replaced with D, E, H, K, R, N, Q, F, W, Y, P, or C; 1338 replaced with D, E, H, K, R, N, Q, F, W, Y, P, or C; T339 replaced with D, E, H, K, R, N, Q, F, W, Y, P, or C; R340 replaced with D, E, A, G, I, L, S, T, M, V, N, Q, F, W, Y, P, or C; L341 replaced with D, E, H, K, R, N, Q, F, W, Y, P, or C; V342 replaced with D, E, H, K, R, N, Q, F, W, Y, P, or C; V343 replaced with D, E, H, K, R, N, Q, F, W, Y, P, or C; G344 replaced with D, E, H, K, R, N, Q, F, W, Y, P, or C; F345 replaced with D, E, H, K, R, N, Q, A, G, I, L, S, T, M, V, P, or C; L346 replaced with D, E, H, K, R, N, Q, F, W, Y, P, or C; L347 replaced with D, E, H, K, R, N, Q, F, W, Y, P, or C; P348 replaced with D, E, H, K, R, A, G, I, L, S, T, M, V, N, Q, F, W, Y, or C; S349 replaced with D, E, H, K, R, N, Q, F, W, Y, P, or C; V350 replaced with D, E, H, K, R, N, Q, F, W, Y, P, or C; 1351 replaced with D, E, H, K, R, N, Q, F, W, Y, P, or C; M352 replaced with D, E, H, K, R, N, Q, F, W, Y, P, or C; I353 replaced with D, E, H, K, R, N, Q, F, W, Y, P, or C; A354 replaced with D, E, H, K, R, N, Q, F, W, Y, P, or C; C355 replaced with D, E, H, K, R, A, G, I, L, S, T, M, V, N, Q, F, W, Y, or P; Y356 replaced with D, E, H, K, R, N, Q, A, G, I, L, S, T, M, V, P, or C; S357 replaced with D, E, H, K, R, N, Q, F, W, Y, P, or C; F358 replaced with D, E, H, K, R, N, Q, A, G, I, L, S, T, M, V, P, or C; I359 replaced with D, E, H, K, R, N, Q, F, W, Y, P, or C; V360 replaced with D, E, H, K, R, N, Q, F, W, Y, P, or C; F361 replaced with D, E, H, K, R, N, Q, A, G, I, L, S, T, M, V, P, or C; R362 replaced with D, E, A, G, I, L, S, T, M, V, N, Q, F, W, Y, P, or C; M363 replaced with D, E, H, K, R, N, Q, F, W, Y, P, or C; Q364 replaced with D, E, H, K, R, A, G, I, L, S, T, M, V, F, W, Y, P, or C; R365 replaced with D, E, A, G, I, L, S, T, M, V, N, Q, F, W, Y, P, or C; G366 replaced with D, E, H, K, R, N, Q, F, W, Y, P, or C; R367 replaced with D, E, A, G, I, L, S, T, M, V, N, Q, F, W, Y, P, or C; F368 replaced with D, E, H, K, R, N, Q, A, G, I, L, S, T, M, V, P, or C; A369 replaced with D, E, H, K, R, N, Q, F, W, Y, P, or C; K370 replaced with D, E, A, G, I, L, S, T, M, V, N, Q, F, W, Y, P, or C; S371 replaced with D, E, H, K, R, N, Q, F, W, Y, P, or C; Q372 replaced with D, E, H, K, R, A, G, I, L, S, T, M, V, F, W, Y, P, or C; S373 replaced with D, E, H, K, R, N, Q, F, W, Y, P, or C; K374 replaced with D, E, A, G, I, L, S, T, M, V, N, Q, F, W, Y, P, or C; T375 replaced with D, E, H, K, R, N, Q, F, W, Y, P, or C; F376 replaced with D, E, H, K, R, N, Q, A, G, I, L, S, T, M, V, P, or C; R377 replaced with D, E, A, G, I, L, S, T, M, V, N, Q, F, W, Y, P, or C; V378 replaced with D, E, H, K, R, N, Q, F, W, Y, P, or C; A379 replaced with D, E, H, K, R, N, Q, F, W, Y, P, or C; V380 replaced with D, E, H, K, R, N, Q, F, W, Y, P, or C; V381 replaced with D, E, H, K, R, N, Q, F, W, Y, P, or C; V382 replaced with D, E, H, K, R, N, Q, F, W, Y, P, or C; V383 replaced with D, E, H, K, R, N, Q, F, W, Y, P, or C; A384 replaced with D, E, H, K, R, N, Q, F, W, Y, P, or C; V385 replaced with D, E, H, K, R, N, Q, F, W, Y, P, or C; F386 replaced with D, E, H, K, R, N, Q, A, G, I, L, S, T, M, V, P, or C; L387 replaced with D, E, H, K, R, N, Q, F, W, Y, P, or C; V388 replaced with D, E, H, K, R, N, Q, F, W, Y, P, or C; C389 replaced with D, E, H, K, R, A, G, I, L, S, T, M, V, N, Q, F, W, Y, or P; W390 replaced with D, E, H, K, R, N, Q, A, G, I, L, S, T, M, V, P, or C; T391 replaced with D, E, H, K, R, N, Q, F, W, Y, P, or C; P392 replaced with D, E, H, K, R, A, G, I, L, S, T, M, V, N, Q, F, W, Y, or C; Y393 replaced with D, E, H, K, R, N, Q, A, G, I, L, S, T, M, V, P, or C; H394 replaced with D, E, A, G, I, L, S, T, M, V, N, Q, F, W, Y, P, or C; I395 replaced with D, E, H, K, R, N, Q, F, W, Y, P, or C; F396 replaced with D, E, H, K, R, N, Q, A, G, I, L, S, T, M, V, P, or C; G397 replaced with D, E, H, K, R, N, Q, F, W, Y, P, or C; V398 replaced with D, E, H, K, R, N, Q, F, W, Y, P, or C; L399 replaced with D, E, H, K, R, N, Q, F, W, Y, P, or C; S400 replaced with D, E, H, K, R, N, Q, F, W, Y, P, or C; L401 replaced with D, E, H, K, R, N, Q, F, W, Y, P, or C; L402 replaced with D, E, H, K, R, N, Q, F, W, Y, P, or C; T403 replaced with D, E, H, K, R, N, Q, F, W, Y, P, or C; D404 replaced with H, K, R, A, G, I, L, S, T, M, V, N, Q, F, W, Y, P, or C; P405 replaced with D, E, H, K, R, A, G, I, L, S, T, M, V, N, Q, F, W, Y, or C; E406 replaced with H, K, R, A, G, I, L, S, T, M, V, N, Q, F, W, Y, P, or C; T407 replaced with D, E, H, K, R, N, Q, F, W, Y, P, or C; P408 replaced with D, E, H, K, R, A, G, I, L, S, T, M, V, N, Q, F, W, Y, or C; L409 replaced with D, E, H, K, R, N, Q, F, W, Y, P, or C; G410 replaced with D, E, H, K, R, N, Q, F, W, Y, P, or C; K411 replaced with D, E, A, G, I, L, S, T, M, V, N, Q, F, W, Y, P, or C; T412 replaced with D, E, H, K, R, N, Q, F, W, Y, P, or C; L413 replaced with D, E, H, K, R, N, Q, F, W, Y, P, or C; M414 replaced with D, E, H, K, R, N, Q, F, W, Y, P, or C; S415 replaced with D, E, H, K, R, N, Q, F, W, Y, P, or C; W416 replaced with D, E, H, K, R, R, Q, A, G, I, L, S, T, M, V, P, or C; D417 replaced with H, K, R, A, G, I, L, S, T, M, V, N, Q, F, W, Y, P, or C; H418 replaced with D, E, A, G, I, L, S, T, M, V, N, Q, F, W, Y, P, or C; V419 replaced with D, E, H, K, R, N, Q, F, W, Y, P, or C; C420 replaced with D, E, H, K, R, A, G, I, L, S, T, M, V, N, Q, F, W, Y, or P; I421 replaced with D, E, H, K, R, N, Q, F, W, Y, P, or C; A422 replaced with D, E, H, K, R, N, Q, F, W, Y, P, or C; L423 replaced with D, E, H, K, R, N, Q, F, W, Y, P, or C; A424 replaced with D, E, H, K, R, N, Q, F, W, Y, P, or C; S425 replaced with D, E, H, K, R, N, Q, F, W, Y, P, or C; A426 replaced with D, E, H, K, R, N, Q, F, W, Y, P, or C; N427 replaced with D, E, H, K, R, A, G, I, L, S, T, M, V, F, W, Y, P, or C; S428 replaced with D, E, H, K, R, N, Q, F, W, Y, P, or C; C429 replaced with D, E, H, K, R, A, G, I, L, S, T, M, V, N, Q, F, W, Y, or P; F430 replaced with D, E, H, K, R, N, Q, A, G, I, L, S, T, M, V, P, or C; N431 replaced with D, E, H, K, R, A, G, I, L, S, T, M, V, F, W, Y, P, or C; P432 replaced with D, E, H, K, R, A, G, I, L, S, T, M, V, N, Q, F, W, Y, or C; F433 replaced with D, E, H, K, R, N, Q, A, G, I, L, S, T, M, V, P, or C; L434 replaced with D, E, H, K, R, N, Q, F, W, Y, P, or C; Y435 replaced with D, E, H, K, R, N, Q, A, G, I, L, S, T, M, V, P, or C; A436 replaced with D, E, H. K, R. N. Q, F, W, Y, P, or C; L437 replaced with D, E, H, K, R, N, Q, F, W, Y, P, or C; L438 replaced with D, E, H, K, R, N, Q, F, W, Y, P, or C; G439 replaced with D, E, H, K, R, N, Q, F, W, Y, P, or C; K440 replaced with D, E, A, G, I, L, S, T, M, V, N, Q, F, W, Y, P, or C; D441 replaced with H, K, R, A, G, I, L, S, T, M, V, N, Q, F, W, Y, P, or C; F442 replaced with D, E, H, K, R, N, Q, A, G, I, L, S, T, M, V, P, or C; R443 replaced with D, E, A, G, I, L, S, T, M, V, N, Q, F, W, Y, P, or C; K444 replaced with D, E, A, G, I, L, S, T, M, V, N, Q, F, W, Y, P, or C; K445 replaced with D, E, A, G, I, L, S, T, M, V, N, Q, F, W, Y, P, or C; A446 replaced with D, E, H, K, R, N, Q, F, W, Y, P, or C; R447 replaced with D, E, A, G, I, L, S, T, M, V, N, Q, F, W, Y, P, or C; Q448 replaced with D, E, H, K, R, A, G, I, L, S, T, M, V, F, W, Y, P, or C; S449 replaced with D, E, H, K, R, N, Q, F, W, Y, P, or C; I450 replaced with D, E, H, K, R, N, Q, F, W, Y, P, or C; Q451 replaced with D, E, H, K, R, A, G, I, L, S, T, M, V, F, W, Y, P, or C; G452 replaced with D, E, H, K, R, N, Q, F, W, Y, P, or C; I453 replaced with D, E, H, K, R, N, Q, F, W, Y, P, or C; L454 replaced with D, E, H, K, R, N, Q, F, W, Y, P, or C; E455 replaced with H, K, R, A, G, I, L, S, T, M, V, N, Q, F, W, Y, P, or C; A456 replaced with D, E, H, K, R, N, Q, F, W, Y, P, or C; A457 replaced with D, E, H, K, R, N, Q, F, W, Y, P, or C; F458 replaced with D, E, H, K, R, N, Q, A, G, I, L, S, T, M, V, P, or C; S459 replaced with D, E, H, K, R, N, Q, F, W, Y, P, or C; E460 replaced with H, K, R, A, G, I, L, S, T, M, V, N, Q, F, W, Y, P, or C; E461 replaced with H, K, R, A, G, I, L, S, T, M, V, N, Q, F, W, Y, P, or C; I462 replaced with D, E, H, K, R, N, Q, F, W, Y, P, or C; T463 replaced with D, E, H, K, R, N, Q, F, W, Y, P, or C; R464 replaced with D, E, A, G, I, L, S, T, M, V, N, Q, F, W, Y, P, or C; S465 replaced with D, E, H, K, R, N, Q, F, W, Y, P, or C; T466 replaced with D, E, H, K, R, N, Q, F, W, Y, P, or C; H467 replaced with D, E, A, G, I, L, S, T, M, V, N, Q, F, W, Y, P, or C; C468 replaced with D, E, H, K, R, A, G, I, L, S, T, M, V, N, Q, F, W, Y, or P; P469 replaced with D, E, H, K, R, A, G, I, L, S, T, M, V, N, Q, F, W, Y, or C; S470 replaced with D, E, H, K, R, N, Q, F, W, Y, P, or C; N471 replaced with D, E, H, K, R, A, G, I, L, S, T, M, V, F, W, Y, P, or C; N472 replaced with D, E, H, K, R, A, G, I, L, S, T, M, V, F, W, Y, P, or C; V473 replaced with D, E, H, K, R, N, Q, F, W, Y, P, or C; I474 replaced with D, E, H, K, R, N, Q, F, W, Y, P, or C; S475 replaced with D, E, H, K, R, N, Q, F, W, Y, P, or C; E476 replaced with H, K, R, A, G, I, L, S, T, M, V, N, Q, F, W, Y, P, or C; R477 replaced with D, E, A, G, I, L, S, T, M, V, N, Q, F, W, Y, P, or C; N478 replaced with D, E, H, K, R, A, G, I, L, S, T, M, V, F, W, Y, P, or C; S479 replaced with D, E, H, K, R, N, Q, F, W, Y, P, or C; T480 replaced with D, E, H, K, R, N, Q, F, W, Y, P, or C; T481 replaced with D, E, H, K, R, N, Q, F, W, Y, P, or C; and/or V482 replaced with D, E, H, K, R, N, Q, F, W, Y, P, or C of SEQ ID NO:2.

Amino acids in the C3a Receptor protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as ligand (e.g., C3a anaphlytoxin, amino acids 672-748 of GenBank Accession Number AAA85332.1) binding or in vitro, or in vivo; the ability to induce calcium flux in C3a Receptor expressing cells upon exposure to C3a. the ability to cause contraction of airway smooth muscle upon interaction with C3a; the ability to activate, induce chemotaxis of promote degranulation of mast cells and/or granulocytes such as eosinophils. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of C3a Receptor that are essential for C3a Receptor function. In other preferred embodiments, antibodies of the present invention bind regions of C3a Receptor that are essential for C3a Receptor function and inhibit or abolish C3a Receptor function. In other preferred embodiments, antibodies of the present invention bind regions of C3a Receptor that are essential for C3a Receptor function and enhance C3a Receptor function.

Additionally, protein engineering may be employed to improve or alter the characteristics of C3a Receptor polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified C3a Receptor polypeptides.

Non-naturally occurring variants of C3a Receptor may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses antibodies that bind C3a Receptor derivatives and analogs that have one or more amino acid residues deleted, added, or substituted to generate C3a Receptor polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the C3a Receptor polypeptides and/or an amino acid deletion at the second position of any one or more such recognition sequences will prevent glycosylation of C3a Receptor at the modified tripeptide sequence (see, e.g., Miyajimo et al., *EMBO J.* 5(6): 1193-1197). Additionally, one or more of the amino acid residues of C3a Receptor polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of, the polypeptide encoded by the deposited cDNAs (the deposit having ATCC Accession Number 75982) or a polypeptide comprising, or alternatively, consisting of, the polypeptide of SEQ ID NO:2 as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA clones (the deposit having ATCC Accession Number 75982), the polypeptide of SEQ ID NO:2, and portions of such polypeptides comprising at least 30 amino acids and more preferably at least 50 amino acids.

By a polypeptide having an amino acid sequence at least, for example, 95% "identical" to a reference amino acid sequence of a C3a Receptor polypeptide is intended that the amino acid sequence of the polypeptide is identical to the reference sequence except that the polypeptide sequence may include up to five amino acid alterations per each 100 amino acids of the reference amino acid of the C3a Receptor polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or any-where between those terminal positions, interspersed either individually among residues in the reference sequence or in one or more contiguous groups within the reference sequence.

Antibodies or antibody compositions of the present invention may be used as a practical matter, whether any particular polypeptide is at least 90%, 95%, 96%, 97%, 98% or 99% identical to, for instance, the amino acid sequence shown in SEQ ID NO:2 or to the amino acid sequence encoded by deposited CDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to antibodies that bind proteins containing polypeptides at least 90%, 95%, 96%, 97%, 98% or 99% identical to the C3a Receptor polypeptide sequence set forth herein as $n^1$-482, 1-$m^1$, and $n^1$-$m^1$. In preferred embodiments, the application encomapsses antibodies that bind proteins containing polypeptides at least 90%, 95%, 96%, 97%, 98% or 99% identical to polypeptides having the amino acid sequence of the specific C3a Receptor N- and C-terminal deletions recited herein.

In certain preferred embodiments, antibodies of the invention bind C3a Receptor fusion proteins as described above wherein the C3a Receptor portion of the fusion protein are those described as $n^1$-482, 1-$m^1$, and $n^1$-$m^1$ herein.

C3a Receptor proteins may be either monomers (e.g., the naturally occurring C3a Receptor is monomeric) or multimers (e.g., dimers, trimers, tetramers, and higher multimers that usually are the result of recombinant protein technology). Accordingly, the present invention relates to antibodies that bind C3a Receptor proteins found as monomers or as part of multimers. In specific embodiments, antibodies of the invention bind C3a Receptor monomers, dimers, trimers or tetramers. In additional embodiments, antibodies of the invention bind at least dimers, at least trimers, or at least tetramers containing one or more C3a Receptor polypeptides.

Antibodies of the invention may bind C3a Receptor homomers or heteromers. As used herein, the term homomer, refers to a multimer containing only C3a Receptor proteins of the invention (including C3a Receptor fragments, variants, and fusion proteins, as described herein). These homomers may contain C3a Receptor proteins having identical or different polypeptide sequences. In a specific embodiment, a homomer of the invention is a multimer containing only C3a Receptor proteins having an identical polypeptide sequence. In another specific embodiment, antibodies of the invention bind C3a Receptor homomers containing C3a Receptor proteins having different polypeptide sequences. In specific embodiments, antibodies of the invention bind a C3a Receptor homodimer (e.g., containing C3a Receptor proteins having identical or different polypeptide sequences) or a homotrimer (e.g., containing C3a Receptor proteins having identical or different polypeptide sequences). In additional embodiments, antibodies of the invention bind at least a homodimer, at least a homotrimer, or at least a homotetramer of C3a Receptor.

As used herein, the term heteromer refers to a multimer containing heterologous proteins (i.e., proteins containing polypeptide sequences that do not correspond to C3a Receptor polypeptide sequences) in addition to the C3a Receptor proteins of the invention. In a specific embodiment, antibodies of the invention bind a heterodimer, a heterotrimer, or a heterotetramer. In additional embodiments, the antibodies of the invention bind at least a heterodimer, at least a heterotrimer, or at least a heterotetramer containing one or more C3a Receptor polypeptides.

Antibodies of the invention may bind multimers that are the result of hydrophobic, hydrophilic, ionic and/or covalent associations and/or may be indirectly linked, by for example, liposome formation. Thus, in one embodiment, multimers that may antibodies of the invention may bind, such as, for example, homodimers or homotrimers, are formed when C3a Receptor proteins contact one another in solution. In another embodiment, heteromultimers that antibodies of the invention may bind, such as, for example, heterotrimers or heterotetramers, are formed when proteins of the invention contact antibodies to C3a Receptor polypeptides (or antibodies to the heterologous polypeptide sequence in a fusion protein) in solution. In other embodiments, multimers that antibodies of the invention may bind are formed by covalent associations with and/or between the C3a Receptor proteins of the invention. Such covalent associations may involve one or more amino acid residues contained in the polypeptide sequence of the protein (e.g., the polypeptide sequence recited in SEQ ID NO:2 or the polypeptide encoded by the deposited cDNA clone of ATCC Deposit 75982). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a C3a Receptor fusion protein. In one example, covalent associations are between the heterologous sequence contained in a fusion protein (see, e.g., U.S. Pat. No. 5,478,925). In a specific example, the covalent associations are between the heterologous sequence contained in a C3a Receptor-Fc fusion protein (as described herein). In another specific example, covalent associations of fusion proteins are between heterologous polypeptide sequences from another C3a Receptor-related polypeptides (e.g., C5a receptor) that are capable of forming covalently associated multimers, such as for example, oseteoprotegerin (see, e.g., International Publication No. WO 98/49305, the contents of which are herein incorporated by reference in its entirety).

Antibodies of the invention may bind multimers that were generated using chemical techniques known in the art. For example, proteins desired to be contained in multimers may be chemically cross-linked using linker molecules and linker molecule length optimization techniques known in the art (see, e.g., U.S. Pat. No. 5,478,925, which is herein incorporated by reference in its entirety). Additionally, multimers that antibodies of the invention may bind can be generated using techniques known in the art to form one or more intermolecule cross-links between the cysteine residues located within the polypeptide sequence of the proteins desired to be contained in the multimer (see, e.g., U.S. Pat. No. 5,478,925, which is herein incorporated by reference in its entirety). Further, proteins that antibodies of the invention may bind can be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that antibodies of the invention may bind (see, e.g., U.S. Pat. No. 5,478,925, which is herein incorporated by reference in its entirety).

Alternatively, antibodies of the invention may bind multimers that were generated using genetic engineering techniques known in the art. In one embodiment, proteins contained in multimers that antibodies of the invention may bind are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that antibodies of the invention may bind are generated by ligating a polynucleotide sequence encoding a C3a Receptor polypeptide to a sequence encoding a linker polypeptide and then further to a synthetic polynucleotide encoding the translated product of the polypeptide in the reverse orientation from the original C-terminus to the N-terminus (see, e.g., U.S. Pat. No. 5,478,925, which is herein incorporated by reference in its entirety). In another embodiment, recombinant techniques described herein or otherwise known in the art are applied to generate recombinant C3a Receptor polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more C3a Receptor polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple C3a Receptor polypeptides separated by peptide linkers may be produced using conventional recombinant DNA technology. In specific embodiments, antibodies of the invention bind proteins comprising multiple C3a Receptor polypeptides separated by peptide linkers.

Another method for preparing multimer C3a Receptor polypeptides involves use of C3a Receptor polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric C3a Receptor proteins are those described in PCT application WO 94/10308, hereby incorporated by reference. Recombinant fusion proteins comprising a soluble C3a Receptor polypeptide fused to a peptide that dimerizes or trimerizes in solution are expressed in suitable host cells, and the resulting soluble multimeric C3a Receptor is recovered from the culture supernatant using techniques known in the art. In specific embodiments, antibodies of the invention bind C3a Receptor-leucine zipper fusion protein monomers and/or C3a Receptor-leucine zipper fusion protein multimers.

Antibodies of the Invention may Bind Modified C3a Receptor Polypeptides

It is specifically contemplated that antibodies of the present invention may bind modified forms of the C3a Receptor protein (SEQ ID NO:2)

In specific embodiments, antibodies of the present invention may bind C3a Receptor polypeptides (such as those described above) including, but not limited to naturally purified C3a Receptor polypeptides, C3a Receptor polypeptides produced by chemical synthetic procedures, and C3a Receptor polypeptides produced by recombinant techniques from a prokaryotic or eukaryotic host, including, for example, bacterial, yeast, higher plant, insect and manmmalian cells using, for example, the recombinant compositions and methods described above. Depending upon the host employed in a recombinant production procedure, the polypeptides may be glycosylated or non-glycosylated. In addition, C3a Receptor polypeptides may also include an initial modified methionine residue, in some cases as a result of host-mediated processes.

In addition, antibodies of the present invention may bind C3a Receptor proteins that have been chemically synthesized using techniques known in the art (e.g., see Creighton, Proteins: Structures and Molecular Principles, W.H. Freeman & Co., N.Y. (1983), and Hunkapiller, et al., *Nature* 310:105-111 (1984)). For example, a peptide corresponding to a fragment of a C3a Receptor be synthesized by use of a peptide synthesizer. Furthermore, if desired, nonclassical amino acids or chemical amino acid analogs can be introduced as a substitution or addition into the C3a Receptor polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses antibodies that bind C3a Receptor polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH$_4$, acetylation, formylation, oxidation, reduction, metabolic synthesis in the presence of tunicamycin; etc.

Additional post-translational modifications to C3a Receptor polypeptides for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of C3a Receptor polypeptide which may provide additional advantages such as increased solubility, stability and circulating time of the polypeptide, or decreased immunogenicity (see U.S. Pat. No. 4,179,337). The chemical moieties for denivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000,60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al, *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Inter J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each C3a Receptor polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

As mentioned the antibodies of the present invention may bind C3a Receptor polypeptides that are modified by either natural processes, such as posttranslational processing, or by chemical modification techniques which are well known in the art. It will be appreciated that the same type of modification may be present in the same or varying degrees at several sites in a given C3a Receptor polypeptide. C3a Receptor polypeptides may be branched, for example, as a result of ubiquitination, and they may be cyclic, with or without branching. Cyclic, branched, and branched cyclic C3a Receptor polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

Anti-C3a Receptor Antibodies:

In one embodiment, the invention provides antibodies (e.g., antibodies comprising two heavy chains and two light chains linked together by disulfide bridges) that specifically bind a C3a Receptor polypeptide (e.g., SEQ ID NO:2) or fragments or variants thereof, wherein the amino acid sequence of the heavy chain and the amino acid sequence of the light chain are the same as the amino acid sequence of a heavy chain and a light chain expressed by one or more cell lines referred to in Table 1. In another embodiment, the invention provides antibodies (each consisting of, two heavy chains and two light chains linked together by disulfide bridges to form an antibody) that specifically bind a C3a Receptor polypeptide (e.g., SEQ ID NO:2) or fragments or variants thereof, wherein the amino acid sequence of the heavy chain or the amino acid sequence of the light chain are the same as the amino acid sequence of a heavy chain or a light chain expressed by one or more cell lines referred to in Table 1. Specific binding to C3a Receptor polypeptides may be determined by immunoassays known in the art or described herein for assaying specific antibody-antigen binding. Molecules comprising, or alternatively consisting of, fragments or variants of these antibodies that specifically bind to C3a Receptor are also encompassed by the invention, as are nucleic acid molecules encoding these antibodies molecules, fragments and/or variants.

In one embodiment of the present invention, antibodies that specifically bind to C3a Receptor or a fragment or variant thereof, comprise a polypeptide having the amino acid sequence of any one of the heavy chains expressed by at least one of the cell lines referred to in Table 1 and/or any one of the light chains expressed by at least one of the cell lines referred to in Table 1.

In another embodiment of the present invention, antibodies that specifically bind to C3a Receptor or a fragment or variant thereof, comprise a polypeptide having the amino acid sequence of any one of the VH domains referred to in Table 1 and/or any one of the VL domains referred to in Table 1. In preferred embodiments, antibodies of the present invention comprise the amino acid sequence of a VH domain and VL domain from the same scFv selected from the group consisting of scFvs referred to in Table 1. In alternative embodiments, antibodies of the present invention comprise the amino acid sequence of a VH domain and a VL domain from different scFvs referred to in Table 1. Molecules comprising, or alternatively consisting of, antibody fragments or variants of the VH and/or VL domains referred to in Table 1 that specifically bind to C3a Receptor are also encompassed by the invention, as are nucleic acid molecules encoding these VH and VL domains, molecules, fragments and/or variants.

The present invention also provides antibodies that specifically bind to a C3a Receptor polypeptide, or polypeptide fragment or variant of C3a Receptor, wherein said antibodies comprise, or alternatively consist of, a polypeptide having an amino acid sequence of any one, two, three, or more of the VH CDRs referred to in Table 1. In particular, the invention provides antibodies that specifically bind C3a Receptor, comprising, or alternatively consisting of, a polypeptide having the amino acid sequence of a VH CDR1 referred to in Table 1. In another embodiment, antibodies that specifically bind C3a Receptor, comprise, or alternatively consist of, a polypeptide having the amino acid sequence of a VH CDR2 referred to in Table 1. In a preferred embodiment, antibodies that specifically bind C3a Receptor, comprise, or alternatively consist of a polypeptide having the amino acid sequence of a VH CDR3 referred to in Table 1. Molecules comprising, or alternatively consisting of, these antibodies, or antibody fragments or variants thereof, that specifically bind to C3a Receptor or a C3a Receptor fragment or variant thereof are also encompassed by the invention, as are nucleic acid molecules encoding these antibodies, molecules, fragments and/or variants.

The present invention also provides antibodies that specifically bind to a polypeptide, or polypeptide fragment or variant of C3a Receptor, wherein said antibodies comprise, or alternatively consist of, a polypeptide having an amino acid sequence of any one, two, three, or more of the VL CDRs referred to in Table 1. In particular, the invention provides antibodies that specifically bind C3a Receptor, comprising, or alternatively consisting of, a polypeptide having the amino acid sequence of a VL CDR1 referred to in Table 1. In an embodiment, antibodies that specifically bind C3a Receptor, comprise, or alternatively consist of, a polypeptide having the amino acid sequence of a VL CDR2 referred to in Table 1. In a preferred embodiment, antibodies that specifically bind C3a Receptor, comprise, or alternatively consist of a polypeptide having the amino acid sequence of a VL CDR3 referred to in Table 1. Molecules comprising, or alternatively consisting of, these antibodies, or antibody fragments or variants thereof, that specifically bind to C3a Receptor or a C3a Receptor fragment or variant are also encompassed by the invention, as are nucleic acid molecules encoding these antibodies, molecules, fragments and/or variants.

The present invention also provides antibodies (including molecules comprising, or alternatively consisting of, antibody fragments or variants) that specifically bind to a C3a Receptor polypeptide or polypeptide fragment or variant of C3a Receptor, wherein said antibodies comprise, or alternatively consist of, one, two, three, or more VH CDRs and one, two, three or more VL CDRs, as contained in a VH domain or VL domain referred to in Table 1. In particular, the invention provides for antibodies that specifically bind to a polypeptide or polypeptide fragment or variant of C3a Receptor, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VL CDR1, a VH CDR3 and a VL CDR2, a VH CDR3 and a VL CDR3, or any combination thereof, of the VH CDRs and VL CDRs referred to in Table 1. In a preferred embodiment, one or more of these combinations are from the same antibody as disclosed in Table 1. Molecules comprising, or alternatively consisting of, fragments or variants of these antibodies, that specifically bind to C3a Receptor are also encompassed by the invention, as are nucleic acid molecules encoding these antibodies, molecules, fragments or variants.

Nucleic Acid Molecules Encoding Anti-C3a Receptor Antibodies

The present invention also provides for nucleic acid molecules, generally isolated, encoding an antibody of the invention (including molecules comprising, or alternatively consisting of, antibody fragments or variants thereof).

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains referred to in Table 1 and a VL domain having an amino acid sequence of VL domain referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains referred to in Table I or a VL domain having an amino acid sequence of a VL domain referred to in Table 1.

The present invention also provides antibodies that comprise, or alternatively consist of, variants (including derivatives) of the antibody molecules (e.g., the VH domains and/or VL domains) described herein, which antibodies specifically bind to C3a Receptor or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to induce resistance to cellular insulin and/or glucose uptake).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g, improvements in antigen binding activity or change in antibody specificity). Following mutagenesis, the encoded protein may routinely be expressed and the functional and/or biological activity of the encoded protein, (e.g., ability to specifically bind C3a Receptor) can be determined using techniques described herein or by routinely modifying techniques known in the art.

In a specific embodiment, an antibody of the invention (including a molecule comprising, or alternatively consisting of, an antibody fragment or variant thereof), that specifically binds C3a Receptor polypeptides or fragments or variants thereof, comprises, or alternatively consists of, an amino acid sequence encoded by a nucleotide sequence that hybridizes to a nucleotide sequence that is complementary to that encoding one of the VH or VL domains referred to in Table 1, under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. 1, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that specifically binds to a C3a Receptor polypeptide or fragments or variants of a C3a Receptor polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80% at least 85%, at least 90%, at least 95%, or at least 99% identical, to the amino acid sequence of a VH domain referred to in Table 1.

In another embodiment, an antibody (including a molecule comprising, or alternatively consisting of, an antibody fragment or variant thereof), that specifically binds to a C3a Receptor polypeptide or fragments or variants of a C3a Receptor polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain referred to in Table 1.

Methods of Producing Antibodies

Antibodies in accordance with the invention are preferably prepared utilizing a phage scFv display library. Technologies utilized for achieving the same are disclosed in the patents, applications, and references disclosed herein.

In phage display methods, functional antibody domains are displayed on the surface of phage particles which carry the polynucleotide sequences encoding them. In particular, DNA sequences encoding VH and VL domains are amplified from animal cDNA libraries (e.g., human cDNA libraries of lymphoid tissues) or synthetic CDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a C3a Receptor polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280(1994); PCT application No. PCT/GB91/01 134; PCT publications WO 90/02809; WO 91/10737; WO 92/01047; WO 92/18719; WO 93/11236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 as single chain antibodies or Fab fragments in a phage display library. For example, the cDNAs encoding the VH and VL domains of the scFvs referred to in Table 1 may be expressed in all possible combinations using a phage display library, allowing for the selection of VH/VL combinations that bind C3a Receptor polypeptides with preferred binding characteristics such as improved affinity or improved off rates. Additionally, VH and VL domains—the CDR regions of the VH and VL domains of the scFvs referred to in Table 1, in particular, may be mutated in vitro. Expression of VH and VL domains with "mutant" CDRs in a phage display library allows for the selection of VH/VL combinations that bind C3a Receptor polypeptides with preferred binding characteristics such as improved affinity or improved off rates.

Additional Methods of Producing Antibodies

Antibodies of the invention (including antibody fragments or variants) can be produced by any method known in the art. For example, it will be appreciated that antibodies in accordance with the present invention can be expressed in cell lines including, but not limited to, myeloma cell lines and hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 1. In order to isolate the VH and VL domains from bacteria transfected with a vector containing the scFv, PCR primers complementary to VH or VL nucleotide sequences (See Example 2), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e. the VH domain, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, ie., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g. recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of antibodies of the invention (e.g., those referred to in Table 1), or fragments or variants thereof, are inserted within framework regions using recombinant DNA techniques known in the art. In a specific embodiment, one, two, three, four, five, six, or more of the CDRs of antibodies of the invention (e.g., those referred to in Table 1), or fragments or variants thereof, is inserted within framework regions using recombinant DNA techniques known in the art. The framework regions may be naturally occurring or consensus framework regions, and preferably human framework regions (see, e.g., Chothia et al., J. Mol. Biol. 278: 457-479 (1998) for a listing of human framework regions, the contents of which are hereby incorporated by reference in its entirety). Preferably, the polynucleotides generated by the combination of the framework regions and CDRs encode an antibody (including molecules comprising, or alternatively consisting of, antibody fragments or variants thereof) that specifically binds to C3a Receptor. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

XenoMouse Technology

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACS) containing germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146-156 (1997), Green and Jakobovits *J. Exp. Med.* 188:483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, Ser. No. 07/710,515, filed Nov. 8, 1990,Ser. No. 07/919,297, filed Jul. 24, 1992, Ser. No. 07/922,649, filed Jul. 30, 1992, filed Ser. No. 08/031,801 filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 0-8/464,584, filed Jun. 5, 1995, Ser. No. 08/464,582, filed Jun. 5, 1995, Ser. No. 08/471, 191, filed Jun. 5, 1995, Ser. No. 08/462,837, filed Jun. 5, 1995, Ser. No. 08/486,853, filed Jun. 5, 1995,Ser. No. 08/486, 857, filed Jun. 5, 1995, Ser. No. 08/486,859, filed Jun. 5, 1995, Ser. No. 08/462,513, filed Jun. 5, 1995, Ser. No. 08/724, 752, filed Oct. 2, 1996, and Ser. No. 08/759,620, filed Dec. 3, 1996. See also Mendez et al. *Nature Genetics* 15:146-156 (1997) and Green and Jakobovits *J. Exp. Med.* 188:483 495 (1998). See also European Patent No., EP 0 471 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against C3a Receptor polypeptides in order to vitiate concerns and/or effects of HAMA or HACA responses.

Monoclonal antibodies specific for C3a Receptor polypeptides were prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, XenoMouse™ mice were immunized with C3a Receptor polypeptides. After immunization, the splenocytes of such mice were extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the C3a Receptor polypetides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50435, WO 98/24893, WO 98/16654, WO 96/34096, WO 96/35735, and WO 91/10741; each of which is incorporated herein by reference in its entirety. In a specific embodiment, antibodies of the present invention comprise one or more VH and VL domains of the invention and constant regions from another immunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs of the scFvs referred to in Table 1, or fragments or variants thereof, and framework regions (and, optionally, one or more CDRs not present in the antibodies expressed by scFvs referred to in Table 1) from a human immunoglobulin molecule. In a preferred embodiment, an antibody of the present invention comprises a VH CDR3, VL CDR3, or both, corresponding to the same scFv, or different scFvs selected from the scFvs referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al, PNAS 91:969-973 (1994)), and chain shuffling (U.S. Pat. No. 5,565,352). In a preferred embodiment, chimeric antibodies comprise a human CDR3 having an amino acid sequence of any one of the VH CDR3s or VL CDR3s referred to in Table 1, or a variant thereof, and non-human framework regions or human framework regions different from those of the frameworks expressed by the corresponding scFvs disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W. A. *Gene Ther.* 4:11-15 (1997); Rondon and Marasco, *Annu. Rev. Microbiol.* 51:257-283 (1997); Proba et al., *J. Mol. Biol.* 275:245-253 (1998) Cohen et al., *Oncogene* 17:2445-2456 (1998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is(are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants thereof (single chain antibodies), microorganisms such as bacteria (eg., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., NSO, COS, CHO, BHK, 293, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antib molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entireties by reference herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa califormica* nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (eg., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such manmmalian host cells include, but are not limited to, CHO, VERY, BHK, Hela, COS, NSO, MDCK, 293, 3T3, and W138.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc.

Natl. Acad. Sci. USA 48:202 (1992)), and adenine phosphoribosyltransferase (Lowy et al., Cell 22:8 17 (1980)) genes can be employed in tk-, hgprt- or aprt-cells respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G -418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH II (5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and *DNA Cloning*, Hentschel, "The use of vectors based on gene amplification for the expression of cloned genes in mammalian cells" in Vol.3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310: 105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatizaton by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, 213Bi, or other radioisotopes such as, for example, iodine (131I, 125I, 123I, 121I), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr,32P, 153Gd, 169Yb, 51Cr, 54Mn, 75Se, 113Sn, and 117Tin.

In specific embodiments, antibodies of the invention may be labeled with Europium. For example, antibodies of the invention may be labelled with Europium using the DELFIA Eu-labeling kit (catalog#1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N",N'''-tetraacetic acid (DOTA). In specific embodiments, the macrocyclic chelator is α-(5-isothiocyanato-2-methoxyphenyl)-1,4,7,10-tetraaza-cyclododecane-1,4,7,10-tetraacetic acid. In other specific embodiments, the DOTA is attached to the antibody of the invention via a linker molecule. Examples of linker molecules useful for conjugatinga macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulthydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera. Drug Carrier Sys. 9:249-304 (1992); Francis et al., Intern J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (ClSO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyidiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera. Drug Carrier Sys. 9:249-304 (1992).

Characterization of Anti-C3a Receptor Antibodies

Antibodies of the present invention (including molecules comprising, or alternatively consisting of, antibody fragments or variants thereof) may also be described or specified in terms of their binding to C3a Receptor polypeptides or fragments or variants of C3a Receptor polypeptides. In specific embodiments, antibodies of the invention bind C3a Receptor polypeptides, or fragments or variants thereof, with a dissociation constant or KD of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind C3a Receptor polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind C3a Receptor polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. The invention encompasses antibodies that bind C3a Receptor polypeptides with a dissociation constant or KD that is within any one of the ranges that are between each of the individual recited values.

In specific embodiments, antibodies of the invention bind C3a Receptor polypeptides or fragments or variants thereof with an off rate ($k_{off}$) of less than or equal to $5\times10^{-2}$ sec$^{-1}$, $10^{-2}$ sec$^{-1}$, $5\times10^{-3}$ sec$^{-1}$. More preferably, antibodies of the invention bind C3a Receptor polypeptides or fragments or variants thereof with an off rate ($k_{off}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $5\times10^{-7}$ sec$^{-1}$ or $10^{-7}$ sec$^{-1}$. The invention encompasses antibodies that bind C3a Receptor polypeptides with an off rate ($k_{off}$) that is within any one of the ranges that are between each of the individual recited values.

In other embodiments, antibodies of the invention bind C3a Receptor polypeptides or fragments or variants thereof with an on rate ($k_{on}$) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, antibodies of the invention bind C3a Receptor polypeptides or fragments or variants thereof with an on rate ($k_{on}$) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$. The invention encompasses antibodies that bind C3a Receptor polypeptides with on rate ($k_{on}$) that is within any one of the ranges that are between each of the individual recited values.

The antibodies of the invention (including molecules comprising, or alternatively consisting of, antibody fragments or variants thereof) specifically bind to a polypeptide or polypeptide fragment or variant of a human C3a Receptor polypeptide (SEQ ID NO:2). In another embodiment, the antibodies of the invention specifically bind to a polypeptide or polypeptide fragment or variant of a simian C3a Receptor polypeptide. In yet another embodiment, the antibodies of the invention specifically bind to a polypeptide or polypeptide fragment or variant of a murine C3a Receptor polypeptide (SEQ ID NO:4). In one embodiment, the antibodies of the invention bind specifically to human and simian C3a Receptor polypeptides. In another embodiment, the antibodies of the invention bind specifically to human C3a Receptor polypeptides and murine C3a Receptor polypeptides. More preferably, antibodies of the invention, preferentially bind to human C3a Receptor polypeptides compared to murine C3a Receptor polypeptides.

In preferred embodiments, the antibodies of the present invention (including molecules comprising, or alternatively consisting of, antibody fragments or variants thereof), specifically bind to C3a Receptor polypeptides and do not cross-react with any other antigens. In preferred embodiments, the antibodies of the invention specifically bind to C3a Receptor polypeptides (e.g., SEQ ID NO:2 or fragments or variants thereof) and do not cross-react with one or more C3a Receptor-related (e.g., C5a receptor) polypeptides.

In other embodiments, the antibodies of the invention bind to C3a Receptor polypeptides (e.g., SEQ ID NO:2 or fragments or variants thereof) and cross-react with one or more C3a Receptor-related (e.g., C5a receptor) polypeptides.

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to inhibit or abolish of the binding of a C3a Receptor ligand (e.g., C3a anaphylatoxin) to C3a Receptor, the ability antagonize C3a Receptor action, the ability to antagonize C3a-mediated intracellular calcium release, the ability to inhibit C3a Receptor-mediated inflammatory response, the ability to inhibit the C3a Receptor-mediated activation, chemotaxis and/or degranulation of mast cells and/or granulocytes, and or the ability to inhibit C3a Receptor mediated constriction of airway smooth muscle. Optionally, the antibodies of the invention will bind to the same epitope as at least one of the antibodies specifically referred to herein. Such epitope binding can be routinely determined using assays known in the art.

The present invention provides for antibodies (including molecules comprising, or alternatively consisting of, antibody fragments or variants thereof), that inhibit one or more C3a Receptor polypeptide mediated biological activities. In one embodiment, an antibody that inhibits one or more C3a Receptor polypeptide mediated biological activity comprises, or alternatively consists of a VH and/or a VL domain of an sn scFv referred to in Table 1, or fragments or variants thereof. In a specific embodiment, an antibody that inhibits one or more C3a Receptor polypeptide mediated biological activities comprises, or alternatively consists of a VH and a VL domain corresponding to a single scFv referred to in Table 1, or fragments or variants thereof. Nucleic acid molecules encoding these antibodies are also encompassed by the invention.

The present invention provides for antibodies (including molecules comprising, or alternatively consisting of, antibody fragments or variants thereof), that inhibit C3a Receptor ligand (e.g., C3a anaphylatoxin) binding to C3a Receptor. In one embodiment, an antibody that inhibits C3a Receptor ligand (e.g., C3a anaphylatoxin) binding to C3a Receptor comprises, or alternatively consists of a VH and/or a VL domain referred to in Table 1, or fragments or variants thereof. In a specific embodiment, an antibody that inhibits C3a Receptor ligand (e.g., C3a anaphylatoxin) binding to C3a Receptor comprises, or alternatively consists of a VH and a VL domain corresponding to a single scFv referred to in Table 1, or fragments or variants thereof. Nucleic acid molecules encoding these antibodies are also encompassed by the invention.

The present invention provides for antibodies (including molecules comprising, or alternatively consisting of, antibody fragments or variants thereof), that inhibit C3a Receptor-mediated intracellular calcium release. In one embodiment, an antibody that inhibits C3a Receptor-mediated intracellular calcium release comprises, or alternatively consists of a VH and/or a VL domain referred to in Table 1, or fragments or variants thereof. In a specific embodiment, an antibody that inhibits C3a Receptor mediated-intracellular calcium release comprises, or alternatively consists of a VH and a VL domain corresponding to a single scFv referred to in Table 1, or fragments or variants thereof. Nucleic acid molecules encoding these antibodies are also encompassed by the invention.

The present invention also provides for antibodies (including molecules comprising, or alternatively consisting of, antibody fragments or variants thereof), that inhibit C3a Receptor-mediated inflammatory response. In one embodiment, an antibody that inhibits C3a Receptor-mediated inflammatory response comprises, or alternatively consists of a VH and/or a VL referred to in Table 1, or fragments or variants thereof In a specific embodiment, an antibody that inhibits C3a Receptor-mediated inflammatory response comprises, or alternatively consists of a VH and a VL domain corresponding to a single scFv referred to in Table 1, or fragments or variants thereof. Nucleic acid molecules encoding these antibodies are also encompassed by the invention.

The present invention provides for antibodies (including molecules comprising, or alternatively consisting of, antibody fragments or variants thereof), that inhibit C3a Receptor-mediated activation, chemotaxis and/or degranulation of mast cells and/or granulocytes. In one embodiment, an antibody that inhibits C3a Receptor-mediated activation, chemotaxis and/or degranulation of mast cells and/or granulocytes comprises, or alternatively consists of a VH and/or a VL domain referred to in Table 1, or fragments or variants thereof. In a specific embodiment, an antibody that inhibits C3a Receptor-mediated activation, chemotaxis and/or degranulation of mast cells and/or granulocytes comprises, or alternatively consists of a VH and a VL domain corresponding to a single scFv referred to in Table 1, or fragments or variants thereof. Nucleic acid molecules encoding these antibodies are also encompassed by the invention.

The present invention also provides for antibodies (including molecules comprising, or alternatively consisting of, antibody fragments or variants thereof), that inhibit C3a Receptor-mediated constriction of airway smooth muscle. In one embodiment, an antibody that inhibits C3a Receptor-mediated constriction of airway smooth muscle comprises, or alternatively consists of a VH and/or a VL of an scFv referred to in Table 1, or fragments or variants thereof. In a specific embodiment, an antibody that inhibits C3a Receptor-mediated constriction of airway smooth muscle comprises, or alternatively consists of a VH and a VL domain corresponding to a single scFv referred to in Table 1, or fragments or variants thereof. Nucleic acid molecules encoding these antibodies are also encompassed by the invention.

The present invention also provides for antibodies (including molecules comprising, or alternatively consisting of, antibody fragments or variants thereof), that decrease cell surface C3a Receptor expression. In one embodiment, an antibody that decreases cell surface C3a Receptor expression comprises, or alternatively consists of, a VH and/or a VL domain referred to in Table 1, or fragments or variants thereof. In a specific embodiment, an antibody that decreases cell surface C3a Receptor expression comprises, or alternatively consists of, a VH and a VL domain corresponding to a single scFv referred to in Table 1, or fragments or variants thereof. Nucleic acid molecules encoding these antibodies are also encompassed by the invention.

In certain embodiments, antibodies of the present invention may agonize the C3a receptor biological activities described above.

Antibodies of the present invention (including antibody fragments or variants thereof) may be characterized in a variety of ways. In particular, antibodies and related molecules of the invention may be assayed for the ability to specifically bind to C3a Recepto polypeptides or fragments or variants thereof using techniques described herein or routinely modifying techniques known in the art. Assays for the ability of the antibodies of the invention to specifically bind C3a Receptor polypeptides or fragments or variants thereof may be performed in solution (e.g., Houghten, Bio/Techniques 13:412421(1992)), on beads (e.g., Lam, Nature 354:82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698, 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Such assays may be used to identify antibodies that specifically bind to C3a Receptor polypeptides or a fragment or variant of a C3a Receptor polypeptide.

The antibodies of the invention may be assayed for specific binding to C3a Receptor polypeptides and cross-reactivity with other antigens by any method known in the art. Inmuunoassays which can be used to analyze specific binding and cross-reactivity include, but are not limited to, competitive and noncompetitive assay systems using techniques such as BIAcore analysis, FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen, in the form of a C3a Receptor-Fc fusion protein, may be bound to the anti-Ig Fc coated to the plate. This may be desirable so as to maintain the antigen protein (e.g., the C3a Receptor polypeptides) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I), or fragment or variant thereof with the antibody of interest in the presence of increasing amounts of unlabeled antigen, and the detection of the antibody bound to the labeled antigen. The affinity of the antibody of the present invention for C3a Receptor and the binding off-rates can be determined from the data by Scatchard plot analysis. Competition with a second antibody can also be determined using radioimmunoassays. In this case, C3a Receptor polypeptide is incubated with an antibody of the present invention conjugated to a labeled compound (e.g., compound labeled with $^3$H or $^{125}$I) in the presence of increasing amounts of an unlabeled second anti-C3a Receptor antibody. This kind of competitive assay between two antibodies, may also be used to determine if two antibodies bind the same, closely associated (e.g., overlapping) or different epitopes.

In other preferred embodiments, the invention provides antibodies that competitively inhibit binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a C3a Receptor polypeptide. In preferred embodiments, the invention provides antibodies that competitively inhibit the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a C3a Receptor polypeptide by between at least 10%, at least 20%, at least 30%, at least 40% at least 50%, at least 60%, at least 70%, at least 80%, or at least 95% in a competitive inhibition assay.

In preferred embodiments, the invention provides antibodies that competitively inhibit the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a C3a Receptor polypeptide more than an antibody comprising a VH and a VL domain from a single scFv referred to in Table 1 competitively inhibits itself.

In a preferred embodiment, BIAcore kinetic analysis may be used to determine the binding on and off rates of antibodies (including antibody fragments or variants thereof) to C3a Receptor, or fragments of C3a Receptor. BIAcore kinetic analysis comprise analyzing the binding and dissociation of antibodies from chips with immobilized C3a Receptor on their surface.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g. EDTA, PMSF, aprotinin, sodium vanadate), adding the antibody of interest to the cell lysate, incubating for a period of time (e.g., 1 to 4 hours) at 40 degrees C, adding protein A and/or protein G sepharose beads to the cell lysate, incubating for about an hour or more at 40 degrees C, washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)$_2$ fragment, or a portion thereof. Methods for fusing or conjugating polypeptides to antibody portions are known in the art. See, e.g., U.S. Pat. Nos. 5,356,603; 5,622,929; 5,359,046; 5,349, 053; 5,447,851; 5,112,946; EP 307,434; EP 367,166; PCT publications WO 96/04388; WO 91/06570; Ashkenazi et al., Proc. Natl. Acad. Sci. USA 88: 10535-10539 (1991); Zheng et al., J. Immunol. 154:5590-5600 (1995); and VII et al., Proc. Natl. Acad. Sci. USA 89:11357-11341 (1992) (said reference incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287: 265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions specifically bind to C3a Receptor may be recombined with one or more components, motifs, sections, parts, domains, fragments, etc. of one or more heterologous molecules.

Moreover, the antibodies of the present invention (including antibody fragments or variants thereof) can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexahistidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used diagnostically to, for example, monitor or prognose the development or progression of a tumor as part of a clinical testing procedure to, e.g. determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin; and examples of suitable radioactive material include, but are not limited to, iodine ($^{121}$I, $^{123}$I, $^{131}$I), carbon ($^{13}$C), sulfur ($^{35}$S), tritium ($^{3}$H), indium ($^{111}$In, $^{112}$In, $^{113m}$In, $^{115m}$In), techetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody of the invention (including antibody fragments or variants thereof), may be coupled or conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Z, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and frragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (eg., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM 1 (see, International Publication No. WO 97/35899), Fas Ligand (Takahashi et al., *Int. Immunol.*, 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the C3a Receptor polypeptides, in both in vitro and in vivo diagnostic and therapeutic methods. For example, the antibodies have use in immunoassays for qualitatively and quantitatively measuring levels of C3a Receptor polypeptides in biological samples. See, e.g., Harlow et al., Antibodies: A Laboratory Manual, (Cold Spring Harbor Laboratory Press, 2nd ed. 1988) (incorporated by reference herein in its entirety).

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types, particularly of adipose cells. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

These techniques allow for the screening of particular populations of cells, such as adipocytes (e.g., in Type I or II diabetes patients). Alternatively, these techniques allow for the screening of mast cells, eosinophils, lymphocytes and bronchial tissue for the expression of C3a Receptor.

Epitope Manpine

The present invention provides antibodies (including antibody fragments or variants thereof), which can be used to identify epitopes of a C3a Receptor polypeptide. In particular, the antibodies of the present invention can be used to identify epitopes of a human C3a Receptor polypeptide (e.g., SEQ ID NO:2) or a C3a Receptor polypeptide expressed on human cells; a murine C3a Receptor or a C3a Receptor polypeptide expressed on murine cells; a rat C3a Receptor polypeptide or a C3a Receptor polypeptide expressed on rat cells; or a monkey C3a Receptor polypeptide or a C3a Receptor polypeptide expressed on monkey cells, using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occurring forms of C3a Receptor polypeptides.

Diagnostic Uses of Antibodies

Labeled antibodies of the invention (including molecules comprising, or alternatively consisting of, antibody fragments or variants thereof) which specifically bind to a C3a Receptor polypeptide can be used for diagnostic purposes to detect, diagnose, prognose, or monitor diseases and/or disorders. In specific embodiments, labeled antibodies of the invention (including molecules comprising, or alternatively consisting of, antibody fragments or variants thereof) which specifically bind to a C3a Receptor polypeptide can be used for diagnostic purposes to detect, diagnose, prognose, or monitor diseases and/or disorders associated with the aberrant expression and/or activity of a C3a Receptor polypeptide.

The invention provides for the detection of expression of a C3a Receptor polypeptide comprising: (a) assaying the expression of a C3a Receptor polypeptide in a biological sample from an individual using one or more antibodies of the invention that specifically binds to a C3a Receptor polypeptide; and (b) comparing the level of a C3a Receptor polypeptide with a standard level of a C3a Receptor polypeptide, (e.g., the level in normal biological samples).

The invention provides for the detection of aberrant expression of a C3a Receptor polypeptide comprising: (a) assaying the expression of a C3a Receptor polypeptide in a biological sample from an individual using one or more antibodies of the invention that specifically binds to a C3a Receptor polypeptide; and (b) comparing the level of a C3a Receptor polypeptide with a standard level of a C3a Receptor polypeptide, e.g., in normal biological samples, whereby an increase or decrease in the assayed level of a C3a Receptor polypeptide compared to the standard level of a C3a Receptor polypeptide is indicative of aberrant expression.

By "biological sample" is intended any fluids and/or cells obtained from an individual, body fluid, body tissue, body cell, cell line, tissue culture, or other source which may contain a C3a Receptor polypeptide protein or mRNA. Body fluids include, but are not limited to, sera, plasma, urine, saliva, mucous, pleural fluid, synovial fluid, and spinal fluid. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

One aspect of the invention is the detection and diagnosis of a disease or disorder associated with aberrant expression of a C3a Receptor polypeptide or a C3a Receptor polypeptide in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising; or alternatively consisting of, antibody fragments or variants thereof) that specifically binds to a C3a Receptor polypeptide; b) waiting for a time interval following the administering for permitting the labeled antibody to preferentially concentrate at sites in the subject where C3a Receptor polypeptide is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of a C3a Receptor polypeptide or a C3a Receptor polypeptide. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 milliCuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

In specific embodiments, antibodies of the present invention may be used in the diagnosis, prevention, and treatment of asthma, allergy, inflammation and inflammatory diseases and disorders, particularly those diseases and/or disorders described in the "Therapeutic Uses of Antibodies" sections below.

Therapeutic Uses of Antibodies of the Invention

One or more antibodies of the present invention (including molecules comprising, or alternatively consisting of, antibody fragments or variants thereof) that specifically bind to C3a Receptor may be used locally or systemically in the body as a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for preventing or treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. In one embodiment, the antibodies of the invention can be used to treat, ameliorate or prevent diseases, disorders or conditions, including, but not limited to, any one or more of the diseases, disorders, or conditions described herein. The treatment and/or prevention of diseases, disorders, or conditions includes, but is not limited to, alleviating symptoms associated with those diseases, disorders or conditions. Antibodies of the invention may be provided in pharmaceutically acceptable compositions as known in the art or as described herein.

Treatment and Prevention of Inflammation and Inflammatory Disorders

Members of the C3a Receptor family of proteins are believed to be involved in biological activities associated with the inflammatory response. Accordingly, antibodies of the invention (including fragments, variants, and fusion proteins thereof, especially neutralizing or antagonistic antibodies) may be used in the diagnosis, prognosis, prevention, and/or treatment of diseases and/or disorders associated with inappropriate or excessive inflammation.

In a specific embodiment, the present invention encomapsses a method for inhibiting C3a Receptor-mediated inflammation, which involves administering to a cell, or animal an effective amount of an antibody of the invention, capable of decreasing C3a Receptor-mediated signaling.

Preferably, C3a Receptor-mediated signaling is decreased to treat a disease wherein increased C3a Receptor expression is exhibited.

In preferred embodiments, the antibodies of the invention (including fragments and variants thereof) may be used in the diagnosis, prognosis, prevention, and/or treatment of inflammatory disorders, as described herein. In specific preferred embodiments, antagonistic antibodies of the invention (including fragments and variants thereof) and compositions comprising such antagonistic antibodies, may be used in the diagnosis, prognosis, prevention, and/or treatment of inflammatory disorders, as described herein.

In preferred embodiments, antibodies or antibody compositions of the present invention are used to treat, prevent, and/or diagnose allergies and associated conditions. In specific preferred embodiments, antibodies of the present invention are used to treat, prevent, and/or diagnose asthma. For the treatment of allergies, asthma and associated conditions, the therapeutic antibodies of the invention are preferably antagonistic-anti C3a Receptor antibodies. Moreover, these molecules can be used to treat, prevent, and/or diagnose anaphylaxis, hypersensitivity to an antigenic molecule, or blood group incompatibility.

Additionally, antibodies or antibody compositions of the invention, may be used to treat or prevent IgE-mediated allergic reactions. Such allergic reactions include, but are not limited to, asthma, rhinitis, and eczema. Antibodies or antibody compositions of the present invention may be used to modulate IgE concentrations in vitro or in vivo.

Moreover, antibodies of the present invention have uses in the diagnosis, prognosis, prevention, and/or treatment of inflammatory conditions. For example, since antibodies or antibody compositions of the invention may inhibit the activation, proliferation and/or differentiation of cells involved in an inflammatory response, these molecules can be used to diagnose, prognose, prevent, and/or treat chronic and acute inflammatory conditions. Such inflammatory conditions include, but are not limited to, for example, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1), respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis; ischemic brain injury and/or stroke; traumatic brain injury; neurodegenerative disorders, such as, e.g., Parkinson's disease and Alzheimer's disease; AIDS-related dementia; and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., hepatitis, rheumatoid arthritis, gout, trauma, pancreatitis, sarcoidosis, dermatitis, renal ischemia-reperfusion injury, Grave's disease, systemic lupus erythematosis, diabetes mellitus, and allogenic transplant rejection).

Because inflammation is a fundamental defense mechanism, inflammatory disorders can effect virtually any tissue of the body. Accordingly, antibodies or antibody compositions of the invention have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retninitis, rhinitis, salpingitis, scleritis, sclerochoroiditis, scrotitis, sinusitis, sponylitis, steatitis, stomatitis, synovitis, syringitis, tendonitis, tonsillitis, urethritis, and vaginitis.

In specific embodiments, antibodies of the invention, are useful to treat, diagnose, and/or prevent organ transplant rejections and graft-versus-host disease. Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD. In specific embodiments, polypeptides, antibodies, or polynucleotides of the invention, and/or agonist or antagonists thereof, that inhibit an immune response, particularly the activation, proliferation, differentiation, or chemotaxis of T-cells, may be an effective therapy in preventing experimental allergic and hyperacute xenograft rejection.

Because inflammation is a fundamental bodily defense mechanism, antibodies of the invention (including fragments, variants, and fusion proteins thereof, especially neutralizing or antagonistic antibodies) are likely to have uses in a wide range of inflammatory disorders. Therefore, the above-mentioned biological activities are not intended to be limiting.

Antibodies of the invention (including fragments, variants, and fusion proteins thereof) may work to modulate chemotactic activity of C3A Receptor expressing cells. A chemotactic molecule attracts or mobilizes cells (e.g., mast cells, eosinophils, monocytes, fibrblasts, neutrophils, T-cells, epithelial and/or endothelial cells) to a particular site in the body, such as inflammation, infection, or site of hyperproliferation. The mobilized cells can then fight off and/or heal the particular trauma or abnormality.

Antibodies of the invention (including fragments, variants, and fusion proteins thereof) may modulate chemotactic activity of C3a Receptor expressing cells. For example antagonistic anti-C3A Receptor antibodies may decrease chemotaxis of C3a Receptor expressing cells, while agonistic anti-C3A Receptor antibodies may induce or enhance chemotaxis of C3a Receptor expressing cells. Such antibodies that modulate the chemotactic activity of C3a Receptor expressing cells may be used to treat inflammation, infection, hyperproliferative disorders, or other immune system disorders by influencing the number of cells targeted to or away from a particular location in the body. For example, agonistic anti-C3a Receptor antibodies can be used to treat wounds and other trauma to tissues by attracting immune cells to the injured location.

Additional Therapeutic Uses of Antibodies of the Invention

Treatment of Immune System Related Diseases and Disorders

Antibodies of the invention (including fragments, variants, and fusion proteins thereof) may be useful in treating, preventing, and/or diagnosing diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes Y cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

Antibodies of the invention (including fragments, variants, and fusion proteins thereof) may be useful in treating, preventing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g., agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, antibodies of the invention (including fragments, variants, and fusion proteins thereof) could also be used to modulate hemostatic activity (the stopping of bleeding) or thrombolytic activity (clot formation). For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

The antibodies of the invention (including fragments, variants, and fusion proteins thereof, especially neutralizing or antagonistic antibodies) may be useful in treating, preventing, and/or diagnosing autoimmune disorders. Many autoimmune disorders result from inappropriate recognition of self as foreign material by immune cells. This inappropriate recognition results in an immune response leading to the destruction of the host tissue. Therefore, the administration of antibodies of the invention (including fragments, variants, and fusion proteins thereof, especially neutralizing or antagonistic antibodies) that can inhibit an immune response, particularly the proliferation, differentiation, or chemotaxis of T-cells, may be an effective therapy in preventing autoimmune disorders.

Autoimmune diseases or disorders that may be treated, prevented, and/or diagnosed by antibodies of the invention (including fragments, variants, and fusion proteins thereof, especially neutralizing or antagonistic antibodies) include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Autism, Guillain-Barre Syndrome, insulin dependent diabetes mellitis, and autoimmune inflammatory eye disorders, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune thrombocytopenic purpura, rheumatoid arthritis, schieroderma with anticollagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

Additional autoimmune disorders (that are probable) that may be treated, prevented, and/or diagnosed with the antibodies or antibody compositions include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the antibodies or antibody compositions include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic denmatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using for example, antibodies of the invention (including fragments, variants, and fusion proteins thereof, especially neutralizing or antagonistic antibodies).

In a specific preferred embodiment, rheumatoid arthritis is treated, prevented, and/or diagnosed using antibodies of the invention (including fragments, variants, and fusion proteins thereof, especially neutralizing or antagonistic antibodies). In another specific preferred embodiment, systemic lupus erythemosus is treated, prevented, and/or diagnosed using antibodies of the invention (including fragments, variants, and fusion proteins thereof, especially neutralizing or antagonistic antibodies). In another specific preferred embodiment, idiopathic thrombocytopenia purpura is treated, prevented, and/or diagnosed using antibodies of the invention (including fragments, variants, and fusion proteins thereof, especially neutralizing or antagonistic antibodies). In another specific preferred embodiment IgA nephropathy is treated, prevented, and/or diagnosed using antibodies of the invention (including fragments, variants, and fusion proteins thereof, especially neutralizing or antagonistic antibodies). In a preferred embodiment, the autoimmune diseases and disorders and/or conditions associated with the diseases and disorders recited above are treated, prevented, and/or diagnosed using antibodies against the protein of the invention.

In specific embodiments, antibodies of the invention (including fragments, variants, and fusion proteins thereof), are useful to treat, diagnose, and/or prevent transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

Antibodies of the invention (including fragments, variants, and fusion proteins thereof) can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, antibodies of the invention (including fragments, variants, and fusion proteins thereof, especially neutralizing or antagonistic antibodies) may also directly inhibit the infectious agent, without necessarily eliciting an immune response.

Antibodies or antibody compositions of the present invention may be administered to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantifies of one or more antibodies (e.g., IgG, IgA, IgM, and IgE), to induce higher affinity antibody production (e.g., IgG, IgA, IgM, and IgE), and/or to increase an immune response.

Antibodies or antibody compositions of the present invention may be administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

Antibodies or antibody compositions of the present invention may be used as a vaccine adjuvant that enhances immune responsiveness to specific antigen.

Antibodies or antibody compositions of the present invention may be used as a n adjuvant to enhance tumor-specific immune responses.

Antibodies or antibody compositions of the present invention may be used as an adjuvant to enhance anti-viral immune responses. Anti-viral immune responses that may be enhanced using compositions of the invention as an adjuvant, include virus and virus associated diseases or symptoms described herein or otherwise known in the art. In specific embodiments, the antibodies or antibody compositions are used as an adjuvant to enhance an immune response to a virus, disease, or symptom selected from the group consisting of: AIDS, meningitis, Dengue, EBV, and hepatitis (e.g., hepatitis B). In another specific embodiment, the antibodies or antibody compositions are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

Antibodies or antibody compositions of the present invention may be used as an adjuvant to enhance anti-bacterial or anti-fungal immune responses. Anti-bacterial or anti-fungal immune responses that may be enhanced using compositions of the invention as an adjuvant, include bacteria or fungus and bacteria or fungus associated diseases or symptoms described herein or otherwise known in the art. In specific embodiments, the antibodies or antibody compositions are used as an adjuvant to enhance an immune response to a bacteria or fungus, disease, or symptom selected from the group consisting of tetanus, Diphtheria, botulism, and meningitis type B. In another specific embodiment, the antibodies or antibody compositions are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli, Borrelia burgdorferi*, and Plasmodium (malaria).

Antibodies or antibody compositions of the present invention may be used as an adjuvant to enhance anti-parasitic immune responses. Anti-parasitic immune responses that may be enhanced using compositions of the invention as an adjuvant, include parasite and parasite associated diseases or symptoms described herein or otherwise known in the art. In specific embodiments, the antibodies or antibody compositions are used as an adjuvant to enhance an immune response to a parasite. In another specific embodiment, the antibodies or antibody compositions are used as an adjuvant to enhance an immune response to Plasmodium (malaria).

Antibodies or antibody compositions of the present invention may be used as an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

Antibodies or antibody compositions of the present invention may be used as an agent to boost immunoresponsiveness among individuals having an acquired loss of B cell function. Conditions resulting in an acquired loss of B cell function that may be ameliorated or treated by administering the antibody or antibody compositions of the invention, include, but are not limited to, HIV Infection, AIDS, bone marrow transplant, and B cell chronic lymphocytic leukemia (CLL).

Antibodies or antibody compositions of the present invention may be used as an agent to boost immunoresponsiveness among individuals having a temporary immune deficiency. Conditions resulting in a temporary immune deficiency that may be ameliorated or treated by administering the antibody or antibody compositions of the invention, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

Antibodies or antibody compositions of the present invention may be used as a regulator of antigen presentation by monocytes, dendritic cells, and/or B-cells. In one embodiment, antibody or antibody compositions of the present invention enhance antigen presentation or antagonize antigen presentation in vitro or in vivo. Moreover, in related embodiments, said enhancement or antagonization of antigen presentation may be useful as an anti-inflammatory treatment or to modulate the immune system.

Antibodies of the invention (including fragments, variants, and fusion proteins thereof) may be used to modulate IgE concentrations in vitro or in vivo.

Antibodies or antibody compositions of the present invention may be used as an agent to direct an individuals immune system towards development of a humoral response (i.e. TH2) as opposed to a TH1 cellular response.

Antibodies or antibody compositions of the present invention may be used as an agent to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

Antibodies or antibody compositions of the present invention may be used as a stimulator of B cell production in pathologies such as AIDS, chronic lymphocyte disorder and/or Common Variable Immunodeficiency.

Antibodies or antibody compositions of the present invention may be used as a therapy for generation and/or regeneration of lymphoid tissues following surgery, trauma or genetic defect.

Antibodies or antibody compositions of the present invention may be used as a gene-based therapy for genetically inherited disorders resulting in immuno-incompetence such as observed among SCID patients.

Antibodies or antibody compositions of the present invention may be used as an agent capable of activating T cells.

Antibodies or antibody compositions of the present invention may be used as an agent capable of activating monocytes/macrophages to defend against parasitic diseases that effect monocytes such as Leshmania.

Antibodies or antibody compositions of the present invention may be used as pretreatment of bone marrow samples prior to transplant. Such treatment would increase B cell representation and thus accelerate recovery.

Antibodies or antibody compositions of the present invention may be used as an agent capable of regulating secreted cytokines that are elicited by polypeptides of the invention.

All of the above described applications as they may apply to veterinary medicine.

Antibodies or antibody compositions of the present invention may be used as a means of blocking various aspects of immune responses to foreign agents or self Examples include autoimmune disorders such as lupus, and arthritis, as well as immunoresponsiveness to skin allergies, inflammation, bowel disease, injury and pathogens. Antibodies or antibody compositions of the present invention may be used as therapy for preventing the B cell proliferation and Ig secretion associated with autoimmune diseases such as idiopathic thrombocytopenic purpura, systemic lupus erythramatosus and MS.

Antibodies or antibody compositions of the present invention may be used as an inhibitor of migration of C3A Receptor expressing cells such as eosinophils and mast cells. This activity disrupts tissue architecture or cognate responses and is useful, for example in disrupting immune responses, and blocking sepsis.

Antibodies or antibody compositions of the present invention may be used as an inhibitor of graft versus host disease or transplant rejection.

Antibodies or antibody compositions of the present invention may be used as a therapy for B cell and/or T cell malignancies such as ALL, Hodgkins disease, non-Hodgkins lymphoma, Chronic lymphocyte leukemia, plasmacytomas, multiple mycloma, Burkitt's lymphoma, and EBV-transformed diseases.

Antibodies or antibody compositions of the present invention may be used as a therapy for chronic hypergammaglobulinemeia evident in such diseases as monoclonalgammopathy of undetermined significance (MGUS), Waldenstrom's disease, related idiopathic monoclonalgammopathies, and plasmacytomas.

Antibodies or antibody compositions of the present invention may be used as a therapy for decreasing cellular proliferation of Large B-cell Lymphomas.

Antibodies or antibody compositions of the present invention may be used as a means of decreasing the involvement of B cells and Ig associated with Chronic Myelogenous Leukemia.

Antibodies or antibody compositions of the present invention may be used as an immunosuppressive agent(s).

Antibodies or antibody compositions of the present invention may be employed in a composition with a pharmaceutically acceptable carrier, e.g., as described herein.

Antibodies or antibody compositions of the present invention may be employed, for instance, to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of autoimmune diseases are described herein and include multiple sclerosis, and insulin-dependent diabetes. Antibodies or antibody compositions of the present invention may also be employed to treat infectious diseases including silicosis, sarcoidosis, idiopathic pulmonary fibrosis by, for example, preventing the recruitment and activation of mononuclear phagocytes. They may also be employed to treat idiopathic hypereosinophilic syndrome by, for example, preventing eosinophil production and migration. The antagonists or agonists or may also be employed for treating atherosclerosis, for example, by preventing monocyte infiltration in the artery wall.

Antibodies or antibody compositions of the present invention may be employed to treat ARDS.

Antibodies or antibody compositions of the present invention may be employed to stimulate wound and tissue repair, stimulate angiogenesis, stimulate the repair of vascular or lymphatic diseases or disorders. Additionally, antibody or antibody compositions of the invention may be used to stimulate the regeneration of mucosal surfaces.

In a specific embodiment, antibodies of the invention (including fragments, variants, and fusion proteins thereof) are used to treat or prevent a disorder characterized by primary or acquired immunodeficiency, deficient serum immunoglobulin production, recurrent infections, and/or immune system dysfunction. Moreover, antibody or antibody compositions of the invention may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii.

In another specific embodiment, antibody or antibody compositions of the invention may be used to treat, diagnose, prognose, and/or prevent selective IgA deficiency, myeloperoxidase deficiency, C2 deficiency, ataxia-telangiectasia, DiGeorge anomaly, common variable immunodeficiency (CVI), X-linked agammaglobulinemia, severe combined immunodeficiency (SCID), chronic granulomatous disease (CGD), and Wiskott-Aldrich syndrome.

Examples of autoimmune disorders that can be treated or detected are described above and also include, but are not limited to: Addison's Disease, hemolytic anemia, antiphospholipid syndrome, rheumatoid arthritis, dermatitis, allergic encephalomyelitis, glomerulonephrits, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

In specific embodiments, the antibody compositions of the invention are used as an agent to boost immunoresponsiveness among B cell immunodeficient individuals, such as, for example, an individual who has undergone a partial or complete splenectomy.

It is preferred to use high affinity and/or potent antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibody or antibody compositions of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4-integrins, (See, e.g., Curr Top Microbiol Immunol 1998;231:125-41, which is hereby incorporated by reference). Such therapeutic affects of the present invention may be achieved either alone, or in combination with small molecule drugs or adjuvants.

In another embodiment, the invention provides a method of delivering antibodies or antibody compositions of the invention (or fragments or variants thereof) to targeted cells expressing the polypeptide of the present invention. Antibodies of the invention may be associated with with heterologous polypeptides, heterologous nucleic acids, toxins, or prodrugs via hydrophobic, hydrophilic, ionic and/or covalent interactions.

Treatment of Cardiovascular Disorders

Antibodies of the invention (including fragments, variants, and fusion proteins thereof), may be used to treat, prevent, diagnose, and or prognose cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet fight ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson- White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteribis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Antibodies may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Antibodies may be administered as part of a Therapeutic, described in more detail below. Methods of delivering polynucleotides are described in more detail herein.

The antibodies of the invention can be used to treat, ameliorate or prevent diseases, disorders or conditions associated with aberrant expression and/or activity of C3a Receptor, including, but not limited to, any one or more of the diseases, disorders, or conditions described herein. The treatment and/or prevention of diseases, disorders, or conditions associated with aberrant C3a Receptor expression and/or activity includes, but is not limited to, alleviating symptoms associated with those diseases, disorders or conditions. Antibodies of the invention may be provided in pharmaceutically acceptable compositions as known in the art or as described herein.

Further, antibodies of the present invention (including molecules comprising, or alternatively consisting of, antibody fragments or variants thereof) which inhibit C3a Receptor-mediated biological activities (e.g., C3a Receptor-mediated calcium flux) can be administered to an animal to treat, prevent or ameliorate a disease or disorder described herein, particularly asthma and inflammatory disorders. These antibodies may diminish either all or a subset of the biological activities of C3a Receptor, for example, by inducing a conformational change in C3a Receptor. In a specific embodiment, an antibody of the present invention that inhibits C3a Receptor activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to C3a Receptor activity in absence of the antibody is administered to an animal to treat, prevent or ameliorate a disease or disorder. In another embodiment, a combination of antibodies, a combination of antibody fragments, a combination of antibody variants, or a combination of antibodies, antibody fragments and/or antibody variants that inhibit C3a Receptor activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to C3a Receptor activity in absence of the said antibodies or antibody fragments and/or antibody variants is administered to an animal to treat, prevent or ameliorate a disease or disorder.

Further, antibodies of the present invention (including molecules comprising, or alternatively consisting of, antibody fragments or variants thereof) which inhibit C3a Receptor-mediated biological activities (e.g., C3a Receptor-mediated calcium flux) can be administered to an animal to treat, prevent or ameliorate a disease or disorder associated with aberrant C3a Receptor or C3a Receptor Ligand (e.g., C3a anaphylatoxin) expression or function,. These antibodies may diminish either all or a subset of the biological activities of C3a Receptor, for example, by preventing C3a Receptor interaction with it ligand(s). In a specific embodiment, an antibody of the present invention that diminishes C3a Receptor activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to C3a Receptor activity in absence of the antibody is administered to an animal to treat, prevent or ameliorate a disease or disorder associated with aberrant C3a Receptor or C3a Receptor ligand or expression or function. In another embodiment, a combination of antibodies, a combination of antibody fragments, a combination of antibody variants, or a combination of antibodies, antibody fragments and/or antibody variants that diminish C3a Receptor activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to C3a Receptor activity in absence of the said antibodies or antibody fragments and/or antibody variants is administered to an animal to treat, prevent or ameliorate a disease or disorder associated with aberrant C3a Receptor or C3a Receptor ligand expression or function.

Antibodies of the present invention (including molecules comprising, or alternatively consisting of, antibody fragments or variants thereof) that function as agonists or antagonists of C3a Receptor, can be administered to an animal to treat, prevent or ameliorate a disease or disorder associated with aberrant C3a Receptor or C3a Receptor ligand expression or function. For example, antibodies of the invention which mimic the action of C3a Receptor ligand (e.g., C3a anaphylatoxin) binding to the C3a Receptor, in full or in part, (e.g., antibodies that act as C3a Receptor agonists), may be administered to an animal to treat, prevent or ameliorate a disease or disorder associated with aberrant C3a Receptor or C3a Receptor ligand expression or function. Antibodies or antibody compositions of the present invention may be used as an alternative example, antibodies of the invention which disrupt or prevent the interaction between C3a Receptor and its receptor or inhibit, reduce, or prevent signal transduction through one or more C3a Receptors, may be administered to an animal to treat, prevent or ameliorate a disease or disorder associated with aberrant C3a Receptor or C3a Receptor ligand expression or function. Antibodies of the invention which do not prevent C3a Receptor from binding its ligand but inhibit or downregulate C3a Receptor signal transduction can be administered to an animal to treat, prevent or ameliorate a disease or disorder associated with aberrant C3a Receptor or C3a Receptor ligand expression or function. The ability of an antibody of the invention to enhance, inhibit, upregulate or downregulate C3a Receptor signal transduction may be determined by techniques described herein or otherwise known in the art. For example, C3a Receptor-induced receptor activation and the activation of signaling molecules can be determined by detecting the association of adaptor proteins with the C3a Receptors, by immunoprecipitation followed by western blot analysis (for example, as described herein).

In a specific embodiment, an antibody of the present invention (including molecules comprising, or alternatively consisting of, antibody fragments or variants thereof) that inhibits or downregulates, in full or in part, C3a Receptor activity (e.g., inhibition of insulin action) by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to C3a Receptor activity in absence of the antibody is administered to an animal to treat, prevent or ameliorate a disease or disorder associated with aberrant C3a Receptor ligand (e.g., C3a anaphylatoxin) or C3a Receptor expression or function. In another embodiment, a combination of antibodies, a combination of antibody fragments, a combination of antibody variants, or a combination of antibodies, antibody fragments, and/or variants that inhibit or downregulate C3a Receptor activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to C3a Receptor activity in absence of said antibodies, antibody fragments, and/or antibody variants are administered to an animal to treat, prevent or ameliorate a disease or disorder associated with aberrant C3a Receptor ligand (e.g., C3a anaphylatoxin) or C3a Receptor expression or function.

Further, antibodies of the present invention (including molecules comprising, or alternatively consisting of, antibody fragments or variants thereof) which activate C3a Receptor-mediated biological activities (e.g., C3a Receptor-mediated calcium release) can be administered to an animal to treat, prevent or ameliorate a disease or disorder associated with aberrant C3a Receptor ligand (e.g., C3a) or C3a Receptor expression or function. These antibodies may potentiate or activate either all or a subset of the biological activities of C3a Receptor, for example, by inducing a conformational change in C3a Receptor. In a specific embodiment, an antibody of the present invention that increases C3a Receptor activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to C3a Receptor activity in absence of the antibody is administered to an animal to treat, prevent or ameliorate a disease or disorder associated with aberrant C3a Receptor ligand (e.g., C3a anaphylatoxin) or C3a Receptor expression or function. In another embodiment, a combination of antibodies, a combination of antibody fragments, a combination of antibody variants, or a combination of antibodies, antibody fragments and/or antibody variants that increase C3a Receptor activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to C3a Receptor activity in absence of the said antibodies or antibody fragments and/or antibody variants is administered to an animal to treat, prevent or ameliorate a disease or disorder associated with aberrant C3a Receptor ligand (e.g., C3a anaphylatoxin) or C3a Receptor expression or function.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (ie., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below. The antibodies and/or antibody compositions of the invention and/or agonists or antagonists thereof is administered to the patient by any suitable technique, including but not limited to, parenteral, sublingual, topical, intrapulmonary and intranasal, and those techniques further discussed herein.

Various delivery systems are known and can be used to administer an antibody of the invention or a fragment or variant thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermnal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et a., in Liposomes in the Therapy of Infectious Disease and Cancer, Lopez-Berestein and Fidler (eds.), Liss, New York, pp. 353-365 (1989); Lopez-Berestein, ibid., pp. 3 17-327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:71 (1983); see also Levy et al., Science 228: 190 (1985); During et al., Ann. Neurol. 25:35 1 (1989); Howard et al., J.Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent antibodies of the invention (including molecules comprising, or alternatively consisting of, antibody fragments or variants thereof) that specifically bind to one or more C3a Receptor polypeptides, or polynucleotides encoding antibodies that specifically bind to one or more C3a Receptor polypeptides, for both immunoassays and therapy of disorders related to C3a Receptor polynucleotides or polypeptides, including fragments thereof. Such antibodies will preferably have an affinity for C3a Receptor polypeptides and/or C3a Receptor polypeptide fragments. Preferred binding affinities include those with a dissociation constant or $K_D$ of less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, antibodies of the invention bind C3a Receptor polypeptides or fragments or variants thereof with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, $10^{-8}$ M. Even more preferably, antibodies of the invention bind C3a Receptor polypeptides or fragments or variants thereof with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M. In a preferred embodiment, antibodies of the invention inhibit proliferation, differentiation, activation, chemotaxis, degranulation and/or apoptosis of C3a Receptor receptor expressing cells. In an additional preferred embodiment, antibodies of the invention induce differentiation of C3a Receptor expressing cells.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies or antibody compositions of the invention may be administered alone or in combination with other therapeutic agents, including but not limited to anti-diabetic agents, chemotherapeutic agents, antibiotics, antivirals, antiretroviral agents, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Combination Therapies with anti-C3a Receptor Antibodies, Anti-Inflammatory Drugs, and/or Immunomodulatory Agents In a preferred embodiment, the antibody compositions of the invention are administered alone or in combination with an anti-inflammatory agent. Anti-inflammatory agents that may be administered with the antibodies or antibody compositions include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In a preferred embodiment, the antibodies or antibody compositions are administered alone or in combination with a non-steroidal anti-inflammatory drug (NSAIDs). NSAIDs that may be administered with the antibodies or antibody compositions include, but are not limited to, Arthrotec (diclofenac™/misoprostol™), celecoxib (Celebrex™), diclofenac, Voltaren, Cataflam, Diflunisal (Dolobid™), Etodolac (Lodine), Flurbiprofen (Ansaid™), Ibupropen (Motrin), Indomethacin (Orudis™), Ketorolac (Toradol™), Nabumetone (Relafen™), (Naprosyn™), Oxaprozin (Daypro™), piroxicam (Feldene™), Rofecoxib (Vioxx™), Salsalate (Disalcid™), and Sulindac (Clinoril™).

In a preferred embodiment, the antibodies or antibody compositions are administered alone or in combination with mast cell stabilizing drugs. Mast cell stabilizing drugs that may be administered with the antibodies or antibody compositions include, but are not limited to, (Cromolyn (Intal™), Nedocromil (Tilade™)), Anticholinergic Drugs-lpratropium (Atrovent™) and ipratropium bromide/Albuterol sulfate (Combivent™).

In a preferred embodiment, the antibodies or antibody compositions are administered alone or in combination with anti-inflammatory drugs. Anti-inflammatory drugs that may be administered with the antibodies or antibody compositions include, but are not limited to, Corticosteroids, Beclomethasone dipropionate, QVAR™, Beclovent™, Vanceril™, Budesonide, Pulmicort™, Flunisolide, AeroBid™, Fluticasone aerosol spray (Flovent™), Fluticasone dry powder inhaler (Flovent™ Rotadisk™), and Triamcinolone acetonide (Azmacort™).

In a preferred embodiment, the antibodies or antibody compositions are administered alone or in combination with corticosteroids. Corticosteroids that may be administered with the antibodies or antibody compositions include, but are not limited to, Hydrocortisone, Prednisolone, Prednisone, Methylprednisolone, and Beclometasone.

In a preferred embodiment, the antibodies or antibody compositions are administered alone or in combination with anti-histamines. Anti-histamines that may be administered with the antibodies or antibody compositions include, but are not limited to, Chlorphenamine (Chlorpheniramine™), Diphenhydramine, Hydroxyzine, Cetirizine, Clemastine, Meclozine (meclizine™), Cimetidine, Famotidine, Nizatidine, Phenylpropanolamine, Butamirate, Dextromethorphan, Lagundi (Ascof™), Salbutamol, Salmeterol, Terbutaline, Theophylline, Fluticasone, and Ranitidine.

In other embodiments, antibody compositions of the invention may be administered in combination with anti-opportunistic infection agents. Anti-opportunistic agents that may be administered in combination with the albumin fusion proteins and/or polynucleotides of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF).

In a specific embodiment, antibodies or antibody compositions of the invention are administered in combination with steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells. Other immunosuppressive agents that may be administered in combination with the antibodies or antibody compositions include, but are not limited to, prednisolone, methotrexate, thalidomide, methoxsalen, rapamycin, leflunomide, mizoribine (BREDININ™), brequinar, deoxyspergualin, and azaspirane (SKF 105685), ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucocorticosteroids, adrenocortical steroids such as DELTASONET (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants may be used to prevent rejection of organ or bone marrow transplantation.

Additional Combination Therapies

In an additional embodiment, antibodies or antibody compositions of the invention are administered alone or in combination with an anti-angiogenic agent(s). Anti-angiogenic agents that may be administered with the antibodies or antibody compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals. Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates. Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d, L-3,4-dehydroproline, Thiaproline, alpha, alpha-dipyridyl, aminopropionitrile fumarate; 4-propyl-5-(4-pyridinyl)-2(3H)oxazolone; Methotrexate; Mitoxantrone; Heparin; Interferons; 2 Macroglobulin-serum; ChIMP-3 (Pavioff et al., J. Bio. Chem. 267:17321-17326, 1992); Chymostatin (Tomkinson et al., Biochem J. 286:475480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)0carboxyphenyl-4- chloroanthronilic acid disodium or "CCA"; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman J Pediatr. Surg. 28:445-51 (1993)); an integrin alpha v beta 3 antagonist (C. Storgard et al., *J Clin. Invest.* 103:47-54 (1999)); carboxynaminolmidazole; Carboxyamidotriazole (CAI) (National Cancer Institute, Bethesda, Md.); Conbretastatin A4 (CA4P) (OXiGENE, Boston, Mass.); Squalamine (Magainin Pharmaceuticals, Plymouth Meeting, Pa.); TNP470, (Tap Pharmaceuticals, Deerfield, Ill.); ZD-0101 AstraZeneca (London, UK); APRA (CT2584); Benefin, Byrostatin-1 (SC359555); CGP41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3540) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the antibodies and/or the antibodies or antibody compositions may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the antibodies or antibody compositions of the invention include, but are not limited to, AG-3540 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aetema, St-Foy, Quebec). Examples of anti-angiogenic inhibitors that act by blocking the function of endothelial cell-extracellular matrix adhesion molecules and which may be administered in combination with the antibodies or antibody compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the antibodies or antibody compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the antibodies or antibody compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In a further embodiment, the antibodies or antibody compositions of the invention are administered in combination with an antibiotic agent. Antibiotic agents that may be administered with the antibodies or antibody compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In a preferred embodiment, the antibodies or antibody compositions of the invention are administered in combination with steroid therapy. Steroids that may be administered in combination with the antibodies or antibody compositions of the invention, include, but are not limited to, oral corticosteroids, prednisone, and methylprednisolone (e.g., IV methylprednisolone). In a specific embodiment, antibodies or antibody compositions of the invention are administered in combination with prednisone.

The antibodies or antibody compositions of the invention may be administered alone or in combination with other adjuvants. Adjuvants that may be administered with the antibodies or antibody compositions of the invention include, but are not limited to, alum, alum plus deoxycholate (ImmunoAg), MTP-PE (Biocine Corp.), QS21 (Genentech, Inc.), BCG, and MPL. In a specific embodiment, antibodies or antibody compositions of the invention are administered in combination with alum. In another specific embodiment, antibodies or antibody compositions of the invention are administered in combination with QS-21. Further adjuvants that may be administered with the antibodies or antibody compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the antibodies or antibody compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, antibodies or antibody compositions of the invention are used in combination with PNEUMOVAX-23™ to treat, prevent, and/or diagnose infection and/or any disease, disorder, and/or condition associated therewith. In one embodiment, antibodies or antibody compositions of the invention are used in combination with PNEUMOVAX-23™ to treat, prevent, and/or diagnose any Gram positive bacterial infection and/or any disease, disorder, and/or condition associated therewith. In another embodiment, antibodies or antibody compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, antibodies or antibody compositions of the invention are used in any combination with PNEUMOVAX-23™ to treat, prevent, and/or diagnose infection and/or any disease, disorder, and/or condition associated with one or more members of the Group B streptococci. In another embodiment, antibodies or antibody compositions of the invention are used in combination with PNEUMOVAX-23™ to treat, prevent, and/or diagnose infection and/or any disease, disorder, and/or condition associated with *Streptococcus pneumoniae*.

In a preferred embodiment, the antibodies or antibody compositions of the invention are administered in combination with CD40 ligand (CD40L), a soluble form of CD40L (e.g., AVREND™), bioiligically active fragments, variants, or derivatives of CD40L, anti-CD40L antibodies (e.g., agonistic or antagonistic antibodies), and/or anti-CD40 antibodies (e.g., agonistic or antagonistic antibodies).

In a nonexclusive embodiment, the antibodies or antibody compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-714 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-100 (CarboMed), ML-3000 (Merckle), CB-2431 (KS Biomedix), CBF-BS2 (KS Biomedix), IL-IRa gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-671 (Merck), ST-1482 (Sigma-Tau), and butixocort propionate (WamerLambert).

In a preferred embodiment, the antibodies or antibody compositions of the invention are administered in combination with one, two, three, four, five or more of the following drugs: methotrexate, sulfasalazine, sodium aurothiomalate, auranofin, cyclosporine, penicillamine, azathioprine, an antimalarial drug, cyclophosphamide, chlorambucil, gold, ENBREL™ (Etanercept), anti-TNF antibody, LJP 394 (La Jolla Pharmaceutical Company, San Diego, Calif.) and prednisolone.

In an additional embodiment, antibodies or antibody compositions of the invention are administered alone or in combination with one or more intravenous immune globulin preparations. Intravenous immune globulin preparations that may be administered with the antibodies or antibody compositions of the invention include, but not limited to, GAMMAR™, IVEEGAM™, SANDOGLOBULIN™, GAMMAGARD S/D™, and GAMIMUNE™. In a specific embodiment, antibodies or antibody compositions of the invention are administered in combination with intravenous immune globulin preparations in transplantation therapy (e.g., bone marrow transplant).

In an additional embodiment, the antibodies or antibody compositions of the invention are administered in combination with other polypeptides, polynucleotides or antibodies used to treat diagnose or ameliorate diabetes, including, but not limited to other FIZZ and/or RELM family members, Apo-lipoprotein, Insulin, Interferon Alpha, M-CSF, Platelet factor 4, IL-2, Resistin, AC2 Inhibitor, Leptin, IL-1 Receptor Agonist, HLDOU18, HCE-IP80, GLP-1, ABC1, Adiposin, CNTF, CTLA4, Decorin, GGF-2, Glucagon, IL-10, IL-2-Diptheria Toxin Chimera, IL4, Microsomal Transfer Protein, NGF, NT-3, PAF acetyl hydrolase, PDGF, Prosaptide, TGF Beta 2, Troponin 1, Lp-PLA2, Fas, FasL, TR6, HNHFE71, HLWCF05, Preproapolipoprotein, BMP-1, BMP-2B, BMP-4, BMP-5, BMP-6, Osteogenic protein-2, GDF-1, BMP-9, BMP-10, BMP-12, BMP-15, BMP-17, BMP-18, APM-1, ACRP-30, Calpain 10a, Calpain-10b, Calpain-10c, and VEGF-1.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans (See, e.g., Examples 6 and 9).

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can be tested for their ability to reduce tumor formation in in vitro, ex vivo and in vivo assays. Antibodies or compositions of the invention can also be tested for their ability to inhibit viral replication or reduce viral load in in vitro and in vivo assays. Antibodies or compositions of the invention can also be tested for their ability to reduce bacterial numbers in in vitro and in vivo assays known to those of skill in the art. Antibodies or compositions of the invention can also be tested for their ability to alleviate of one or more symptoms associated with diabetes (e.g., insulin resistance). Antibodies or compositions of the invention can also be tested for their ability to decrease the time course of the infectious disease. Further, antibodies or compositions of the invention can be tested for their ability to increase the survival period of animals suffering from disease or disorder, including cancer, an immune disorder or an infectious disease. Techniques known to those of skill in the art can be used to analyze the function of the antibodies or compositions of the invention in vivo.

Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of an antibody or composition of the invention to induce B-cell proliferation is measured. In another preferred embodiment, the ability of an antibody or composition of the invention to modulate immunoglobulin expression is measured.

Panels/Mixtures

The present invention also provides for mixtures of antibodies (including scFvs and other molecules comprising, or alternatively consisting of, antibody fragments or variants thereof) that specifically bind to C3a Receptor or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that specifically bind to C3a Receptor or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that specifically bind to C3a Receptor or a fragment or variant thereof, wherein the panel has at least one, two, three, four, five or more different antibodies of the invention. In specific embodiments, the invention provides for panels of antibodies that have different affinities for C3a Receptor, different specificities for C3a Receptor, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including molecules comprising, or alternatively consisting of, antibody fragments or variants of the invention). In one embodiment, a composition of the present invention comprises, one, two, three, four, five, or more antibodies that comprise or alternatively consist of, a polypeptide having an amino acid sequence of any one or more of the VH domains of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of the scFvs referred to in Table 1, or variant thereof. In another embodiment, a composition of the present invention comprises, one, two, three, four, five or more antibodies that comprise, or alternatively consist of, a polypeptide having an amino acid sequence of any one or more of the VH CDR2s of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s of the scFvs referred to in Table 1, or a variant thereof.

Other embodiments of the present invention providing for compositions comprising, one or more antibodies (including molecules comprising, or alternatively consisting of, antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s of the scFvs referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that specifically binds to C3a Receptor polypeptides or fragments or variants thereof. In a specific embodiment, the kits of the present invention contain a substantially isolated C3a Receptor polypeptide or fragment or variant thereof as a control. Preferably, the kits of the present invention further comprise a control antibody which does not react with any, some or all C3a Receptor. In another specific embodiment, the kits of the present invention contain a means for detecting the binding of an antibody to C3a Receptor polypeptides (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized C3a Receptor. The C3a Receptor provided in the kit may also be attached to a solid support. In a more specific embodiment the detecting means of the above-described kit includes a solid support to which C3a Receptor is attached. Such a kit may also include a non-attached reporter-labeled anti- human antibody. In this embodiment, binding of the antibody to C3a Receptor can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with C3a Receptor, and means for detecting the binding of C3a Receptor polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having surface-bound C3a Receptor obtained by the methods of the present invention. After C3a Receptor polypeptides bind to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-C3a Receptor antibody on the solid support. Typically, the reporter is an enzyme which is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant C3a Receptor, and a reporter-labeled anti-human antibody for detecting surface-bound anti-C3a Receptor antibody.

Gene Therapy

In a specific embodiment, nucleic acids comprising sequences encoding antibodies or functional derivatives thereof, are administered to treat, inhibit or prevent a disease or disorder associated with aberrant expression and/or activity of C3a Receptor and/or its receptors, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH I 1(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Patent No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22715; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651(1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the-central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication W094/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, cosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

EXAMPLES

Example 1

Generation of Anti-c3A Receptor scFvs

General Methods

Rescue of the Library

A library of scFvs is constructed from the RNA of human PBLs as described in WO92/01047 (which is hereby incorporated by reference in its entirety). To rescue phage displaying antibody fragments, approximately 109 *E. coli* harboring the phagemid are used to inoculate 50 ml of 2×TY containing 1% glucose and 100 micrograms/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious Ml 3 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2×TY broth containing 100 micrograms ampicillin/ml and 25 micrograms kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library

Immunotubes (Nunc) are coated overnight in PBS with 4 ml of either 100 micrograms/ml or 10 micrograms/ml of a C3a Receptor receptor polypeptide. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 micrograms/ml ampicillin. The resulting bacterial library is then rescued with delta gene 3 helper phage as described above to prepare phage for a subsequent round of selection. This process is usually repeated for a total of 24 rounds of affinity purification.

Antigens that may be used to select for anti-C3a Receptor antibodies from phage display libraries, or other sources, include but are not limited to, peptides corresponding to all or portions of the extracellular domains of C3A receptor, and chimeric versions of the C3a Receptor. Preferred peptides that may be used as an selection agent for the identification of antibodies reactive with C3a Receptor consist of, or alternatively comprise, amino acid residues 82-99, 162-183, 299-315, 308-324, and/or 315-331 of the polypeptide of SEQ ID NO:2. The central portion of the second extracellular loop is an immunodominant epitope of C3a Receptor that results in the generation of antibodies that do not inhibit C3a binding to C3a Receptor (Hawlisch et al., (1998) The Journal of Immunology 160:2847-2958, which is hereby incorporated by reference in its entirety). Thus, a preferred variant of C3a Receptor that may be used as an to select for antibodies reactive with C3a Receptor that inhibit C3a binding to C3a Receptor consists of, or alternatively comprises, a human-murine C3a Receptor chimeric polypeptide in which amino acid residues 1-211 of human C3a Receptor (SEQ ID NO:2) are fused to amino acids residues 215 to 304 of murine C3a Receptor (SEQ ID NO:4) which is fused to amino acid residues 309-482 of SEQ ID NO:2. Another preferred variant of C3a Receptor that may be used to select for antibodies reactive with C3a Receptor that inhibit C3a binding to C3a Receptor consists of, or alternatively comprises, a human deletion mutant of C3a Receptor in which amino acids 212-308 of SEQ ID NO:2 are deleted resulting in the fusion of amino acid residues 1-211 of human C3a Receptor (SEQ ID NO:2) to amino acid residues 309-482 of SEQ ID NO:2. The above-described proteins may also be used in assays to characterize the binding sites of anti-C3a Receptor antibodies.

Characterization of Binders.

Eluted phage from the final rounds of selection are used to infect *E. coli* HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Example 2

Identification and Cloning of VH and VL domains

One method to identify and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may lysed in the TRIzol® reagent (Life Technologies, Rockville. Md.) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C in a tabletop centrifuge. Following centrifugation, the supernatant is and washed with 75% ethanol. Follwing washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5-2.5 micrograms of RNA using reverse transcriptase and random hexamer primers. cDNA is then used as a template for PCR amplification of VH and VL domains. Primers used to amplify VH and VL genes are shown in Table 8. Typically a PCR reaction makes use of a single 5' primer and a single 3' primer Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1×PCR buffer, 2 mM of each dNTP, 0.7 units of High Fidelity Taq polymerase, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 6

Primer Sequences Used to Amplify VH and VL domains.

| Primer name | SEQ ID NO | Primer Sequence (5'-3') |
| --- | --- | --- |
| VH Primers | | |
| Hu VH1-5' | 5 | CAGGTGCAGCTGGTGCAGTCTGG |
| Hu VH2-5' | 6 | CAGGTCAACTTAAGGGAGTCTGG |
| Hu VH3-5' | 7 | GAGGTGCAGCTGGTGGAGTCTGG |
| Hu VH4-5' | 8 | CAGGTGCAGCTGCAGGAGTCGGG |
| Hu VH5-5' | 9 | GAGGTGCAGCTGTTGCAGTCTGC |
| Hu VH6-5' | 10 | CAGGTACAGCTGCAGCAGTCAGG |
| Hu JH1, 2-5' | 11 | TGAGGAGACGGTGACCAGGGTGCC |
| Hu JH3-5' | 12 | TGAAGAGACGGTGACCATTGTCCC |
| Hu JH4, 5-5' | 13 | TGAGGAGACGGTGACCAGGGTTCC |
| Hu JH6-5' | 14 | TGAGGAGACGGTGACCGTGGTCCC |
| VL Primers | | |
| Hu Vkappa1-5' | 15 | GACATCCAGATGACCCAGTCTCC |
| Hu Vkappa2a-5' | 16 | GATGTTGTGATGACTCAGTCTCC |
| Hu Vkappa2b-5' | 17 | GATATTGTGATGACTCAGTCTCC |
| Hu Vkappa3-5' | 18 | GAAATTGTGTTGACGCAGTCTCC |
| Hu Vkappa4-5' | 19 | GACATCGTGATGACCCAGTCTCC |
| Hu Vkappa5-5' | 20 | GAAACGACACTCACGCAGTCTCC |
| Hu Vkappa6-5' | 21 | GAAATTGTGCTGACTCAGTCTCC |
| Hu Vlambda1-5' | 22 | CAGTCTGTGTTGACGCAGCCGCC |
| Hu Vlambda2-5' | 23 | CAGTCTGCCCTGACTCAGCCTGC |
| Hu Vlambda3-5' | 24 | TCCTATGTGCTGACTCAGCCACC |
| Hu Vlambda3b-5' | 25 | TCTTCTGAGCTGACTCAGGACCC |
| Hu Vlambda4-5' | 26 | CACGTTATACTGACTCAACCGCC |
| Hu Vlambda5-5' | 27 | CAGGCTGTGCTCACTCAGCCGTC |
| Hu Vlambda6-5' | 28 | AATTTGATGCTGACTCAGCCCCA |
| Hu Jkappa1-3' | 29 | ACGTTTGATCCACCTTGGTCCC |
| Hu Jkappa2-3' | 30 | ACGTTTGATCTCCAGCTTGGTCCC |
| Hu Jkappa3-3' | 31 | ACGTTTGATATCCACTTTGGTCCC |
| Hu Jkappa4-3' | 32 | ACGTTTGATCTCCACCTTGGTCCC |
| Hu Jkappa5-3' | 33 | ACGTTTAATCTCCAGTCGTGTCCC |
| Hu Jlambda1-3' | 34 | CAGTCTGTGTTGACGCAGCCGCC |
| Hu Jlambda2-3' | 35 | CAGTCTGCCCTGACTCAGCCTGC |
| Hu Jlambda3--3' | 36 | TCCTATGTGCTGACTCAGCCACC |
| Hu Jlambda3b-3' | 37 | TCTTCTGAGCTGACTCAGGACCC |
| Hu Jlambda4-3' | 38 | CACGTTATACTGACTCAACCGCC |
| Hu Jlambda5-3' | 39 | CAGGCTGTGCTCACTCAGCCGTC |
| Hu Jlambda6-3' | 40 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art.

One of skill in the art could routinely modify the above described PCR reaction in order to amplify VH and VL domains from other sources (e.g., plasmids encoding an scFv of the invention.).

Example 3

Cloning and Expression of C3a Receptor Using the Baculovirus Expression System.

The DNA sequence encoding the full length C3a Receptor protein, ATCC Deposit No. 75982, is amplified using PCR oligonucleotide primers corresponding to the 5' and 3' sequences of the gene:

The 5' primer has the sequence 5'-CGGGATCCCTC ATGCGTCTTTCTGCT-3' (SEQ ID NO:41) and contains a BamHI restriction enzyme site followed by four nucleotides resembling an efficient signal for the initiation of translation in eukaryotic cells (J. Mol. Biol. 1987, 196, 947-950, Kozak, M., which is just behind the first 18 nucleotides of the gene (the initiation codon for translation "ATG" is underlined).

The 3' primer has the sequence 5'-CGGGATCCCGCTCA-CACAGGTACT-3' (SEQ ID NO:42) and contains the cleavage site for the restriction endonuclease BamHI and the 3' primer has the sequence 5' 18 nucleotides complementary to the 3' non-translated sequence of the C3a Receptor gene. The amplified sequences are isolated from a 1% agarose gel using a commercially available kit (Geneclean, BIO 101 Inc., La Jolla, Calif.). The fragment is then digested with the endonuclease Baal and then isolated again on a 1% agarose gel. This fragment is designated F2.

The vector pRG1 (modification of pVL941 vector, discussed below) is used for the expression of the C3a Receptor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonuclease BamHI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170: 31-39).

The plasmid is digested with the restriction enzymes BamHI and then dephosphorylated using calf intestinal phosphatase by procedures known in the art. The DNA is then isolated from a 1% agarose gel as described above. This vector DNA is designated V2.

Fragment F2 and the dephosphorylated plasmid V2 are ligated with T4 DNA ligase. *E. coli* HB101 cells are then transformed and bacteria identified that contained the plasmid (pBacC3a Receptor) with the C3a Receptor gene using the enzyme BamHI The sequence of the cloned fragment is confirmed by DNA sequencing.

5 μg of the plasmid pBacC3a Receptor is co-transfected with 1.0 μg of a commercially available linearized baculovirus ("BaculoGoldn baculovirus DNA", Pharmingen, San Diego, Calif.) using the lipofection method (Felgner et al. Proc. Natl. Acad. Sci. USA, 84:7413-7417 (1987).

1 μg of BaculoGold virus DNA and 5 μg of the plasmid pBacC3a Receptor are mixed in a sterile well of a microtiter plate containing 50 μl of serum free Grace's medium (Life Technologies Inc., Gaithersburg, Md.). Afterwards 10 μl Lipofectin plus 90 pl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27°. After 5 hours the transfection solution from the plate and 1 ml of Grace's insect medium supplemented with 10% fetal calf serum is added. The plate is put back into an incubator and cultivation continued at 27 C for four days.

After four days the supernatant is collected and a plaque assay performed similar as described by Summers and Smith (supra). Antibodies or antibody compositions of the present invention may be used as a modification an agarose gel with "Blue Gal" (Life Technologies Inc., Gaithersburg) is used which detailed description of a "plaque assay" can also be found in the user's guide for insect cell culture and baculovirology distributed by Life Technologies Inc., Gaithersburg, page 9-10).

Four days after the serial dilution, the viruses are added to the cells and blue stained plaques are picked with the tip of an Eppendorf pipette. The agar containing the recombinant viruses is then resuspended in an Eppendorf tube containing 200 pl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-C3a Receptor at a multiplicity of infection (MOI) of 2. Six hours later the medium is removed and replaced with SF900 II medium minus methionine and cysteine (Life Technologies Inc., Gaithersburg). 42 hours later 5 μCi of 35S-methionine and 5 pCi 35S cysteine (Amersham) are added. The cells are further incubated for 16 hours before they are harvested by centrifugation and the labeled proteins visualized by SDS-PAGE and autoradiography.

Example 4

Expression Pattern of C3a Receptor in Human Tissue:

Northern blot analysis is carried out to examine the levels of expression of C3a Receptor in human tissues. Total cellular RNA samples are isolated with FIAzol" B system (Bioteck Laboratories, Inc. Houston, Tex.). About 10 μg of total RNA isolated from each human tissue specified is separated on 1% agarose gel and blotted onto a nylon filter (Sambrook, Fritsch, and Maniatis, Molecular Cloning Cold Spring Harbor Press, (1989)). The labeling reaction is done according to the Stratagene Prime-It kit with 50 ng DNA fragment. The labeled DNA is purified with a Select-G-50 column. (5 Prime-3 Prime, Inc. Boulder, Colo.). The filter is then hybridized with radioactive labeled full length C3a Receptor gene at 1,000,000 cpm/ml in 0.5 M NaPO$_4$, pH 7.4 and 7% SDS overnight at 65° C. After being washed twice at room temperature and twice at 60° C. with 0.5×SSC, 0.1% SDS, the filter is then exposed at −70° C. overnight with an intensifying screen. The message RNA for C3a Receptor is abundant in peripheral lymphocytes.

It will be clear that the invention may be practiced otherwise than as particularly described in the foregoing description and examples.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

The entire disclosures (including the specification, sequence listing, and drawings) of Provisional Application No. 60/400,057 filed Aug. 2, 2002, and International Application No. PCT/US2003/023826, filed Jul. 31, 2003, are herein incorporated by reference in their entireties.

What is claimed is:

1. An isolated antibody that specifically binds C3a Receptor polypeptide comprising:
    (a) an amino acid sequence that is at least 90% identical to the amino acid sequence of the VH domain of the scFv of SEQ ID NO:43 or SEQ ID NO:44;
    (b) an amino acid sequence that is at least 90% identical to the amino acid sequence of the VL domain of the scFv of SEQ ID NO:43 or SEQ ID NO:44; or
    (c) both (a) and (b).

2. The antibody of claim 1 comprising:
    (a) the amino acid sequence of the VH domain of the scFv of SEQ ID NO:43 or SEQ ID NO:44;
    (b) the amino acid sequence of the VL domain of the scFv of SEQ ID NO:43 or SEQ ID NO:44; or
    (c) both (a) and (b).

3. The antibody of claim 2 comprising the amino acid sequence of the VH domain of the scFv of SEQ ID NO:43 or SEQ ID NO:44 and the amino acid sequence of the VL domain of the scFv of SEQ ID NO:43 or SEQ ID NO:44.

4. The antibody of claim 3 wherein the VH domain and the VL domain are from the same scFv.

5. The isolated antibody of claim 1 that specifically binds C3a Receptor polypeptide purified from a cell culture, wherein said polypeptide is encoded by a polynucleotide encoding amino acids 1 to 482 of SEQ ID NO:2.

6. The antibody of claim 1 which is a whole immunoglobulin molecule, monoclonal, human, chimeric or humanized.

7. The antibody of claim 1 which is an scFv, a Fab fragment, an Fab' fragment, an F(ab')2, an Fv or a disulfide linked Fv.

8. The antibody of claim 1 which also comprises a heavy chain immunoglobulin constant domain selected from the group consisting of:
    (a) a human IgM constant domain;
    (b) a human IgG1 constant domain;
    (c) a human IgG2 constant domain;
    (d) a human IgG3 constant domain;
    (e) a human IgG4 constant domain; and
    (f) a human IgA constant domain.

9. The antibody of claim 1 which also comprises a light chain immunoglobulin constant domain selected from the group consisting of:
    (a) a human Ig kappa constant domain; and
    (b) a human Ig lambda constant domain.

10. A nucleic acid molecule encoding the antibody of claim 1.

11. The antibody of claim 1 wherein the antibody has a dissociation constant ($K_D$) less than or equal to $10^{-9}$M.

12. The antibody of claim 1 wherein the antibody is conjugated to a detectable label.

13. The antibody of claim 1 wherein said antibody specifically binds to C3a Receptor polypeptide in a Western blot or ELISA.

14. The antibody of claim 1 wherein the antibody inhibits the activity of C3a Receptor polypeptide expressing cells.

15. The antibody of claim 1 wherein the antibody inhibits C3a anaphylotoxin binding to the C3a Receptor polypeptide.

16. An antibody comprising the amino acid sequences of the VHCDR1, VHCDR2, VHCDR3, VLCDR1, VLCDR2, and VLCDR3 domains of the scFv of SEQ ID NO:43 or SEQ ID NO:44, wherein said antibody specifically binds C3a Receptor polypeptide.

17. The isolated antibody of claim 1 that specifically binds C3a Receptor polypeptide expressed on the surface of a cell, wherein said C3a polypeptide is encoded by a polynucleotide encoding amino acids 1 to 482 of SEQ ID NO:2.

18. A method of detecting C3a Receptor polypeptide in a biological sample comprising contacting the biological sample with the antibody of claim 1 and detecting said antibody specifically bound to said C3a Receptor polypeptide.

* * * * *

UNITED STATES PATENT AND TRADEMARK OFFICE
CERTIFICATE OF CORRECTION

| | | |
|---|---|---|
| PATENT NO. | : 7,425,622 B2 | Page 1 of 1 |
| APPLICATION NO. | : 11/046857 | |
| DATED | : September 16, 2008 | |
| INVENTOR(S) | : Craig A. Rosen | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (302) days Delete the phrase "by 302 days" and insert -- by 530 days --

Signed and Sealed this

Thirteenth Day of April, 2010

David J. Kappos
*Director of the United States Patent and Trademark Office*